United States Patent
Wainwright et al.

(10) Patent No.: US 12,158,471 B2
(45) Date of Patent: Dec. 3, 2024

(54) RECOMBINANT AMEBOCYTE LYSATE AND USES THEREOF

(71) Applicant: Charles River Laboratories, Inc., Wilmington, MA (US)

(72) Inventors: Norman R. Wainwright, Skaneateles, NY (US); Masakazu Tsuchiya, Mount Pleasant, SC (US); John Dubczak, Summerville, SC (US); Foster T. Jordan, Chapin, SC (US)

(73) Assignee: Charles River Laboratories, Inc., Wilmington, MA (US)

( * ) Notice: Subject to any disclaimer, the term of this patent is extended or adjusted under 35 U.S.C. 154(b) by 0 days.

(21) Appl. No.: 17/650,803

(22) Filed: Feb. 11, 2022

(65) Prior Publication Data

US 2023/0258647 A1    Aug. 17, 2023

(51) Int. Cl.
G01N 33/579    (2006.01)
C12N 9/64    (2006.01)
C12Q 1/34    (2006.01)

(52) U.S. Cl.
CPC ......... *G01N 33/579* (2013.01); *C12N 9/6408* (2013.01); *C12Q 1/34* (2013.01); *C12Y 304/21084* (2013.01); *C12Y 304/21085* (2013.01); *C12Y 304/21086* (2013.01); *G01N 2333/43504* (2013.01); *G01N 2333/96411* (2013.01)

(58) Field of Classification Search
None
See application file for complete search history.

(56) References Cited

U.S. PATENT DOCUMENTS

| | | | |
|---|---|---|---|
| 4,322,217 | A | 3/1982 | Dikeman |
| 5,155,032 | A | 10/1992 | Tanaka et al. |
| 5,179,006 | A | 1/1993 | Matuura et al. |
| 5,310,657 | A | 5/1994 | Berzofsky |
| 5,318,893 | A | 6/1994 | Matuura et al. |
| 5,474,984 | A | 12/1995 | Tanaka et al. |
| 5,605,806 | A | 2/1997 | Tanaka et al. |
| 5,641,643 | A | 6/1997 | Tanaka et al. |
| 5,712,144 | A | 1/1998 | Ding et al. |
| 5,716,834 | A | 2/1998 | Ding et al. |
| 5,858,706 | A | 1/1999 | Ding et al. |
| 5,985,590 | A | 11/1999 | Ding et al. |
| 6,077,946 | A | 6/2000 | Iwanaga et al. |
| 6,270,982 | B1 | 8/2001 | Jordan et al. |
| 6,391,570 | B1 | 5/2002 | Jordan et al. |
| 6,645,724 | B1 | 11/2003 | Ding et al. |
| 7,673,704 | B2 | 3/2010 | Phan et al. |
| 11,236,318 | B2 | 2/2022 | Mizumura et al. |
| 2019/0241629 | A1 | 8/2019 | Mizumura et al. |
| 2019/0270977 | A1 | 9/2019 | Mizumura et al. |
| 2021/0363564 | A1* | 11/2021 | Kobayashi ..... C12Y 304/21085 |

FOREIGN PATENT DOCUMENTS

| | | | |
|---|---|---|---|
| EP | 2930241 | A1 | 10/2015 |
| EP | 3441466 | A1 | 2/2019 |
| EP | 3591049 | A1 | 1/2020 |
| JP | 2019004705 | A | 1/2019 |
| WO | WO2018/074498 | * | 8/2019 |
| WO | WO-2020/071229 | A1 | 4/2020 |

OTHER PUBLICATIONS

Viswanathan et al., "Engineering Sialic Acid Synthesis Ability in Insect Cells", Chapter 12, in Alexandra Castilho (ed.), Glyco-Engineering: Methods and Protocols, Methods in Molecular Biology, vol. 1321, DOI 10. 1007/978-1-4939-2760-9_12, © Springer Science+Business Media New York 2015.*

Mizumura et al., "Genetic engineering approach to develop next-generation reagents for endotoxin quantification." *Innate immunity* vol. 23,2 (2017): 136-146.

Andersen, Dana C, and Lynne Krummen. "Recombinant protein expression for therapeutic applications." Current opinion in biotechnology vol. 13,2 (2002): 117-23.

Breitbach, K. and Jarvis, D. L., "Improved glycosylation of a foreign protein by Tn-5B1-4 cells engineered to express mammalian glycosyltransferases," Biotechnol Bioeng. Aug. 5, 2001;74(3):230-9.

Carlesso, E. et al., "The rule regulating pH changes during crystalloid infusion", Intensive Care Med., 2011, 37(3): 461-468.

Chen, S., et al., "Production of Recombinant Proteins in Mammalian Cells", Current Protocols in Protein Science, 1998, 5.10.1-5. 10.41.

Choo, K.H., et al., "A comprehensive assessment of N-terminal signal peptides prediction methods", BMC Bioinformatics, 2009, 1 0(Suppl 15):S2.

Croset et al. "Differences in the glycosylation of recombinant proteins expressed in HEK and CHO cells." Journal of biotechnology vol. 161,3 (2012): 336-48.

Demain and Vaishnav, "Production of recombinant proteins by microbes and higher organisms." *Biotechnology advances* vol. 27,3 (2009): 297-306.

Ding, J.L. and Navas, M.A.A, "Molecular cloning and sequence analysis of Factor C cDNA from the Singapore horseshoe crab, *Corcinoscorpius rotundicauda*", Malec. And Marine Biol. Biotechnol., 1995, 4(1), 90-103.

Ding, Jeak L. and Ho, Bow, "A new era in pyrogen testing", Trends in Biotech., 2001, 19(8): 277-281.

Dubczak et al, "Evaluation of limulus amebocyte lysate and recombinant endotoxin alternative assays for an assessment of endotoxin detection specificity." *European journal of pharmaceutical sciences : official journal of the European Federation for Pharmaceutical Sciences* vol. 159 (2021): 105716. doi:10.1016/j.ejps.2021.105716.

(Continued)

*Primary Examiner* — Suzanne M Noakes
(74) *Attorney, Agent, or Firm* — Goodwin Procter LLP

(57) ABSTRACT

The invention relates generally to hybrid amebocyte lysate compositions (including both native and recombinant components) and their use in detecting and/or quantifying endotoxin in a sample.

11 Claims, 16 Drawing Sheets

Specification includes a Sequence Listing.

(56) References Cited

OTHER PUBLICATIONS

Dwarakanath et al., "Recombinant COS-1 Cells express Carcinoscorpius rotundicauda Factor C," Biotechnology Letters, 19(4): 357-361, 1997.
Dwarakanath et al., "The Cys-rich and EGF-like domains of Carcinoscorpius rotundicauda Factor C yields soluble fusion with GFP," Biotechnology Letters, 19(1): 1147-1150, 1997.
Gerngross, Tillman U. "Advances in the production of human therapeutic proteins in yeasts and filamentous fungi." *Nature biotechnology* vol. 22,11 (2004): 1409-14.
Grallert et al. "EndoLISA®: A novel and reliable method for endotoxin detection" Nature Methods, 8:884, 2011.
Gray, David, "Overview of Protein Expression by Mammalian Cells", Current Protocols in Protein Science, 1997, 5.9.1-5.9.18.
Harada-Suzuki, T. et al., "Further Studies on the Chromogenic Substrate Assay Method for Bacterial Endotoxins Using Horseshoe Crab (*Tachypleus tridentatus*) Hemocyte Lysate", J. Biochem., 1982, 92(3): 793-800.
Hashiguchi et al., "Expression of Recombinant Protein Using Cultured Human Cells—Standard Protocol by 293-type cells"-, PSSJ Archives, 1, e017 (2008); with English Translation.
Hollister, J. R. and Jarvis, D. L., "Engineering lepidopteran insect cells for sialoglycoprotein production by genetic transformation with mammalian beta 1,4-galactosyltransferase and alpha 2,6-sialyltransferase genes," Glycobiology. Jan. 2001;11(1):1-9.
Hooker, A. D. et al, "Constraints on the transport and glycosylation of recombinant IFN-gamma in Chinese hamster ovary and insect cells," Biotechnol Bioeng. Jun. 5, 1999;63(5):559-572.
Hossler, Patrick et al. "Optimal and consistent protein glycosylation in mammalian cell culture." Glycobiology vol. 19,9 (2009): 936-49.
Inamori et al., "A horseshoe crab receptor structurally related to *Drosophila* Toll," J. Endotoxin Res. , 6(5):397-399, 2000.
Kingston et al., "Amplification Using CHO Cell Expression Vectors," Unit 16.23 in Current Protocols in Molecular Biology, John Wiley and Sons (1993), pp. 16.23.1-16.23.13.
Kobayashi et al., "Factor B Is the Second Lipopolysaccharide-binding Protease Zymogen in the Horseshoe Crab Coagulation Cascade." *The Journal of biological chemistry* vol. 290,31 (2015): 19379-86.
Kobayashi et al., "The N-terminal Arg residue is essential for autocatalytic activation of a lipopolysaccharide-responsive protease zymogen." *The Journal of biological chemistry* vol. 289,37 (2014): 25987-95.
Koshiba et al. "A structural perspective on the interaction between lipopolysaccharide and factor C, a receptor involved in recognition of Gram-negative bacteria." The Journal of biological chemistry vol. 282,6 (2007): 3962-7.
Levin et al. (1968), "Clottable Protein in Limulus: Its Localization and Kinetics of Its Coagulation by Endotoxin," Thromb. Diath. Haemorrh. 19: 186.
Lis et al. (1993), "Protein Glycosylation: Structural and functional aspects," Eur. J. Biochem. 218:1-27.
Loverock et al., "A Recombinant Factor C Procedure for the Detection of Gram-negative Bacterial Endotoxin," Pharmacopeial Forum, 35(6):1613-1621.
Muroi et al., "Application of a Recombinant Three-Factor Chromogenic Reagent, PyroSmart, for Bacterial Endotoxins Test Filed in the Pharmacopeias," Biol. Pharm. Bull, 42, 2024-2037, 2019.
Nettleship, Joanne E., "Structural Biology of Glycoproteins", Glycosylation, 2012, p. 41-62. Available from: https://www.intechopen.com/books/glycosylation/structural-biologyof- glycoproteins.
Nielson, H., et al., "Identification of prorkaryotic and eukaryotic signal peptides and prediction of their cleavage sites", Protein EnQineerinQ, 1997, 10(1 ): 1-6.
Parodi, A J. "Protein glucosylation and its role in protein folding." *Annual review of biochemistry* vol. 69 (2000): 69-93. Viswanathan et al. (2005) Biochem. 44:7526-7534.
Prior, 1990 "Clinical Applications of the *Limulus* Amebocyte Lysate Test" CRC Press 28-36 and 159-166.
Thomas, Philip, and Trevor G Smart. "HEK293 cell line: a vehicle for the expression of recombinant proteins." Journal of pharmacological and toxicological methods vol. 51,3 (2005): 187-200.
Tomiya et al. "Comparing N-glycan processing in mammalian cell lines to native and engineered lepidopteran insect cell lines." *Glycoconjugate journal* vol. 21,6 (2004): 343-60.
Tomiya et al. "Humanization of lepidopteran insect-cell-produced glycoproteins." *Accounts of chemical research* vol. 36,8 (2003): 613-20.
Viswanathan, et al., "Engineering intracellular CMP-sialic acid metabolism into insect cells and methods to enhance its generation," Biochemistry, May 24, 2005;44(20):7526-34.
Wang et al., "Functional expression of full length Limulus Factor C in stably transformed Sf9 cells," Biotechnology Letters, 23:71-76, 2001.
Wang et al., "Modular arrangement and secretion of a multidomain Serine Protease," J. Biol. Chem., 277(39):36363-36372, 2002.
Notice of Opposition to European Patent No. 3441466 (Proprietor: Seikagaku Corporation) filed by Opponent Sandra Pohlman in the European Patent Office on Nov. 5, 2020 (52 pages).
"A Comparison of *Limulus* Factor C expressed with and without terminal sialic acid glycosylation," Reference D19 filed Nov. 5, 2020, in Opposition of European Patent No. 3441466 (7 pages).
"Declaration under 37 C.F.R. § 1.132 of Hikaru Mizumura" filed in U.S. Appl. No. 14/650,767, filed Feb. 22, 2018; Reference D18 filed Nov. 5, 2020, in Opposition of European Patent No. 3441466 (5 pages).
"DNA Repair: Mutations Can Have Severe Consequences for an Organism," p. 209 in Alberts et al. *Essential Cell Biology, 2nd Ed.*, Garland Science, Taylor & Francis Group: New York & London, 2004; Reference D17 filed Nov. 5, 2020, in Opposition of European Patent No. 3441466 (3 pages).
"Declaration under 37 C.F.R. § 1.132 of Hikaru Mizumura" filed in U.S. Appl. No. 14/650,767, filed Oct. 12, 2017; Reference D16 filed Nov. 5, 2020, in Opposition of European Patent No. 3441466 (5 pages).
"Horseshoe Crab" from Wikipedia.org dated Nov. 23, 2012, accessed at https://web.archive.org/web/20111123165431/https://en.wikipedia.org/wiki/Horseshoe_crab; Reference D6 filed Nov. 5, 2020, in Opposition of European Patent No. 3441466 (4 pages).
"Blood Plasma" from Wikipedia.org dated Nov. 19, 2012, accessed at https://web.archive.org/web/20121119115732/https://en.wikipedia.org/wiki/Blood_plasma; Reference D5 filed Nov. 5, 2020, in Opposition of European Patent No. 3441466 (5 pages).
European Search Opinion for European Patent Application No. 18190686.8 (EP3441466) issued Jan. 10, 2019; Reference D1 filed Nov. 5, 2020, in Opposition of European Patent No. 3441466 (3 pages).
Certified English Translation of Japanese Patent Application No. 2012-269840 filed Dec. 10, 2012, the Priority Document for International Application No. PCT/JP2013/083082 and EP3441466; Reference P1 filed Nov. 5, 2020, in Opposition of European Patent No. 3441466 (54 pages).
Response filed in the European Patent Office on Mar. 18, 2021 by Proprietor Seikagaku Corporation to Notice of Opposition to European Patent No. 3441466 (46 pages).
Pertsemlidis and Fondon, "Having a BLAST with bioinformatics (and avoid BLASTphemy)," Genome Biology, 2(10): reviews Jan. 2002-Oct. 2002; Submitted as Appendix A (Reference D20) to Proprietor Seikagaku's Response to Notice of Opposition in European Patent No. EP3441466 on Mar. 18, 2021 (10 pages).
Declaration of Hikaru Mizumura dated Feb. 24, 2021, submitted as Appendix B (Reference D21) to Proprietor Seikagaku's Response to Notice of Opposition in European Patent No. EP3441466 on Mar. 18, 2021 (9a pages).
Muta et al., "Limulus Factor C," *J. Biol. Chem*., 266(10): 6554-6561, 1991; Submitted as Appendix B, Reference 1 (Reference D21-1) to Proprietor Seikagaku's Response to Notice of Opposition in European Patent No. EP3441466 on Mar. 18, 2021 (8 pages).
Kawabata et al., "The lipopolysaccharide-activated innate immune response network of the horseshoe crab," *Invertebrate Survival Journal*, 6:59-77, 2009; Submitted as Appendix B, Reference 3

(56) References Cited

OTHER PUBLICATIONS (Reference D21-III) to Proprietor Seikagaku's Response to Notice of Opposition in European Patent No. EP3441466 on Mar. 18, 2021 (19 pages).
Nakamura et al., "Lipopolysaccharide-sensitive serine-protease zymogen (Factor C) found in Limulus hemocytes: isolation and characterization," *Eur. J. Biochem.*, 154:511-521, 1986; Submitted as Appendix B, Reference 4 (Reference D21-IV) to Proprietor Seikagaku's Response to Notice of Opposition in European Patent No. EP3441466 on Mar. 18, 2021 (11 pages).
Navas et al., "Inactivation of Factor C by Dimethyl Sulfoxide Inhibits Coagulation of the Carcinscorpius Amoebocyte Lysate," *Biochemistry International*, 21(5): 805-813; 1990 (9 pages); Submitted as Appendix B, Reference 6 (Reference D21-VI) to Proprietor Seikagaku's Response to Notice of Opposition in European Patent No. EP3441466 on Mar. 18, 2021 (9 pages).
Tokunaga et al., "Further Studies on Lipopolysaccharide-Sensitive Serine Protease Zymogen (Factor C): Its Isolation from *Limulus polyphemus* Hemocytes and Identification as an Intracellular Zymogen Activated by α-Chymotrypsin, Not by Trypsin," *J. Biochem.*, 109:150-157, 1991; Submitted as Appendix B, Reference 7 (Reference D21-VII) to Proprietor Seikagaku's Response to Notice of Opposition in European Patent No. EP3441466 on Mar. 18, 2021 (8 pages).
Iwanaga et al., "Biochemical principle of *Limulus* test for detecting bacterial endotoxins," *Proc. Jpn. Acd., Ser. B.*, 83:110-119, 2007; Submitted as Appendix C (Reference D22) to Proprietor Seikagaku's Response to Notice of Opposition in European Patent No. EP3441466 on Mar. 18, 2021 (10 pages).
Ferrer-Miralles et al., "General Introduction: Recombinant Protein Production and Purification of Insoluble Proteins," Chapter 1 in Elena Garcia-Fruitos (ed.), *Insoluble Proteins: Methods and Protocols*, Methods in Molecular Biology, vol. 1258, 2015; Submitted as Appendix D (Reference D23) to Proprietor Seikagaku's Response to Notice of Opposition in European Patent No. EP3441466 on Mar. 18, 2021 (24 pages).
Summons to Attend Oral Proceedings and Provisional and Non-Binding Opinion of the Opposition Division of the European Patent Office in Opposition of European Patent No. EP3441466 mailed from the European Patent Office on Jul. 5, 2021 (28 pages).
Written Submission of Proprietor Seikagaku Corporation submitted to the European Patent Office on Aug. 3, 2022, in advance of Oral Proceedings in Opposition of European Patent No. EP3441466 (100 pages).
Declaration of Hikaru Mizumura dated Jun. 13, 2022, submitted as Annex A to Proprietor Seikagaku's Written Submissions in advance of Oral Proceedings in Opposition of European Patent No. EP3441466 on Aug. 3, 2022 (8 pages).
Rietschel et al., "Bacterial endotoxin: Molecular relationship of structure to activity and function," *FASEB J.*, 8:217-225, 1994; submitted as Annex B to Proprietor Seikagaku's Written Submissions in advance of Oral Proceedings in Opposition of European Patent No. EP3441466 on Aug. 3, 2022 (9 pages).
Written Submission of Opponent submitted to the European Patent Office on Aug. 4, 2022, in advance of Oral Proceedings in Opposition of European Patent No. EP2441466 (46 pages).
Alignment of a Factor C derived from *Tachypleus tridentatus* and a Factor C derived from *Limulus polyphemus*; Reference D24 filed by Opponent on Aug. 4, 2022, in Opposition of European Patent No. 3441466 (2 pages).
Decision T0354/97 of the European Patent Office Boards of Appeal dated May 3, 2000; Reference D27 filed by Opponent on Aug. 4, 2022, in Opposition of European Patent No. 3441466 (29 pages).
"Roche DIG Glycan Differentiation Kit" Version 17, Aug. 2018; Reference D28 filed by Opponent on Aug. 4, 2022, in Opposition of European Patent No. 3441466 (5 pages).
Response by Seikagaku Corporation in European Patent Application No. 13862466.3 dated Apr. 5, 2018; Reference D31 filed by Opponent on Aug. 4, 2022, in Opposition of European Patent No. 3441466 (6 pages).

"Intravenous Sodium Bicarbonate" from Wikipedia.org dated Apr. 25, 2013, accessed at https://web.archive.org/web/20130425182728/https://en.wikipedia.org/wiki/Intravenous_sodium_bicarbonate; Reference D32 filed by Opponent on Aug. 4, 2022, in Opposition of European Patent No. 3441466 (3 pages).
"Sodium Bicarbonate" from Pubchem accessed on Jul. 5, 2022, via https://pubchem.ncbi.nlm.nih.gov/compound/Sodium-bicarbonate; Reference D33 filed by Opponent on Aug. 4, 2022, in Opposition of European Patent No. 3441466 (1 page).
Further Written Submission of Opponent submitted to the European Patent Office on Sep. 1, 2022, in advance of Oral Proceedings in Opposition of European Patent No. EP2441466 (31 pages).
Chen et al., "Production of Recombinant Proteins in Mammalian Cells," *Current Protocols in Protein Science*, 1998, 5.10.1-5.10.41; Reference D39 filed by Opponent on Sep. 1, 2022, in Opposition of European Patent No. 3441466 (41 pages).
Gray et al., "Overview of Protein Expression by Mammalian Cells," *Current Protocols in Protein Science*, 1997, 5.9.1-5.9.18; Reference D38 filed by Opponent on Sep. 1, 2022, in Opposition of European Patent No. 3441466 (18 pages).
"Signal Peptide" from Wikipedia.org dated Nov. 23, 2012, accessed at https://web.archive.org/web/20121123202612/https://en.wikipedia.org/wiki/Signal_peptide; Reference D40 filed by Opponent on Sep. 1, 2022, in Opposition of European Patent No. 3441466 (3 pages).
Choo et al., "A comprehensive assessment of N-terminal signal peptides prediction methods," *BMC Bioinformatics*, 2009, 10(Suppl 15):S2; Reference D41 filed by Opponent on Sep. 1, 2022, in Opposition of European Patent No. 3441466 (12 pages).
Nielsen et al., "Identification of prokaryotic and eukaryotic signal peptides and prediction of their cleavage sites," *Protein Engineering*, 10(1):1-6, 1997; Reference D42 filed by Opponent on Sep. 1, 2022, in Opposition of European Patent No. 3441466 (6 pages).
"SignalP 6.0 Server predicts the presence of signal peptides and their cleavage sites in all domains of life" accessed from https://www.healthtech.dtu.dk/english/services.php? SignalP; Reference D44 filed by Opponent on Sep. 1, 2022, in Opposition of European Patent No. 3441466 (1 page).
"SignalP results for the Factor C sequence derived from *Carcinoscorpius rotundicauda*"; Reference D43 filed by Opponent on Sep. 1, 2022, in Opposition of European Patent No. 3441466 (1 page).
"SignalP results for the Factor C sequence derived from Limulus polyphemus"; Reference D48 filed by Opponent on Sep. 1, 2022, in Opposition of European Patent No. 3441466 (1 pages).
"FreeStyleTM 293 Expression System: For large-scale transfection of suspension 293 cells in a defined, serum-free medium," Version D, Oct. 28, 2010, Invitrogen, Carlsbad, CA; Reference D49 filed by Opponent on Sep. 1, 2022, in Opposition of European Patent No. 3441466 (23 pages).
"FreeStyleTM MAX Reagent Protocol," Rev. 2013, Invitrogen by Life Technologies; Reference D50 filed by Opponent on Sep. 1, 2022, in Opposition of European Patent No. 3441466 (3 pages).
Hashiguti et al., "*Expression of Recombinant Protein Using Cultured Human Cells—Standard Protocol by 293-type cells*," PSSJ Archives, 1, e017 (2008); Reference D51 in Japanese Language filed by Opponent on Sep. 1, 2022, in Opposition of European Patent No. 3441466 (13 pages), and an English machine translation thereof submitted as Reference D51a by Opponent on Sep. 8, 2022 (6 pages).
Ding et al., "Molecular cloning and sequence analysis of Factor C cDNA from the Singapore horseshoe crab, *Carcinoscorpius rotundicauda*," Molecular Marine Biology and Biotechnology, 4(1):90-103, 1995; Reference D46 filed by Opponent on Sep. 1, 2022, in Opposition of European Patent No. 3441466 (14 pages).
NCBI Database Entry for the Factor C Sequence derived from *Carcinoscorpius rotundicauda* accessed at https://www.ncbi.nlm.nih.gov/protein/AAB34361.1 on Aug. 23, 2022; Reference D45 filed by Opponent on Sep. 1, 2022, in Opposition of European Patent No. 3441466 (2 pages).
Proprietor Seikagaku's Response to Opponent's Sep. 1, 2022, Written Submissions, filed with European Patent Office on Sep. 20, 2022, in the Opposition of European Patent No. 3441466 (4 pages).

(56) References Cited

OTHER PUBLICATIONS

Proprietor Seikagaku's Second Response to Opponent's Sep. 1, 2022, Written Submissions, filed with European Patent Office on Sep. 27, 2022, in the Opposition of European Patent No. 3441466 (11 pages).
Declaration of Hikaru Mizumura dated Aug. 9, 2022, submitted by Proprietor Seikagaku Corporation on Sep. 27, 2022, as Reference D60 in the Opposition of European Patent No. EP3441466 on Mar. 18, 2021 (8 pages).
Decision of the Opposition Division of the European Patent Office in the Opposition of European Patent No. EP3441466 dated Jun. 3, 2022 (2 pages).
Decision of the Opposition Division of the European Patent Office Revoking European Patent No. EP3441466 and Minutes of the Oral Proceedings in the Opposition of European Patent No. EP3441466 dated Oct. 26, 2022 (37 pages).
Notice of Appeal by Proprietor Seikagaku Corporation Against Decision of the Opposition Division of the European Patent Office Revoking European Patent No. EP3441466 filed Dec. 22, 2022 (1 page).
Grounds of Appeal by Proprietor Seikagaku Corporation Against Decision of the Opposition Division of the European Patent Office Revoking European Patent No. EP3441466 filed Feb. 24, 2023 (44 pages).
Opponent's Reply to Seikagaku's Grounds of Appeal filed Jul. 12, 2023, in Appeal Against Decision of the Opposition Division of the European Patent Office Revoking European Patent No. EP3441466 (106 pages).

\* cited by examiner

| Etx (EU/mL) | Gel |
|---|---|
| 0.0078 | Negative |
| 0.0078 | Negative |
| 0.0156 | Positive |
| 0.0156 | Positive |
| 0.03 | Positive |
| 0.03 | Positive |
| 0.06 | Positive |
| 0.06 | Positive |
| 0.125 | Positive |
| 0.125 | Positive |
| 0.25 | Positive |
| 0.25 | Positive |
| 0.5 | Positive |
| 0.5 | Positive |

| Etx (EU/mL) | Gel |
|---|---|
| 0.0078 | Negative |
| 0.0078 | Negative |
| 0.0156 | Negative |
| 0.0156 | Negative |
| 0.03 | Negative |
| 0.03 | Negative |
| 0.06 | Negative |
| 0.06 | Negative |
| 0.125 | Negative |
| 0.125 | Negative |
| 0.25 | Negative |
| 0.25 | Negative |
| 0.5 | Negative |
| 0.5 | Negative |

| Host cells for Factor C | Endotoxin (EU/mL) | Absorbance change rate (av +/- SD, mAbs/min) |
|---|---|---|
| HEK293 | 0 | 0.32 +/- 0.02 |
| | 0.025 | 3.21 +/- 0.11 |
| | 0.05 | 6.77 +/- 0.13 |
| | 0.1 | 12.62 +/- 0.20 |
| HEK293 GnTI- | 0 | 0.97 +/- 0.02 |
| | 0.025 | 5.38 +/- 0.20 |
| | 0.05 | 10.43 +/- 0.15 |
| | 0.1 | 18.0 +/- 0.27 |

SEQUENCE LISTING

<160> NUMBER OF SEQ ID NOS: 19

<210> SEQ ID NO 1
<211> LENGTH: 3063
<212> TYPE: DNA
<213> ORGANISM: Limulus polyphemus

<400> SEQUENCE: 1

```
atggtgcttg cctcctttct cgtgtccggt cttgtgctcg gcctcctcgc ccaaaagatg      60
cgacccgtgc agtccagagg agtggacctg ggcctgtgcg acgatacccg gttcgagtgc     120
aaatgcggcg acccgggtta cgtgttcaat gtgcctgcga agcagtgtac ctactttac      180 cgctggcgcc cttactgcaa gccatgcgac aagcttgagg ctaaagatgt gtgccccaag     240
tacaagaggt gccaagaatg ccgcgccggc ctggattcat gcgtgagctg ccccccaaac     300
aaatacggca cttggtgctc cggggagtgc cagtgcaaga acggcggaat ctgcgaccag     360
```

```
aggaccgggg cctgcacttg ccgggaccgc tacgaggggg tgcattgcga gatcctgcag    420
ggttgcccgc tgctgcagtc cgaccccccaa gtgcaggagg tcaagaaccc ccccaacgac   480
ccgcagacca tcgactactc ctgttcacct gggttcaagc tgaagggcgt ggcacggatt   540
acgtgcctcc ccaacggaca gtggtcatcc ttccccccta agtgcattcg ggagtgcagc   600
atggtgtcga gcttggaaca cggaaaggtc aactccccga cgccgaccct gattgagggg   660
gcgacccttc ggttctcgtg cgactccccc tattacctga tcggtcagga aaccctgacg   720
tgccagggca acggccaatg gtcggggcag atcccgcagt gtcagaagct cgtgttttgt   780
cccgatttgg acccagtgtc ccatgccgaa caccaggtca agatcggact ggaacagaaa   840
tacggacagt tcccccaagg cactgaagtc acttacactt gcaccggaaa ctacttcctg   900
atgggcctgg acaccctcaa gtgcaatccc gacggatcct ggtcgggcac tcagccgtcc   960
tgcgtgaaag tggcagacag agaagtgaac tgtgatagca aagctgtgga cttcctggac  1020
gacgtgggcg aaccggtccg catccactgc ccggccgggt gcagcctgac cgcgggtact  1080
gtctggggta ccgccatcta tcatgaactt tcgtccgtct gccgggccgc cattcacgcc  1140
ggaaaggtcc cgaatagcgg cggtgcagtg cacgtcgtga caacggaccc tactcggat   1200
ttcctcgcct cggacttgaa tggcattaag tccgacgagc tgaagtccct ggcccagtcc  1260
ttccggttcg actacgtgtc atccagcacg gccggacgga agtcgggctg ccctgatggc  1320
tggttcgaaa tcaagagaa ttgtgtctac gtgacctcaa agcagagagc ctgggaacgg   1380
gctcagggag tctgcactaa catggctgcc cggttggccg tgctcgacaa ggatgtgatc  1440
ccgtcctcgc tcactgaaac cctgcgggga aagggactgg ctaccacttg gatcggactg  1500
cacaggctcg atgcggacaa ccacttcatc tgggaactga tggaccgctc ctccgtggcc  1560
ctgaacgaca gcctgacctt ctgggcccct ggagagccag gaaacgaaac caactgcgtg  1620
tacctggaca tccaggacca actgcagcct gtctggaaaa ccaagtcgtg ctttcaaccc  1680
tcctctttcg tgtgcatgat ggacctgagc gataagaaca aggccaagtg caaggatccc  1740
ggcccgctcg agaacggtca cgcgaagctg cacgggcagt ccatcgacgg cttctatgcc  1800
ggttcctccg tgcgctactc gtgtgaagtg ttgcactacc tgtccggtac cgaaaccgtg  1860
tcctgtacct ccaacgggac ttggtcggcc ccgaagccac gctgtattaa ggtcatcacc  1920
tgtcagactc cgcctgtccc gtcctacggg tccgtggata tcaagccccc gagccggact  1980
aactcgatta gccgcgtggg ctcacccttt ctgcggctcc caaggttgcc gcttccgctg  2040
gcccgggcgg ccggccccgcc tccgaagcct agatccgcgc ctccgtccac cgtggatttg  2100
tccagcaaag tcaagctccc tgagggacat tacagagtgg gatcccaggc catctacact  2160
tgcgaatcac gctattacga gctgctcgga tcgcaaggca gacgctgtga cagcaacgga  2220
aagtggtcgg gcagaccggc cagctgtatt cccgtgtgcg ggcggagcga ctcgcctcgc  2280
tccccccttca tcgtgaacgg aaactcaacc gaaatcggcc agtggccgtg caggccgga   2340
atctctcggt ggctggctga tcataacatg tggttcctgc aatgcgggg cgccctgctg   2400
aacgagaagt ggataatcac agccgctcac tgcgtgacat actcggcaac cgccgaaatc  2460
atcgatccct cccaattcaa gttctacctg ggaaagtact accgggatga ctctaaggac  2520
gacgattatg tgcaagtccg ggaagccatt gagatccacg tgaaccctaa ctacgatccg  2580
ggaaatctga acttcgacat tgcgctgatc cagctgaaaa cctccgtggc gctgaccact  2640
cgcgtccagc cgatctgcct ccccactgac ctgaccacac gggagaacct gaaggaaggg  2700
gccctggcag tcgtgaccgg atggggactc aacgagaaca acacctactc cgagatgatc  2760
```

```
cagcaggccg tgctccctgt ggtggcggcc agcacctgtg aacagggcta ccaggactcc   2820
ggcctcccac tgactgtgac tgagaacatg ttctgtgccg ggtacaagca ggggcgctac   2880
gacgcgtgtt ccggcgacag cggcgggcca ctggtgttcg ccgacgactc gaggaccgac   2940
cggcgctggg tgctcgaggg tattgtgtcc tggggatccc ccaacggatg cgggaagtcc   3000
aaccaatacg gcggattcac caaggtcaac gtgttcttgt cctggattcg ccagttcatc   3060
tga                                                                 3063
```

<210> SEQ ID NO 2
<211> LENGTH: 995
<212> TYPE: PRT
<213> ORGANISM: Limulus polyphemus

<400> SEQUENCE: 2

```
Arg Gly Val Asp Leu Gly Leu Cys Asp Asp Thr Arg Phe Glu Cys Lys
1               5                   10                  15

Cys Gly Asp Pro Gly Tyr Val Phe Asn Val Pro Ala Lys Gln Cys Thr
            20                  25                  30

Tyr Phe Tyr Arg Trp Arg Pro Tyr Cys Lys Pro Cys Asp Lys Leu Glu
        35                  40                  45

Ala Lys Asp Val Cys Pro Lys Tyr Lys Arg Cys Gln Glu Cys Arg Ala
    50                  55                  60

Gly Leu Asp Ser Cys Val Ser Cys Pro Pro Asn Lys Tyr Gly Thr Trp
65                  70                  75                  80

Cys Ser Gly Glu Cys Gln Cys Lys Asn Gly Gly Ile Cys Asp Gln Arg
                85                  90                  95

Thr Gly Ala Cys Thr Cys Arg Asp Arg Tyr Glu Gly Val His Cys Glu
            100                 105                 110

Ile Leu Gln Gly Cys Pro Leu Leu Gln Ser Asp Pro Gln Val Gln Glu
        115                 120                 125

Val Lys Asn Pro Pro Asn Asp Pro Gln Thr Ile Asp Tyr Ser Cys Ser
    130                 135                 140

Pro Gly Phe Lys Leu Lys Gly Val Ala Arg Ile Thr Cys Leu Pro Asn
145                 150                 155                 160

Gly Gln Trp Ser Ser Phe Pro Pro Lys Cys Ile Arg Glu Cys Ser Met
                165                 170                 175

Val Ser Ser Leu Glu His Gly Lys Val Asn Ser Pro Ser Ala Asp Leu
            180                 185                 190

Ile Glu Gly Ala Thr Leu Arg Phe Ser Cys Asp Ser Pro Tyr Tyr Leu
        195                 200                 205

Ile Gly Gln Glu Thr Leu Thr Cys Gln Gly Asn Gly Gln Trp Ser Gly
    210                 215                 220

Gln Ile Pro Gln Cys Gln Lys Leu Val Phe Cys Pro Asp Leu Asp Pro
225                 230                 235                 240

Val Ser His Ala Glu His Gln Val Lys Ile Gly Leu Glu Gln Lys Tyr
                245                 250                 255

Gly Gln Phe Pro Gln Gly Thr Glu Val Thr Tyr Thr Cys Thr Gly Asn
            260                 265                 270

Tyr Phe Leu Met Gly Leu Asp Thr Leu Lys Cys Asn Pro Asp Gly Ser
        275                 280                 285

Trp Ser Gly Thr Gln Pro Ser Cys Val Lys Val Ala Asp Arg Glu Val
    290                 295                 300

Asn Cys Asp Ser Lys Ala Val Asp Phe Leu Asp Asp Val Gly Glu Pro
```

```
            305                 310                 315                 320
Val Arg Ile His Cys Pro Ala Gly Cys Ser Leu Thr Ala Gly Thr Val
                    325                 330                 335
Trp Gly Thr Ala Ile Tyr His Glu Leu Ser Ser Val Cys Arg Ala Ala
                    340                 345                 350
Ile His Ala Gly Lys Val Pro Asn Ser Gly Ala Val His Val Val
                    355                 360                 365
Asn Asn Gly Pro Tyr Ser Asp Phe Leu Ala Ser Asp Leu Asn Gly Ile
            370                 375                 380
Lys Ser Asp Glu Leu Lys Ser Leu Ala Gln Ser Phe Arg Phe Asp Tyr
385                 390                 395                 400
Val Ser Ser Ser Thr Ala Gly Arg Lys Ser Gly Cys Pro Asp Gly Trp
                    405                 410                 415
Phe Glu Ile Glu Glu Asn Cys Val Tyr Val Thr Ser Lys Gln Arg Ala
                    420                 425                 430
Trp Glu Arg Ala Gln Gly Val Cys Thr Asn Met Ala Ala Arg Leu Ala
                    435                 440                 445
Val Leu Asp Lys Asp Val Ile Pro Ser Ser Leu Thr Glu Thr Leu Arg
            450                 455                 460
Gly Lys Gly Leu Ala Thr Thr Trp Ile Gly Leu His Arg Leu Asp Ala
465                 470                 475                 480
Asp Asn His Phe Ile Trp Glu Leu Met Asp Arg Ser Ser Val Ala Leu
                    485                 490                 495
Asn Asp Ser Leu Thr Phe Trp Ala Pro Gly Glu Pro Gly Asn Glu Thr
                    500                 505                 510
Asn Cys Val Tyr Leu Asp Ile Gln Asp Gln Leu Gln Pro Val Trp Lys
                    515                 520                 525
Thr Lys Ser Cys Phe Gln Pro Ser Ser Phe Val Cys Met Met Asp Leu
                    530                 535                 540
Ser Asp Lys Asn Lys Ala Lys Cys Lys Asp Pro Gly Pro Leu Glu Asn
545                 550                 555                 560
Gly His Ala Lys Leu His Gly Gln Ser Ile Asp Gly Phe Tyr Ala Gly
                    565                 570                 575
Ser Ser Val Arg Tyr Ser Cys Glu Val Leu His Tyr Leu Ser Gly Thr
                    580                 585                 590
Glu Thr Val Ser Cys Thr Ser Asn Gly Thr Trp Ser Ala Pro Lys Pro
                    595                 600                 605
Arg Cys Ile Lys Val Ile Thr Cys Gln Thr Pro Pro Val Pro Ser Tyr
            610                 615                 620
Gly Ser Val Asp Ile Lys Pro Pro Ser Arg Thr Asn Ser Ile Ser Arg
625                 630                 635                 640
Val Gly Ser Pro Phe Leu Arg Leu Pro Arg Leu Pro Leu Pro Leu Ala
                    645                 650                 655
Arg Ala Ala Gly Pro Pro Lys Pro Arg Ser Ala Pro Pro Ser Thr
                    660                 665                 670
Val Asp Leu Ser Ser Lys Val Lys Leu Pro Glu Gly His Tyr Arg Val
            675                 680                 685
Gly Ser Gln Ala Ile Tyr Thr Cys Glu Ser Arg Tyr Tyr Glu Leu Leu
            690                 695                 700
Gly Ser Gln Gly Arg Arg Cys Asp Ser Asn Gly Lys Trp Ser Gly Arg
705                 710                 715                 720
Pro Ala Ser Cys Ile Pro Val Cys Gly Arg Ser Asp Ser Pro Arg Ser
                    725                 730                 735
```

```
Pro Phe Ile Val Asn Gly Asn Ser Thr Glu Ile Gly Gln Trp Pro Trp
                740                 745                 750

Gln Ala Gly Ile Ser Arg Trp Leu Ala Asp His Asn Met Trp Phe Leu
            755                 760                 765

Gln Cys Gly Gly Ala Leu Leu Asn Glu Lys Trp Ile Ile Thr Ala Ala
770                 775                 780

His Cys Val Thr Tyr Ser Ala Thr Ala Glu Ile Ile Asp Pro Ser Gln
785                 790                 795                 800

Phe Lys Phe Tyr Leu Gly Lys Tyr Tyr Arg Asp Asp Ser Lys Asp Asp
                805                 810                 815

Asp Tyr Val Gln Val Arg Glu Ala Ile Glu Ile His Val Asn Pro Asn
            820                 825                 830

Tyr Asp Pro Gly Asn Leu Asn Phe Asp Ile Ala Leu Ile Gln Leu Lys
        835                 840                 845

Thr Ser Val Ala Leu Thr Thr Arg Val Gln Pro Ile Cys Leu Pro Thr
    850                 855                 860

Asp Leu Thr Thr Arg Glu Asn Leu Lys Glu Gly Ala Leu Ala Val Val
865                 870                 875                 880

Thr Gly Trp Gly Leu Asn Glu Asn Asn Thr Tyr Ser Glu Met Ile Gln
                885                 890                 895

Gln Ala Val Leu Pro Val Val Ala Ala Ser Thr Cys Glu Gln Gly Tyr
            900                 905                 910

Gln Asp Ser Gly Leu Pro Leu Thr Val Thr Glu Asn Met Phe Cys Ala
        915                 920                 925

Gly Tyr Lys Gln Gly Arg Tyr Asp Ala Cys Ser Gly Asp Ser Gly Gly
    930                 935                 940

Pro Leu Val Phe Ala Asp Asp Ser Arg Thr Asp Arg Arg Trp Val Leu
945                 950                 955                 960

Glu Gly Ile Val Ser Trp Gly Ser Pro Asn Gly Cys Gly Lys Ser Asn
                965                 970                 975

Gln Tyr Gly Gly Phe Thr Lys Val Asn Val Phe Leu Ser Trp Ile Arg
            980                 985                 990

Gln Phe Ile
        995

<210> SEQ ID NO 3
<211> LENGTH: 1020
<212> TYPE: PRT
<213> ORGANISM: Limulus polyphemus

<400> SEQUENCE: 3

Met Val Leu Ala Ser Phe Leu Val Ser Gly Leu Val Leu Gly Leu Leu
1               5                   10                  15

Ala Gln Lys Met Arg Pro Val Gln Ser Arg Gly Val Asp Leu Gly Leu
            20                  25                  30

Cys Asp Asp Thr Arg Phe Glu Cys Lys Cys Gly Asp Pro Gly Tyr Val
        35                  40                  45

Phe Asn Val Pro Ala Lys Gln Cys Thr Tyr Phe Tyr Arg Trp Arg Pro
    50                  55                  60

Tyr Cys Lys Pro Cys Asp Lys Leu Glu Ala Lys Asp Val Cys Pro Lys
65                  70                  75                  80

Tyr Lys Arg Cys Gln Glu Cys Arg Ala Gly Leu Asp Ser Cys Val Ser
                85                  90                  95

Cys Pro Pro Asn Lys Tyr Gly Thr Trp Cys Ser Gly Glu Cys Gln Cys
```

```
            100                 105                 110
Lys Asn Gly Gly Ile Cys Asp Gln Arg Thr Gly Ala Cys Thr Cys Arg
            115                 120                 125

Asp Arg Tyr Glu Gly Val His Cys Glu Ile Leu Gln Gly Cys Pro Leu
            130                 135                 140

Leu Gln Ser Asp Pro Gln Val Gln Glu Val Lys Asn Pro Pro Asn Asp
145                 150                 155                 160

Pro Gln Thr Ile Asp Tyr Ser Cys Ser Pro Gly Phe Lys Leu Lys Gly
                165                 170                 175

Val Ala Arg Ile Thr Cys Leu Pro Asn Gly Gln Trp Ser Ser Phe Pro
            180                 185                 190

Pro Lys Cys Ile Arg Glu Cys Ser Met Val Ser Ser Leu Glu His Gly
            195                 200                 205

Lys Val Asn Ser Pro Ser Ala Asp Leu Ile Glu Gly Ala Thr Leu Arg
            210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Ser Gly Gln Ile Pro Gln Cys Gln Lys
                245                 250                 255

Leu Val Phe Cys Pro Asp Leu Asp Pro Val Ser His Ala Glu His Gln
            260                 265                 270

Val Lys Ile Gly Leu Glu Gln Lys Tyr Gly Gln Phe Pro Gln Gly Thr
            275                 280                 285

Glu Val Thr Tyr Thr Cys Thr Gly Asn Tyr Phe Leu Met Gly Leu Asp
            290                 295                 300

Thr Leu Lys Cys Asn Pro Asp Gly Ser Trp Ser Gly Thr Gln Pro Ser
305                 310                 315                 320

Cys Val Lys Val Ala Asp Arg Glu Val Asn Cys Asp Ser Lys Ala Val
                325                 330                 335

Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
            355                 360                 365

Glu Leu Ser Ser Val Cys Arg Ala Ala Ile His Ala Gly Lys Val Pro
            370                 375                 380

Asn Ser Gly Gly Ala Val His Val Val Asn Asn Gly Pro Tyr Ser Asp
385                 390                 395                 400

Phe Leu Ala Ser Asp Leu Asn Gly Ile Lys Ser Asp Glu Leu Lys Ser
                405                 410                 415

Leu Ala Gln Ser Phe Arg Phe Asp Tyr Val Ser Ser Ser Thr Ala Gly
            420                 425                 430

Arg Lys Ser Gly Cys Pro Asp Gly Trp Phe Glu Ile Glu Glu Asn Cys
            435                 440                 445

Val Tyr Val Thr Ser Lys Gln Arg Ala Trp Glu Arg Ala Gln Gly Val
            450                 455                 460

Cys Thr Asn Met Ala Ala Arg Leu Ala Val Leu Asp Lys Asp Val Ile
465                 470                 475                 480

Pro Ser Ser Leu Thr Glu Thr Leu Arg Gly Lys Gly Leu Ala Thr Thr
                485                 490                 495

Trp Ile Gly Leu His Arg Leu Asp Ala Asp Asn His Phe Ile Trp Glu
            500                 505                 510

Leu Met Asp Arg Ser Ser Val Ala Leu Asn Asp Ser Leu Thr Phe Trp
            515                 520                 525
```

```
Ala Pro Gly Glu Pro Gly Asn Glu Thr Asn Cys Val Tyr Leu Asp Ile
    530             535             540

Gln Asp Gln Leu Gln Pro Val Trp Lys Thr Lys Ser Cys Phe Gln Pro
545             550             555             560

Ser Ser Phe Val Cys Met Met Asp Leu Ser Asp Lys Asn Lys Ala Lys
            565             570             575

Cys Lys Asp Pro Gly Pro Leu Glu Asn Gly His Ala Lys Leu His Gly
        580             585             590

Gln Ser Ile Asp Gly Phe Tyr Ala Gly Ser Ser Val Arg Tyr Ser Cys
    595             600             605

Glu Val Leu His Tyr Leu Ser Gly Thr Glu Thr Val Ser Cys Thr Ser
610             615             620

Asn Gly Thr Trp Ser Ala Pro Lys Pro Arg Cys Ile Lys Val Ile Thr
625             630             635             640

Cys Gln Thr Pro Pro Val Pro Ser Tyr Gly Ser Val Asp Ile Lys Pro
            645             650             655

Pro Ser Arg Thr Asn Ser Ile Ser Arg Val Gly Ser Pro Phe Leu Arg
        660             665             670

Leu Pro Arg Leu Pro Leu Pro Leu Ala Arg Ala Ala Gly Pro Pro Pro
    675             680             685

Lys Pro Arg Ser Ala Pro Pro Ser Thr Val Asp Leu Ser Ser Lys Val
690             695             700

Lys Leu Pro Glu Gly His Tyr Arg Val Gly Ser Gln Ala Ile Tyr Thr
705             710             715             720

Cys Glu Ser Arg Tyr Tyr Glu Leu Leu Gly Ser Gln Arg Arg Cys
            725             730             735

Asp Ser Asn Gly Lys Trp Ser Gly Arg Pro Ala Ser Cys Ile Pro Val
        740             745             750

Cys Gly Arg Ser Asp Ser Pro Arg Ser Pro Phe Ile Val Asn Gly Asn
    755             760             765

Ser Thr Glu Ile Gly Gln Trp Pro Trp Gln Ala Gly Ile Ser Arg Trp
770             775             780

Leu Ala Asp His Asn Met Trp Phe Leu Gln Cys Gly Gly Ala Leu Leu
785             790             795             800

Asn Glu Lys Trp Ile Ile Thr Ala Ala His Cys Val Thr Tyr Ser Ala
            805             810             815

Thr Ala Glu Ile Ile Asp Pro Ser Gln Phe Lys Phe Tyr Leu Gly Lys
        820             825             830

Tyr Tyr Arg Asp Asp Ser Lys Asp Asp Asp Tyr Val Gln Val Arg Glu
    835             840             845

Ala Ile Glu Ile His Val Asn Pro Asn Tyr Asp Pro Gly Asn Leu Asn
850             855             860

Phe Asp Ile Ala Leu Ile Gln Leu Lys Thr Ser Val Ala Leu Thr Thr
865             870             875             880

Arg Val Gln Pro Ile Cys Leu Pro Thr Asp Leu Thr Thr Arg Glu Asn
            885             890             895

Leu Lys Glu Gly Ala Leu Ala Val Val Thr Gly Trp Gly Leu Asn Glu
        900             905             910

Asn Asn Thr Tyr Ser Glu Met Ile Gln Gln Ala Val Leu Pro Val Val
    915             920             925

Ala Ala Ser Thr Cys Glu Gln Gly Tyr Gln Asp Ser Gly Leu Pro Leu
930             935             940
```

Thr Val Thr Glu Asn Met Phe Cys Ala Gly Tyr Lys Gln Gly Arg Tyr
945                 950                 955                 960

Asp Ala Cys Ser Gly Asp Ser Gly Pro Leu Val Phe Ala Asp Asp
            965                 970                 975

Ser Arg Thr Asp Arg Arg Trp Val Leu Glu Gly Ile Val Ser Trp Gly
        980                 985                 990

Ser Pro Asn Gly Cys Gly Lys Ser Asn Gln Tyr Gly Gly Phe Thr Lys
    995                 1000                1005

Val Asn Val Phe Leu Ser Trp Ile Arg Gln Phe Ile
    1010                1015                1020

<210> SEQ ID NO 4
<211> LENGTH: 1203
<212> TYPE: DNA
<213> ORGANISM: Limulus polyphemus

<400> SEQUENCE: 4

```
atggcctgga tctgtgtcat tacccttttc gctctcgcct cgtctactct gtccaacaaa      60
gtgtcgaggg tcggaatcat cttccccaag actcagaacg acaacaagca gtgcacggct     120
aagggtggac tcaagggcag ctgcaaatcc ctcactgact gccccgccgt gctggcgacc     180
cttaaggaca gcttccctgt cgtgtgtagc tggaatggcc ggttccaacc gattgtgtgc     240
tgtccggacg ccgccgcccc ttccgtgaca actaccgtga ccactatcgt gccgaccaag     300
gaaactaaga tccctagact gcatatcccg ggctgcggga acggaaagt caacgtggac      360
atcaccacca tcggacggtc cggtagcccg atcctgccgc ccattagcac gtcacaggac     420
ctgaaggggg gccgcggaat cattgccggc ggagtggaag cgaagattgg ggcgtggccc     480
tggatggccg cagtgttcgt gaagaacttt ggcattggaa gattccactg cgcgggatcc     540
atcatttcgt ccaagtacat tctgtccgcc gcccacgcct cctgatcgg cggccgcaag      600
ctgaccccca cccgcttggc cgtgcgcgtg ggcggacact acgtcaagat gggccaagag     660
taccacgtgg aagatgtcat catccaccct gactacgtgg aacgggagaa ctacaacgac     720
atcgctatca tcgtgctgaa ggaggagctg aacttcaccg acctcgtgcg cccaatctgc     780
ctgccggatc cagaggccgt gaccgattca ctcaagggtc ggagagtgac cgtcgccggt     840
tgggggacc tcgacttcgc ggggccccgg tcccaagtgc tgcgggaggt gtccatacca     900
gtggtgccta ttggcgattg caacaaggca atcagaagc tcaacacctt ggctctgaag     960
aacggaatta ccaagaagtt catctgcgcc gggctggaag aagggggaaa ggacgcgtgc    1020
cagggcgatt cgggtggacc cctgatgctg gtcaacaact catcgtggat cgtgaccgga    1080
gtggtgtcct tcggacataa gtgcgccgaa gaagggtttc cgggagtcta caccagggtg    1140
gtgtcctacc tggagtggat cgcaaaggtc accaattcct tggatcagac cgtcactaac    1200
taa                                                                  1203
```

<210> SEQ ID NO 5
<211> LENGTH: 375
<212> TYPE: PRT
<213> ORGANISM: Limulus polyphemus

<400> SEQUENCE: 5

Ile Ile Phe Pro Lys Thr Gln Asn Asp Asn Lys Gln Cys Thr Ala Lys
1               5                   10                  15

Gly Gly Leu Lys Gly Ser Cys Lys Ser Leu Thr Asp Cys Pro Ala Val
            20                  25                  30

```
Leu Ala Thr Leu Lys Asp Ser Phe Pro Val Val Cys Ser Trp Asn Gly
         35                  40                  45

Arg Phe Gln Pro Ile Val Cys Cys Pro Asp Ala Ala Pro Ser Val
 50                  55                  60

Thr Thr Thr Val Thr Thr Ile Val Pro Thr Lys Glu Thr Lys Ile Pro
 65                  70                  75                  80

Arg Leu His Ile Pro Gly Cys Gly Lys Arg Lys Val Asn Val Asp Ile
                 85                  90                  95

Thr Thr Ile Gly Arg Ser Gly Ser Pro Ile Leu Pro Pro Ile Ser Thr
            100                 105                 110

Ser Gln Asp Leu Lys Gly Gly Arg Gly Ile Ile Ala Gly Gly Val Glu
        115                 120                 125

Ala Lys Ile Gly Ala Trp Pro Trp Met Ala Ala Val Phe Val Lys Asn
130                 135                 140

Phe Gly Ile Gly Arg Phe His Cys Ala Gly Ser Ile Ile Ser Ser Lys
145                 150                 155                 160

Tyr Ile Leu Ser Ala Ala His Ala Phe Leu Ile Gly Gly Arg Lys Leu
                165                 170                 175

Thr Pro Thr Arg Leu Ala Val Arg Val Gly Gly His Tyr Val Lys Met
            180                 185                 190

Gly Gln Glu Tyr His Val Glu Asp Val Ile Ile His Pro Asp Tyr Val
        195                 200                 205

Glu Arg Glu Asn Tyr Asn Asp Ile Ala Ile Ile Val Leu Lys Glu Glu
    210                 215                 220

Leu Asn Phe Thr Asp Leu Val Arg Pro Ile Cys Leu Pro Asp Pro Glu
225                 230                 235                 240

Ala Val Thr Asp Ser Leu Lys Gly Arg Arg Val Thr Val Ala Gly Trp
                245                 250                 255

Gly Asp Leu Asp Phe Ala Gly Pro Arg Ser Gln Val Leu Arg Glu Val
            260                 265                 270

Ser Ile Pro Val Val Pro Ile Gly Asp Cys Asn Lys Ala Tyr Gln Lys
        275                 280                 285

Leu Asn Thr Leu Ala Leu Lys Asn Gly Ile Thr Lys Lys Phe Ile Cys
    290                 295                 300

Ala Gly Leu Glu Glu Gly Gly Lys Asp Ala Cys Gln Gly Asp Ser Gly
305                 310                 315                 320

Gly Pro Leu Met Leu Val Asn Asn Ser Ser Trp Ile Val Thr Gly Val
                325                 330                 335

Val Ser Phe Gly His Lys Cys Ala Glu Glu Gly Phe Pro Gly Val Tyr
            340                 345                 350

Thr Arg Val Val Ser Tyr Leu Glu Trp Ile Ala Lys Val Thr Asn Ser
        355                 360                 365

Leu Asp Gln Thr Val Thr Asn
    370                 375

<210> SEQ ID NO 6
<211> LENGTH: 400
<212> TYPE: PRT
<213> ORGANISM: Limulus polyphemus

<400> SEQUENCE: 6

Met Ala Trp Ile Cys Val Ile Thr Leu Phe Ala Leu Ala Ser Ser Thr
1               5                   10                  15

Leu Ser Asn Lys Val Ser Arg Val Gly Ile Ile Phe Pro Lys Thr Gln
                20                  25                  30
```

Asn Asp Asn Lys Gln Cys Thr Ala Lys Gly Gly Leu Lys Gly Ser Cys
            35                  40                  45

Lys Ser Leu Thr Asp Cys Pro Ala Val Leu Ala Thr Leu Lys Asp Ser
        50                  55                  60

Phe Pro Val Val Cys Ser Trp Asn Gly Arg Phe Gln Pro Ile Val Cys
65                  70                  75                  80

Cys Pro Asp Ala Ala Pro Ser Val Thr Thr Val Thr Thr Ile
                85                  90                  95

Val Pro Thr Lys Glu Thr Lys Ile Pro Arg Leu His Ile Pro Gly Cys
                100                 105                 110

Gly Lys Arg Lys Val Asn Val Asp Ile Thr Thr Ile Gly Arg Ser Gly
            115                 120                 125

Ser Pro Ile Leu Pro Pro Ile Ser Thr Ser Gln Asp Leu Lys Gly Gly
            130                 135                 140

Arg Gly Ile Ile Ala Gly Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Ser Lys Tyr Ile Leu Ser Ala Ala His
            180                 185                 190

Ala Phe Leu Ile Gly Gly Arg Lys Leu Thr Pro Thr Arg Leu Ala Val
        195                 200                 205

Arg Val Gly Gly His Tyr Val Lys Met Gly Gln Glu Tyr His Val Glu
210                 215                 220

Asp Val Ile Ile His Pro Asp Tyr Val Glu Arg Glu Asn Tyr Asn Asp
225                 230                 235                 240

Ile Ala Ile Ile Val Leu Lys Glu Glu Leu Asn Phe Thr Asp Leu Val
                245                 250                 255

Arg Pro Ile Cys Leu Pro Asp Pro Glu Ala Val Thr Asp Ser Leu Lys
            260                 265                 270

Gly Arg Arg Val Thr Val Ala Gly Trp Gly Asp Leu Asp Phe Ala Gly
            275                 280                 285

Pro Arg Ser Gln Val Leu Arg Glu Val Ser Ile Pro Val Val Pro Ile
        290                 295                 300

Gly Asp Cys Asn Lys Ala Tyr Gln Lys Leu Asn Thr Leu Ala Leu Lys
305                 310                 315                 320

Asn Gly Ile Thr Lys Lys Phe Ile Cys Ala Gly Leu Glu Glu Gly Gly
                325                 330                 335

Lys Asp Ala Cys Gln Gly Asp Ser Gly Gly Pro Leu Met Leu Val Asn
            340                 345                 350

Asn Ser Trp Ile Val Thr Gly Val Val Ser Phe Gly His Lys Cys
        355                 360                 365

Ala Glu Glu Gly Phe Pro Gly Val Tyr Thr Arg Val Val Ser Tyr Leu
    370                 375                 380

Glu Trp Ile Ala Lys Val Thr Asn Ser Leu Asp Gln Thr Val Thr Asn
385                 390                 395                 400

<210> SEQ ID NO 7
<211> LENGTH: 1149
<212> TYPE: DNA
<213> ORGANISM: Limulus polyphemus

<400> SEQUENCE: 7
atgggaatct tgccctcgcc cggaatgcct gccctgctta gcctcgtgtc actcctgtcc      60

```
gtcctgctca tgggctgcgt ggcctcctca ctgggacgcc agcggagaca gttcgtgttc    120
ccggatgacg aagagtcctg tagcaaccgg tttaccaacg acgggatctg caaggacgtg    180
ctgaactgcc gcgatctgct gcagaagaat gactacaacc tcttgaagga atccatctgc    240
ggcttcgaag ggatcacccc taaagtctgc tgtccaaagc aatccattgt gaaccccatc    300
accgaagccc cgcctaagac caccactact gagaggcctc cgatccggat cccctccaac    360
ctcccgaagc agtgcggaaa tcggaacatc actaccacta ggatcatcgg cggacaggaa    420
gccactccgg gagcctggcc gtggatggca gccgtgtaca ttaagcaggg ggggattcgg    480
tccgtgcagt gcggtggcgc ccttgtgacc aacagacacg tgatcaccgc ctcacactgc    540
gtcgtgaatt ccctgggtac cgatgtgatg agggctgatg tgttctccgt gcggctggga    600
gaacataacc tgtacagcac taacgactcg tcagacccaa tcgacttcgc cgtgacgagc    660
gtgaagcacc atgaaaactt cgtgctggcc acctacctca cgacatcgc gatcctgaag    720 ctgaacgaca ctgtcaccct cacacacaag attaagccga tttgcctccc ttacgagtcc    780
ctgcgctatg aggacctcgc tatgcgcaac cccttcgtgg ccggatgggg cactaccgcg    840
ttcaacggac cgagcagcgc tgtcctgaga gaagtgcaac tcccaatctg ggtcacgag    900 ccgtgccgcc aagcgtacga gaaagacctg aacatcacca acgtgtatat gtgcgcgggc    960
tacgccgacg gtgaaagga cgcatgccag ggcgattctg gcggcccat gatgctgcct   1020 gacaagtccg ggaacttcta cctggtcgga atcgtgtcgt tcggaaagaa atgcgccctg   1080
cccggctttc ccggagtgta caccaaggtc accgaatttt tggattggat tgccgtgaac   1140
atggtctaa                                                           1149

<210> SEQ ID NO 8
<211> LENGTH: 354
<212> TYPE: PRT
<213> ORGANISM: Limulus polyphemus

<400> SEQUENCE: 8

Ser Ser Leu Gly Arg Gln Arg Arg Gln Phe Val Phe Pro Asp Asp Glu
1               5                   10                  15

Glu Ser Cys Ser Asn Arg Phe Thr Asn Asp Gly Ile Cys Lys Asp Val
                20                  25                  30

Leu Asn Cys Arg Asp Leu Leu Gln Lys Asn Asp Tyr Asn Leu Leu Lys
            35                  40                  45

Glu Ser Ile Cys Gly Phe Glu Gly Ile Thr Pro Lys Val Cys Cys Pro
        50                  55                  60

Lys Gln Ser Ile Val Asn Pro Ile Thr Glu Ala Pro Pro Lys Thr Thr
65                  70                  75                  80

Thr Thr Glu Arg Pro Pro Ile Arg Ile Pro Ser Asn Leu Pro Lys Gln
                85                  90                  95

Cys Gly Asn Arg Asn Ile Thr Thr Thr Arg Ile Ile Gly Gly Gln Glu
            100                 105                 110

Ala Thr Pro Gly Ala Trp Pro Trp Met Ala Ala Val Tyr Ile Lys Gln
        115                 120                 125

Gly Gly Ile Arg Ser Val Gln Cys Gly Gly Ala Leu Val Thr Asn Arg
    130                 135                 140

His Val Ile Thr Ala Ser His Cys Val Val Asn Ser Leu Gly Thr Asp
145                 150                 155                 160

Val Met Arg Ala Asp Val Phe Ser Val Arg Leu Gly Glu His Asn Leu
                165                 170                 175
```

```
Tyr Ser Thr Asn Asp Ser Ser Asp Pro Ile Asp Phe Ala Val Thr Ser
            180                 185                 190

Val Lys His His Glu Asn Phe Val Leu Ala Thr Tyr Leu Asn Asp Ile
            195                 200                 205

Ala Ile Leu Lys Leu Asn Asp Thr Val Thr Phe Thr His Lys Ile Lys
210                 215                 220

Pro Ile Cys Leu Pro Tyr Glu Ser Leu Arg Tyr Glu Asp Leu Ala Met
225                 230                 235                 240

Arg Asn Pro Phe Val Ala Gly Trp Gly Thr Thr Ala Phe Asn Gly Pro
                245                 250                 255

Ser Ser Ala Val Leu Arg Glu Val Gln Leu Pro Ile Trp Gly His Glu
            260                 265                 270

Pro Cys Arg Gln Ala Tyr Glu Lys Asp Leu Asn Ile Thr Asn Val Tyr
            275                 280                 285

Met Cys Ala Gly Tyr Ala Asp Gly Gly Lys Asp Ala Cys Gln Gly Asp
            290                 295                 300

Ser Gly Gly Pro Met Met Leu Pro Asp Lys Ser Gly Asn Phe Tyr Leu
305                 310                 315                 320

Val Gly Ile Val Ser Phe Gly Lys Lys Cys Ala Leu Pro Gly Phe Pro
                325                 330                 335

Gly Val Tyr Thr Lys Val Thr Glu Phe Leu Asp Trp Ile Ala Val Asn
                340                 345                 350

Met Val

<210> SEQ ID NO 9
<211> LENGTH: 382
<212> TYPE: PRT
<213> ORGANISM: Limulus polyphemus

<400> SEQUENCE: 9

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Ser Ser Leu Gly
            20                  25                  30

Arg Gln Arg Arg Gln Phe Val Phe Pro Asp Asp Glu Glu Ser Cys Ser
        35                  40                  45

Asn Arg Phe Thr Asn Asp Gly Ile Cys Lys Asp Val Leu Asn Cys Arg
50                  55                  60

Asp Leu Leu Gln Lys Asn Asp Tyr Asn Leu Leu Lys Glu Ser Ile Cys
65                  70                  75                  80

Gly Phe Glu Gly Ile Thr Pro Lys Val Cys Cys Pro Lys Gln Ser Ile
                85                  90                  95

Val Asn Pro Ile Thr Glu Ala Pro Pro Lys Thr Thr Thr Glu Arg
            100                 105                 110

Pro Pro Ile Arg Ile Pro Ser Asn Leu Pro Lys Gln Cys Gly Asn Arg
            115                 120                 125

Asn Ile Thr Thr Thr Arg Ile Ile Gly Gly Gln Glu Ala Thr Pro Gly
130                 135                 140

Ala Trp Pro Trp Met Ala Ala Val Tyr Ile Lys Gln Gly Gly Ile Arg
145                 150                 155                 160

Ser Val Gln Cys Gly Gly Ala Leu Val Thr Asn Arg His Val Ile Thr
                165                 170                 175

Ala Ser His Cys Val Val Asn Ser Leu Gly Thr Asp Val Met Arg Ala
            180                 185                 190
```

```
Asp Val Phe Ser Val Arg Leu Gly Glu His Asn Leu Tyr Ser Thr Asn
        195                 200                 205

Asp Ser Ser Asp Pro Ile Asp Phe Ala Val Thr Ser Val Lys His His
    210                 215                 220

Glu Asn Phe Val Leu Ala Thr Tyr Leu Asn Asp Ile Ala Ile Leu Lys
225                 230                 235                 240

Leu Asn Asp Thr Val Thr Phe Thr His Lys Ile Lys Pro Ile Cys Leu
                245                 250                 255

Pro Tyr Glu Ser Leu Arg Tyr Glu Asp Leu Ala Met Arg Asn Pro Phe
            260                 265                 270

Val Ala Gly Trp Gly Thr Thr Ala Phe Asn Gly Pro Ser Ser Ala Val
        275                 280                 285

Leu Arg Glu Val Gln Leu Pro Ile Trp Gly His Glu Pro Cys Arg Gln
    290                 295                 300

Ala Tyr Glu Lys Asp Leu Asn Ile Thr Asn Val Tyr Met Cys Ala Gly
305                 310                 315                 320

Tyr Ala Asp Gly Gly Lys Asp Ala Cys Gln Gly Asp Ser Gly Gly Pro
                325                 330                 335

Met Met Leu Pro Asp Lys Ser Gly Asn Phe Tyr Leu Val Gly Ile Val
            340                 345                 350

Ser Phe Gly Lys Lys Cys Ala Leu Pro Gly Phe Pro Gly Val Tyr Thr
        355                 360                 365

Lys Val Thr Glu Phe Leu Asp Trp Ile Ala Val Asn Met Val
    370                 375                 380

<210> SEQ ID NO 10
<211> LENGTH: 3051
<212> TYPE: DNA
<213> ORGANISM: Tachypleus tridentatus

<400> SEQUENCE: 10
atgaagttcc tcgtcaacgt cgccctcgtg tttatggtgg tgtatattag ctacatctat      60
gctcgtggcg tcgatctggg cctgtgcgat gagacccgct tcgaatgtaa gtgcggcgac     120
cccggctatg tgttcaacgt ccccatgaag cagtgcacct acttctaccg ctggcgcccc     180
tactgtaagc cttgcgatga cctggaagct aaagatattt gccctaagta taagcgctgc     240
caagaatgta aggctggtct ggattcctgc gtcacctgtc cccctaacaa gtatggcacc     300
tggtgttccg gtaatgcca gtgcaaaaac ggcggcatct gcgatcagcg tactggcgct     360
tgcacctgcc gtgatcgcta cgagggcgcc cactgtgaaa ttctgaaagg ctgtcctctg     420
ctgccttccg atagccaagt gcaggaggtg cgtaaccccc tgacaacccc tcagaccatc     480
gattatagct gctccccggg cttcaagctg aagggcgtgg cccgtattag ctgtctgccc     540
aacggtcagt ggagctccct tccccccaag tgcatccgtg aatgtgccaa ggtctcctcc     600
cccgaacacg gcaaggtcaa cgctcccctc ggcaacatga tcgaaggcgc caccctccgt     660
ttttcctgcg actccccctta ctacctcatc ggccaggaga ccctgacttg tcagggcaat     720
ggccagtgga gcggtcaaat ccctcagtgc aagaagctgg tgttctgtcc tgacctcgat     780
cccgtgaacc acgctgagca ccaagtgaag atcggcgtgg aacaaaagta cggtcagttc     840
cctcagggca ctgaggtcac ttacacttgc tccggcaact acttcctgat gggcttcaac     900
accctgaaat gtaaccccga cggttcctgg tccggttccc agccctcctg cgtgaaagtc     960
gctgaccgtg aagtcgactg tgacagcaaa gccgtggact cctggacgga cgtgggcgag    1020
```

```
cctgtgcgta ttcactgtcc cgctggctgt agcctgactg ccggtaccgt gtggggtact    1080
gctatctacc acgagctctc cagcgtgtgc cgcgctgcta tccacgctgg caagctgcct    1140
aacagcggcg gtgctgtcca cgtggtgaac aacggtccct actccgactt cctcggtagc    1200
gacctgaacg gtatcaaaag cgaggaactg aagtccctgg cccgtagctt tcgcttcgac    1260
tacgtgtcct cctccaccgc tggccgtagc ggctgtcctg atggctggtt tgaggtggaa    1320
gagaattgtg tgtacgtgac ctccaagcag cgtgcttggg agcgtgctca gggtgtctgt    1380
accaatatgg ccgcccgtct ggctgtcctc gataaggatc tcatcccttc ctccctcacc    1440
gagactctgc gcggtaaggg cctgaccact acctggatcg gtctccaccg cctggacgct    1500
gagaagcctt tcgtctggga gctcatggac cgcagcaacg tggtgctgaa cgacaacctg    1560
accttctggg ccagcggcga gcctggcaat gaaaccaact gcgtgtacct ggacatccgt    1620
gatcagctcc agcccgtgtg gaagaccaag agctgcttcc agccctccag ctttgcttgc    1680
atgatggatc tctccgaccg caacaaggct aaatgtgatg atcccggccc cctggagaac    1740
ggccatgcca ctctgcatgg ccagagcatc gacggtttct acgctggttc ctccatccgc    1800
tactcctgcg aagtgctcca ctacctgtcc ggcaccgaga ccgtgacctg tactaccaac    1860
ggtacttgga gcgctcctaa accccgctgt atcaaggtga ttacctgtca gaaccctcct    1920
gtccccagct acggctccgt ggaaatcaag ccccccagcc gtactaatag catcagccgt    1980
gtcggttccc ctttcctgcg tctgcctcgt ctgcccctgc ctctcgctcg cgctgctaag    2040
cctcccccta gccccgttc cagccagcct agcactgtgg atctcgctag caaagtgaaa    2100 ctcccccgagg tcactatcg tgtgggctcc cgcgccattt acacctgcga gagccgctac    2160
tacgagctcc tgggcagcca gggtcgtcgt tgcgacagca acggtaactg gagcggtcgc    2220
cctgccagct gcattcccgt gtgcggtcgc agcgactccc ctcgcagccc tttcatctgg    2280
aacggcaaca gcaccgagat cggtcagtgg ccctggcaag ctggcattag ccgctggctc    2340
gctgatcaca acatgtggtt cctccaatgt ggcggcagcc tgctgaacga aagtggatc    2400 gtgactgccg ctcactgcgt gacctacagc gccaccgctg agatcatcga ccctcccaa    2460 tttaagatct acctcggcaa gtactaccgc gacgatagcc gcgacgacga ttatgtgcaa    2520
gtccgcgaag ctctcgaaat tcacgtgaac cctaactacg atcccggtaa cctgaacttc    2580
gacattgccc tgatccagct gaagacccct gtgaccctca ccactcgcgt ccagcctatc    2640
tgcctcccca ccgacattac cactcgcgaa catctgaaag aaggtaccct ggccgtcgtg    2700
accggctggg gcctcaacga aaacaacact tacagcgaga tgatccagca ggctgtgctg    2760
cctgtcgtgg ctgctagcac ctgtgaggaa ggctacaaag aggccgatct cccctgacc    2820 gtcaccgaga acatgttttg cgctggttac aaaaagggcc gctacgacgc tgcagcggt    2880 gatagcggtg ccctctcgt gttcgccgat gattcccgta ccgaacgtcg ctgggtgctc    2940
gagggcattg tgtcctgggg tagcccttcc ggctgtggca aggctaacca atacggcggc    3000
ttcaccaagg tgaacgtgtt cctgtcctgg attcgtcagt tcatctaatg a             3051
```

<210> SEQ ID NO 11
<211> LENGTH: 994
<212> TYPE: PRT
<213> ORGANISM: Tachypleus tridentatus

<400> SEQUENCE: 11

Arg Gly Val Asp Leu Gly Leu Cys Asp Glu Thr Arg Phe Glu Cys Lys
1               5                   10                  15

-continued

Cys Gly Asp Pro Gly Tyr Val Phe Asn Val Pro Met Lys Gln Cys Thr
              20                  25                  30

Tyr Phe Tyr Arg Trp Arg Pro Tyr Cys Lys Pro Cys Asp Asp Leu Glu
          35                  40                  45

Ala Lys Asp Ile Cys Pro Lys Tyr Lys Arg Cys Gln Glu Cys Lys Ala
        50                  55                  60

Gly Leu Asp Ser Cys Val Thr Cys Pro Pro Asn Lys Tyr Gly Thr Trp
65                  70                  75                  80

Cys Ser Gly Glu Cys Gln Cys Lys Asn Gly Ile Cys Asp Gln Arg
              85                  90                  95

Thr Gly Ala Cys Thr Cys Arg Asp Arg Tyr Glu Gly Ala His Cys Glu
            100                 105                 110

Ile Leu Lys Gly Cys Pro Leu Leu Pro Ser Asp Ser Gln Val Gln Glu
            115                 120                 125

Val Arg Asn Pro Pro Asp Asn Pro Gln Thr Ile Asp Tyr Ser Cys Ser
        130                 135                 140

Pro Gly Phe Lys Leu Lys Gly Val Ala Arg Ile Ser Cys Leu Pro Asn
145                 150                 155                 160

Gly Gln Trp Ser Ser Phe Pro Pro Lys Cys Ile Arg Glu Cys Ala Lys
            165                 170                 175

Val Ser Ser Pro Glu His Gly Lys Val Asn Ala Pro Ser Gly Asn Met
            180                 185                 190

Ile Glu Gly Ala Thr Leu Arg Phe Ser Cys Asp Ser Pro Tyr Tyr Leu
            195                 200                 205

Ile Gly Gln Glu Thr Leu Thr Cys Gln Gly Asn Gly Gln Trp Ser Gly
            210                 215                 220

Gln Ile Pro Gln Cys Lys Lys Leu Val Phe Cys Pro Asp Leu Asp Pro
225                 230                 235                 240

Val Asn His Ala Glu His Gln Val Lys Ile Gly Val Glu Gln Lys Tyr
                245                 250                 255

Gly Gln Phe Pro Gln Gly Thr Glu Val Thr Tyr Thr Cys Ser Gly Asn
            260                 265                 270

Tyr Phe Leu Met Gly Phe Asn Thr Leu Lys Cys Asn Pro Asp Gly Ser
        275                 280                 285

Trp Ser Gly Ser Gln Pro Ser Cys Val Lys Val Ala Asp Arg Glu Val
290                 295                 300

Asp Cys Asp Ser Lys Ala Val Asp Phe Leu Asp Asp Val Gly Glu Pro
305                 310                 315                 320

Val Arg Ile His Cys Pro Ala Gly Cys Ser Leu Thr Ala Gly Thr Val
            325                 330                 335

Trp Gly Thr Ala Ile Tyr His Glu Leu Ser Ser Val Cys Arg Ala Ala
            340                 345                 350

Ile His Ala Gly Lys Leu Pro Asn Ser Gly Gly Ala Val His Val Val
        355                 360                 365

Asn Asn Gly Pro Tyr Ser Asp Phe Leu Gly Ser Asp Leu Asn Gly Ile
370                 375                 380

Lys Ser Glu Glu Leu Lys Ser Leu Ala Arg Ser Phe Arg Phe Asp Tyr
385                 390                 395                 400

Val Ser Ser Ser Thr Ala Gly Arg Ser Gly Cys Pro Asp Gly Trp Phe
                405                 410                 415

Glu Val Glu Glu Asn Cys Val Tyr Val Thr Ser Lys Gln Arg Ala Trp
            420                 425                 430

Glu Arg Ala Gln Gly Val Cys Thr Asn Met Ala Ala Arg Leu Ala Val

```
                435                 440                 445
Leu Asp Lys Asp Leu Ile Pro Ser Ser Leu Thr Glu Thr Leu Arg Gly
450                 455                 460

Lys Gly Leu Thr Thr Thr Trp Ile Gly Leu His Arg Leu Asp Ala Glu
465                 470                 475                 480

Lys Pro Phe Val Trp Glu Leu Met Asp Arg Ser Asn Val Val Leu Asn
                485                 490                 495

Asp Asn Leu Thr Phe Trp Ala Ser Gly Glu Pro Gly Asn Glu Thr Asn
                500                 505                 510

Cys Val Tyr Leu Asp Ile Arg Asp Gln Leu Gln Pro Val Trp Lys Thr
                515                 520                 525

Lys Ser Cys Phe Gln Pro Ser Ser Phe Ala Cys Met Met Asp Leu Ser
530                 535                 540

Asp Arg Asn Lys Ala Lys Cys Asp Pro Gly Pro Leu Glu Asn Gly
545                 550                 555                 560

His Ala Thr Leu His Gly Gln Ser Ile Asp Gly Phe Tyr Ala Gly Ser
                565                 570                 575

Ser Ile Arg Tyr Ser Cys Glu Val Leu His Tyr Leu Ser Gly Thr Glu
                580                 585                 590

Thr Val Thr Cys Thr Thr Asn Gly Thr Trp Ser Ala Pro Lys Pro Arg
                595                 600                 605

Cys Ile Lys Val Ile Thr Cys Gln Asn Pro Pro Val Pro Ser Tyr Gly
610                 615                 620

Ser Val Glu Ile Lys Pro Pro Ser Arg Thr Asn Ser Ile Ser Arg Val
625                 630                 635                 640

Gly Ser Pro Phe Leu Arg Leu Pro Arg Leu Pro Leu Pro Leu Ala Arg
                645                 650                 655

Ala Ala Lys Pro Pro Lys Pro Arg Ser Ser Gln Pro Ser Thr Val
                660                 665                 670

Asp Leu Ala Ser Lys Val Lys Leu Pro Glu Gly His Tyr Arg Val Gly
                675                 680                 685

Ser Arg Ala Ile Tyr Thr Cys Glu Ser Arg Tyr Tyr Glu Leu Leu Gly
690                 695                 700

Ser Gln Gly Arg Arg Cys Asp Ser Asn Gly Asn Trp Ser Gly Arg Pro
705                 710                 715                 720

Ala Ser Cys Ile Pro Val Cys Gly Arg Ser Asp Ser Pro Arg Ser Pro
                725                 730                 735

Phe Ile Trp Asn Gly Asn Ser Thr Glu Ile Gly Gln Trp Pro Trp Gln
                740                 745                 750

Ala Gly Ile Ser Arg Trp Leu Ala Asp His Asn Met Trp Phe Leu Gln
                755                 760                 765

Cys Gly Gly Ser Leu Leu Asn Glu Lys Trp Ile Val Thr Ala Ala His
770                 775                 780

Cys Val Thr Tyr Ser Ala Thr Ala Glu Ile Ile Asp Pro Ser Gln Phe
785                 790                 795                 800

Lys Ile Tyr Leu Gly Lys Tyr Tyr Arg Asp Asp Ser Arg Asp Asp Asp
                805                 810                 815

Tyr Val Gln Val Arg Glu Ala Leu Glu Ile His Val Asn Pro Asn Tyr
                820                 825                 830

Asp Pro Gly Asn Leu Asn Phe Asp Ile Ala Leu Ile Gln Leu Lys Thr
                835                 840                 845

Pro Val Thr Leu Thr Thr Arg Val Gln Pro Ile Cys Leu Pro Thr Asp
850                 855                 860
```

```
Ile Thr Thr Arg Glu His Leu Lys Glu Gly Thr Leu Ala Val Val Thr
865                 870                 875                 880

Gly Trp Gly Leu Asn Glu Asn Asn Thr Tyr Ser Glu Met Ile Gln Gln
                885                 890                 895

Ala Val Leu Pro Val Val Ala Ala Ser Thr Cys Glu Glu Gly Tyr Lys
            900                 905                 910

Glu Ala Asp Leu Pro Leu Thr Val Thr Glu Asn Met Phe Cys Ala Gly
        915                 920                 925

Tyr Lys Lys Gly Arg Tyr Asp Ala Cys Ser Gly Asp Ser Gly Gly Pro
    930                 935                 940

Leu Val Phe Ala Asp Asp Ser Arg Thr Glu Arg Arg Trp Val Leu Glu
945                 950                 955                 960

Gly Ile Val Ser Trp Gly Ser Pro Ser Gly Cys Gly Lys Ala Asn Gln
                965                 970                 975

Tyr Gly Gly Phe Thr Lys Val Asn Val Phe Leu Ser Trp Ile Arg Gln
                980                 985                 990

Phe Ile

<210> SEQ ID NO 12
<211> LENGTH: 1015
<212> TYPE: PRT
<213> ORGANISM: Tachypleus tridentatus

<400> SEQUENCE: 12

Met Lys Phe Leu Val Asn Val Ala Leu Val Phe Met Val Val Tyr Ile
1               5                   10                  15

Ser Tyr Ile Tyr Ala Arg Gly Val Asp Leu Gly Leu Cys Asp Glu Thr
            20                  25                  30

Arg Phe Glu Cys Lys Cys Gly Asp Pro Gly Tyr Val Phe Asn Val Pro
        35                  40                  45

Met Lys Gln Cys Thr Tyr Phe Tyr Arg Trp Arg Pro Tyr Cys Lys Pro
    50                  55                  60

Cys Asp Asp Leu Glu Ala Lys Asp Ile Cys Pro Lys Tyr Lys Arg Cys
65                  70                  75                  80

Gln Glu Cys Lys Ala Gly Leu Asp Ser Cys Val Thr Cys Pro Pro Asn
                85                  90                  95

Lys Tyr Gly Thr Trp Cys Ser Gly Glu Cys Gln Cys Lys Asn Gly Gly
            100                 105                 110

Ile Cys Asp Gln Arg Thr Gly Ala Cys Thr Cys Arg Asp Arg Tyr Glu
        115                 120                 125

Gly Ala His Cys Glu Ile Leu Lys Gly Cys Pro Leu Leu Pro Ser Asp
    130                 135                 140

Ser Gln Val Gln Glu Val Arg Asn Pro Pro Asp Asn Pro Gln Thr Ile
145                 150                 155                 160

Asp Tyr Ser Cys Ser Pro Gly Phe Lys Leu Lys Gly Val Ala Arg Ile
                165                 170                 175

Ser Cys Leu Pro Asn Gly Gln Trp Ser Ser Phe Pro Pro Lys Cys Ile
            180                 185                 190

Arg Glu Cys Ala Lys Val Ser Ser Pro Glu His Gly Lys Val Asn Ala
        195                 200                 205

Pro Ser Gly Asn Met Ile Glu Gly Ala Thr Leu Arg Phe Ser Cys Asp
    210                 215                 220

Ser Pro Tyr Tyr Leu Ile Gly Gln Glu Thr Leu Thr Cys Gln Gly Asn
225                 230                 235                 240
```

-continued

```
Gly Gln Trp Ser Gly Gln Ile Pro Gln Cys Lys Lys Leu Val Phe Cys
                245                 250                 255

Pro Asp Leu Asp Pro Val Asn His Ala Glu His Gln Val Lys Ile Gly
                260                 265                 270

Val Glu Gln Lys Tyr Gly Gln Phe Pro Gln Gly Thr Glu Val Thr Tyr
                275                 280                 285

Thr Cys Ser Gly Asn Tyr Phe Leu Met Gly Phe Asn Thr Leu Lys Cys
                290                 295                 300

Asn Pro Asp Gly Ser Trp Ser Gly Ser Gln Pro Ser Cys Val Lys Val
305                 310                 315                 320

Ala Asp Arg Glu Val Asp Cys Asp Ser Lys Ala Val Asp Phe Leu Asp
                325                 330                 335

Asp Val Gly Glu Pro Val Arg Ile His Cys Pro Ala Gly Cys Ser Leu
                340                 345                 350

Thr Ala Gly Thr Val Trp Gly Thr Ala Ile Tyr His Glu Leu Ser Ser
                355                 360                 365

Val Cys Arg Ala Ala Ile His Ala Gly Lys Leu Pro Asn Ser Gly Gly
                370                 375                 380

Ala Val His Val Val Asn Asn Gly Pro Tyr Ser Asp Phe Leu Gly Ser
385                 390                 395                 400

Asp Leu Asn Gly Ile Lys Ser Glu Leu Lys Ser Leu Ala Arg Ser
                405                 410                 415

Phe Arg Phe Asp Tyr Val Ser Ser Ser Thr Ala Gly Arg Ser Gly Cys
                420                 425                 430

Pro Asp Gly Trp Phe Glu Val Glu Glu Asn Cys Val Tyr Val Thr Ser
                435                 440                 445

Lys Gln Arg Ala Trp Glu Arg Ala Gln Gly Val Cys Thr Asn Met Ala
450                 455                 460

Ala Arg Leu Ala Val Leu Asp Lys Asp Leu Ile Pro Ser Ser Leu Thr
465                 470                 475                 480

Glu Thr Leu Arg Gly Lys Gly Leu Thr Thr Thr Trp Ile Gly Leu His
                485                 490                 495

Arg Leu Asp Ala Glu Lys Pro Phe Val Trp Glu Leu Met Asp Arg Ser
                500                 505                 510

Asn Val Val Leu Asn Asp Asn Leu Thr Phe Trp Ala Ser Gly Glu Pro
                515                 520                 525

Gly Asn Glu Thr Asn Cys Val Tyr Leu Asp Ile Arg Asp Gln Leu Gln
                530                 535                 540

Pro Val Trp Lys Thr Lys Ser Cys Phe Gln Pro Ser Ser Phe Ala Cys
545                 550                 555                 560

Met Met Asp Leu Ser Asp Arg Asn Lys Ala Lys Cys Asp Asp Pro Gly
                565                 570                 575

Pro Leu Glu Asn Gly His Ala Thr Leu His Gly Gln Ser Ile Asp Gly
                580                 585                 590

Phe Tyr Ala Gly Ser Ser Ile Arg Tyr Ser Cys Glu Val Leu His Tyr
                595                 600                 605

Leu Ser Gly Thr Glu Thr Val Thr Cys Thr Thr Asn Gly Thr Trp Ser
                610                 615                 620

Ala Pro Lys Pro Arg Cys Ile Lys Val Ile Thr Cys Gln Asn Pro Pro
625                 630                 635                 640

Val Pro Ser Tyr Gly Ser Val Glu Ile Lys Pro Pro Ser Arg Thr Asn
                645                 650                 655
```

```
Ser Ile Ser Arg Val Gly Ser Pro Phe Leu Arg Leu Pro Arg Leu Pro
            660                 665                 670

Leu Pro Leu Ala Arg Ala Ala Lys Pro Pro Lys Pro Arg Ser Ser
        675                 680                 685

Gln Pro Ser Thr Val Asp Leu Ala Ser Lys Val Lys Leu Pro Glu Gly
    690                 695                 700

His Tyr Arg Val Gly Ser Arg Ala Ile Tyr Thr Cys Glu Ser Arg Tyr
705                 710                 715                 720

Tyr Glu Leu Leu Gly Ser Gln Gly Arg Arg Cys Asp Ser Asn Gly Asn
                725                 730                 735

Trp Ser Gly Arg Pro Ala Ser Cys Ile Pro Val Cys Gly Arg Ser Asp
            740                 745                 750

Ser Pro Arg Ser Pro Phe Ile Trp Asn Gly Asn Ser Thr Glu Ile Gly
        755                 760                 765

Gln Trp Pro Trp Gln Ala Gly Ile Ser Arg Trp Leu Ala Asp His Asn
    770                 775                 780

Met Trp Phe Leu Gln Cys Gly Gly Ser Leu Leu Asn Glu Lys Trp Ile
785                 790                 795                 800

Val Thr Ala Ala His Cys Val Thr Tyr Ser Ala Thr Ala Glu Ile Ile
                805                 810                 815

Asp Pro Ser Gln Phe Lys Ile Tyr Leu Gly Lys Tyr Tyr Arg Asp Asp
            820                 825                 830

Ser Arg Asp Asp Asp Tyr Val Gln Val Arg Glu Ala Leu Glu Ile His
        835                 840                 845

Val Asn Pro Asn Tyr Asp Pro Gly Asn Leu Asn Phe Asp Ile Ala Leu
    850                 855                 860

Ile Gln Leu Lys Thr Pro Val Thr Leu Thr Thr Arg Val Gln Pro Ile
865                 870                 875                 880

Cys Leu Pro Thr Asp Ile Thr Thr Arg Glu His Leu Lys Glu Gly Thr
                885                 890                 895

Leu Ala Val Val Thr Gly Trp Gly Leu Asn Glu Asn Asn Thr Tyr Ser
            900                 905                 910

Glu Met Ile Gln Gln Ala Val Leu Pro Val Val Ala Ala Ser Thr Cys
        915                 920                 925

Glu Glu Gly Tyr Lys Glu Ala Asp Leu Pro Leu Thr Val Thr Glu Asn
    930                 935                 940

Met Phe Cys Ala Gly Tyr Lys Lys Gly Arg Tyr Asp Ala Cys Ser Gly
945                 950                 955                 960

Asp Ser Gly Gly Pro Leu Val Phe Ala Asp Asp Ser Arg Thr Glu Arg
                965                 970                 975

Arg Trp Val Leu Glu Gly Ile Val Ser Trp Gly Ser Pro Ser Gly Cys
            980                 985                 990

Gly Lys Ala Asn Gln Tyr Gly Gly  Phe Thr Lys Val Asn  Val Phe Leu
        995                 1000                1005

Ser Trp  Ile Arg Gln Phe Ile
    1010                1015

<210> SEQ ID NO 13
<211> LENGTH: 1200
<212> TYPE: DNA
<213> ORGANISM: Tachypleus tridentatus

<400> SEQUENCE: 13
atggacatgc gcgtgcctgc ccaactgctc ggcctgctgc tgctgtggtt cccgggtagc      60
```

```
cgctgtgtgg gggtgctgtt ccccaagacc cggaacgaca acgaatgcac tgccagggt    120
ggattgaagg ggtcctgcaa gagcctgatc gactgcccgt cggtgcttgc caccctgaag    180
gactcctttc ctgtcgtgtg ctcctggaac ggcagattcc agccaattgt gtgctgtccg    240
gatgcaattg ccccccacc tgtgaccacc accgccgtga ccgtgatctc taccaaggaa     300
cccaagctgc ctcggctcca catcagcggt tgtgggaagc ggaaggtcaa gattgacatt    360
accactgtgg gacgctcagg atcaccgatt ctgccccga tctccacccc gcaaaactcc     420
actggtggca ggggcatcat tgccggtgga gtggaagcga agatcggagc ctggccttgg    480
atggcggcg tgtttgtgaa aaacttcgga atcgggcgt tccactgcgc tggttcgatc      540
atctccaaca agtacatcct gtccgccgca catgccttcc tgatcggagg ccggaagttg    600
accccccacga gactggccgt cagagtcgga gggcattaca tcaagcgcgg acaggaatac    660
cccgtgaagg acgtgataat ccacccccac tacgtggaaa aggagaacta caatgacatc    720
gccattatcg agctgaagga ggagctgaac tttaccgatc ttgtgaaccc catctgcctc    780
cctgaccccg agacagtgac cgacccactc aaagaccgca tcgtgactgc agctggatgg    840
ggcgatctgg acttcagcgg accgagaagc caggtcctgc gggaggtgtc aatcccggtg    900
gtgccagtcg acaaatgcga tcaggcctac gagaagctga cactccctc cctcaaaaac    960
gggatcacta acaacttcct gtgcgcggga cttgaagaag cggaaagga cgcctgtcag   1020
ggcgattccg gcgacctct gatgctcgtg aacaatactc ggtggattgt cgtcggcgtg    1080
gtgtccttcg acataagtg cgccgaggaa ggctaccctg cgtctattc ccgcgtggcc    1140
tcctacctgg actggattgc caaggtcacc aactcgctcg accatgccgt gactaactga   1200
```

<210> SEQ ID NO 14
<211> LENGTH: 377
<212> TYPE: PRT
<213> ORGANISM: Tachypleus tridentatus

<400> SEQUENCE: 14

Val Gly Val Leu Phe Pro Lys Thr Arg Asn Asp Asn Glu Cys Thr Ala
1               5                   10                  15

Arg Gly Gly Leu Lys Gly Ser Cys Lys Ser Leu Ile Asp Cys Pro Ser
            20                  25                  30

Val Leu Ala Thr Leu Lys Asp Ser Phe Pro Val Val Cys Ser Trp Asn
        35                  40                  45

Gly Arg Phe Gln Pro Ile Val Cys Cys Pro Asp Ala Ile Ala Pro Pro
    50                  55                  60

Pro Val Thr Thr Thr Ala Val Thr Val Ile Ser Thr Lys Glu Pro Lys
65                  70                  75                  80

Leu Pro Arg Leu His Ile Ser Gly Cys Gly Lys Arg Lys Val Lys Ile
                85                  90                  95

Asp Ile Thr Thr Val Gly Arg Ser Gly Ser Pro Ile Leu Pro Pro Ile
            100                 105                 110

Ser Thr Pro Gln Asn Ser Thr Gly Gly Arg Gly Ile Ile Ala Gly Gly
        115                 120                 125

Val Glu Ala Lys Ile Gly Ala Trp Pro Trp Met Ala Ala Val Phe Val
    130                 135                 140

Lys Asn Phe Gly Ile Gly Arg Phe His Cys Ala Gly Ser Ile Ile Ser
145                 150                 155                 160

Asn Lys Tyr Ile Leu Ser Ala Ala His Ala Phe Leu Ile Gly Gly Arg
                165                 170                 175

```
Lys Leu Thr Pro Thr Arg Leu Ala Val Arg Val Gly Gly His Tyr Ile
                180                 185                 190

Lys Arg Gly Gln Glu Tyr Pro Val Lys Asp Val Ile Ile His Pro His
            195                 200                 205

Tyr Val Glu Lys Glu Asn Tyr Asn Asp Ile Ala Ile Glu Leu Lys
        210                 215                 220

Glu Glu Leu Asn Phe Thr Asp Leu Val Asn Pro Ile Cys Leu Pro Asp
225                 230                 235                 240

Pro Glu Thr Val Thr Asp Pro Leu Lys Asp Arg Ile Val Thr Ala Ala
                245                 250                 255

Gly Trp Gly Asp Leu Asp Phe Ser Gly Pro Arg Ser Gln Val Leu Arg
                260                 265                 270

Glu Val Ser Ile Pro Val Val Pro Val Asp Lys Cys Asp Gln Ala Tyr
            275                 280                 285

Glu Lys Leu Asn Thr Pro Ser Leu Lys Asn Gly Ile Thr Asn Asn Phe
        290                 295                 300

Leu Cys Ala Gly Leu Glu Glu Gly Gly Lys Asp Ala Cys Gln Gly Asp
305                 310                 315                 320

Ser Gly Gly Pro Leu Met Leu Val Asn Asn Thr Arg Trp Ile Val Val
                325                 330                 335

Gly Val Val Ser Phe Gly His Lys Cys Ala Glu Glu Gly Tyr Pro Gly
                340                 345                 350

Val Tyr Ser Arg Val Ala Ser Tyr Leu Asp Trp Ile Ala Lys Val Thr
            355                 360                 365

Asn Ser Leu Asp His Ala Val Thr Asn
370                 375

<210> SEQ ID NO 15
<211> LENGTH: 399
<212> TYPE: PRT
<213> ORGANISM: Tachypleus tridentatus

<400> SEQUENCE: 15

Met Asp Met Arg Val Pro Ala Gln Leu Leu Gly Leu Leu Leu Leu Trp
1               5                   10                  15

Phe Pro Gly Ser Arg Cys Val Gly Val Leu Phe Pro Lys Thr Arg Asn
                20                  25                  30

Asp Asn Glu Cys Thr Ala Arg Gly Gly Leu Lys Gly Ser Cys Lys Ser
            35                  40                  45

Leu Ile Asp Cys Pro Ser Val Leu Ala Thr Leu Lys Asp Ser Phe Pro
50                  55                  60

Val Val Cys Ser Trp Asn Gly Arg Phe Gln Pro Ile Val Cys Cys Pro
65                  70                  75                  80

Asp Ala Ile Ala Pro Pro Val Thr Thr Thr Ala Val Thr Val Ile
                85                  90                  95

Ser Thr Lys Glu Pro Lys Leu Pro Arg Leu His Ile Ser Gly Cys Gly
            100                 105                 110

Lys Arg Lys Val Lys Ile Asp Ile Thr Thr Val Gly Arg Ser Gly Ser
        115                 120                 125

Pro Ile Leu Pro Pro Ile Ser Thr Pro Gln Asn Ser Thr Gly Gly Arg
        130                 135                 140

Gly Ile Ile Ala Gly Gly Val Glu Ala Lys Ile Gly Ala Trp Pro Trp
145                 150                 155                 160

Met Ala Ala Val Phe Val Lys Asn Phe Gly Ile Gly Arg Phe His Cys
                165                 170                 175
```

Ala Gly Ser Ile Ile Ser Asn Lys Tyr Ile Leu Ser Ala Ala His Ala
            180                 185                 190

Phe Leu Ile Gly Gly Arg Lys Leu Thr Pro Thr Arg Leu Ala Val Arg
        195                 200                 205

Val Gly Gly His Tyr Ile Lys Arg Gly Gln Glu Tyr Pro Val Lys Asp
    210                 215                 220

Val Ile Ile His Pro His Tyr Val Glu Lys Glu Asn Tyr Asn Asp Ile
225                 230                 235                 240

Ala Ile Ile Glu Leu Lys Glu Glu Leu Asn Phe Thr Asp Leu Val Asn
            245                 250                 255

Pro Ile Cys Leu Pro Asp Pro Glu Thr Val Thr Asp Pro Leu Lys Asp
        260                 265                 270

Arg Ile Val Thr Ala Ala Gly Trp Gly Asp Leu Asp Phe Ser Gly Pro
    275                 280                 285

Arg Ser Gln Val Leu Arg Glu Val Ser Ile Pro Val Val Pro Val Asp
290                 295                 300

Lys Cys Asp Gln Ala Tyr Glu Lys Leu Asn Thr Pro Ser Leu Lys Asn
305                 310                 315                 320

Gly Ile Thr Asn Asn Phe Leu Cys Ala Gly Leu Glu Glu Gly Gly Lys
            325                 330                 335

Asp Ala Cys Gln Gly Asp Ser Gly Gly Pro Leu Met Leu Val Asn Asn
        340                 345                 350

Thr Arg Trp Ile Val Val Gly Val Ser Phe Gly His Lys Cys Ala
    355                 360                 365

Glu Glu Gly Tyr Pro Gly Val Tyr Ser Arg Val Ala Ser Tyr Leu Asp
    370                 375                 380

Trp Ile Ala Lys Val Thr Asn Ser Leu Asp His Ala Val Thr Asn
385                 390                 395

<210> SEQ ID NO 16
<211> LENGTH: 1128
<212> TYPE: DNA
<213> ORGANISM: Tachypleus tridentatus

<400> SEQUENCE: 16
atgctggtca acaatgtctt ttccctgctc tgcttccctc tcctgatgtc cgtcgtgcgc        60
tgctccaccc tctcgagaca gcggcgccag tttgtgttcc ctgatgaaga ggaactgtgt       120
tccaaccggt tcaccgaaga gggaacttgc aagaacgtgc tggactgccg catcctgctt       180
caaaagaacg actacaacct tctcaaggag tcaatctgcg gtttcgaagg gattacccca       240
aaagtctgct gcccgaagtc ctcgcacgtg atctcaagca cccaggcacc ccctgaaact       300
accactactg agcggccccc gaagcaaatt cccccgaact gccggaagt ctgcggcatc         360
cacaacacca ccaccactag gatcatcggg gggagagaag cccctatcgg cgcctggccc       420
tggatgaccg ctgtgtacat taagcagggc ggtatccgga gcgtgcagtg cggtggagct       480
ctggtcacca atcgccacgt gatcacagcg tcacactgcg tcgtgaactc ggcgggtacc       540
gacgtgatgc ccgccgacgt gttctctgtg cggttggggg aacataacct ttactcgacc       600
gatgatgact ccaaccccaat cgatttcgcc gtgacgtccg tgaagcacca tgagcacttc       660
gtgctggcca cctacctgaa cgacatagca attctcactc tgaacgacac cgtgactttt       720
actgatcgga tcaggccaat ctgtctgccg taccgcaagc tcagatacga cgacctggcc       780
atgcgcaagc cgttcattac gggttgggga actaccgcct tcaacggacc ttcctccgcc       840

```
gtgctgcggg aagtgcagct gccgatctgg gagcacgaag cctgtagaca agcctacgaa    900
aaggacctga acattaccaa cgtgtatatg tgtgccggat tcgcggatgg cggcaaagac    960
gcatgccagg gagactccgg cggcccgatg atgctgcctg tgaaaaccgg agagttctac   1020
ctcatcggca tcgtcagctt cgggaagaaa tgcgccctgc ccggattccc cggagtgtac   1080
actaaggtca ccgagttcct cgactggatt gccgaacaca tggtgtaa                1128
```

<210> SEQ ID NO 17  
<211> LENGTH: 354  
<212> TYPE: PRT  
<213> ORGANISM: Tachypleus tridentatus

<400> SEQUENCE: 17

```
Ser Thr Leu Ser Arg Gln Arg Gln Phe Val Phe Pro Asp Glu Glu
1               5                   10                  15

Glu Leu Cys Ser Asn Arg Phe Thr Glu Gly Thr Cys Lys Asn Val
                20                  25                  30

Leu Asp Cys Arg Ile Leu Leu Gln Lys Asn Asp Tyr Asn Leu Leu Lys
            35                  40                      45

Glu Ser Ile Cys Gly Phe Glu Gly Ile Thr Pro Lys Val Cys Cys Pro
50                      55                      60

Lys Ser Ser His Val Ile Ser Ser Thr Gln Ala Pro Pro Glu Thr Thr
65                  70                  75                  80

Thr Thr Glu Arg Pro Pro Lys Gln Ile Pro Pro Asn Leu Pro Glu Val
                85                  90                  95

Cys Gly Ile His Asn Thr Thr Thr Arg Ile Ile Gly Gly Arg Glu
            100                 105                 110

Ala Pro Ile Gly Ala Trp Pro Trp Met Thr Ala Val Tyr Ile Lys Gln
                115                 120                 125

Gly Gly Ile Arg Ser Val Gln Cys Gly Gly Ala Leu Val Thr Asn Arg
130                 135                 140

His Val Ile Thr Ala Ser His Cys Val Val Asn Ser Ala Gly Thr Asp
145                 150                 155                 160

Val Met Pro Ala Asp Val Phe Ser Val Arg Leu Gly Glu His Asn Leu
                165                 170                 175

Tyr Ser Thr Asp Asp Asp Ser Asn Pro Ile Asp Phe Ala Val Thr Ser
            180                 185                 190

Val Lys His His Glu His Phe Val Leu Ala Thr Tyr Leu Asn Asp Ile
        195                 200                 205

Ala Ile Leu Thr Leu Asn Asp Thr Val Thr Phe Thr Asp Arg Ile Arg
210                 215                 220

Pro Ile Cys Leu Pro Tyr Arg Lys Leu Arg Tyr Asp Asp Leu Ala Met
225                 230                 235                 240

Arg Lys Pro Phe Ile Thr Gly Trp Gly Thr Thr Ala Phe Asn Gly Pro
                245                 250                 255

Ser Ser Ala Val Leu Arg Glu Val Gln Leu Pro Ile Trp Glu His Glu
            260                 265                 270

Ala Cys Arg Gln Ala Tyr Glu Lys Asp Leu Asn Ile Thr Asn Val Tyr
        275                 280                 285

Met Cys Ala Gly Phe Ala Asp Gly Gly Lys Asp Ala Cys Gln Gly Asp
    290                 295                 300

Ser Gly Gly Pro Met Met Leu Pro Val Lys Thr Gly Glu Phe Tyr Leu
305                 310                 315                 320

Ile Gly Ile Val Ser Phe Gly Lys Lys Cys Ala Leu Pro Gly Phe Pro
```

```
                    325                 330                 335
Gly Val Tyr Thr Lys Val Thr Glu Phe Leu Asp Trp Ile Ala Glu His
                340                 345                 350

Met Val

<210> SEQ ID NO 18
<211> LENGTH: 375
<212> TYPE: PRT
<213> ORGANISM: Tachypleus tridentatus

<400> SEQUENCE: 18

Met Leu Val Asn Asn Val Phe Ser Leu Leu Cys Phe Pro Leu Leu Met
1               5                   10                  15

Ser Val Val Arg Cys Ser Thr Leu Ser Arg Gln Arg Gln Phe Val
            20                  25                  30

Phe Pro Asp Glu Glu Leu Cys Ser Asn Arg Phe Thr Glu Glu Gly
        35                  40                  45

Thr Cys Lys Asn Val Leu Asp Cys Arg Ile Leu Leu Gln Lys Asn Asp
    50                  55                  60

Tyr Asn Leu Leu Lys Glu Ser Ile Cys Gly Phe Glu Gly Ile Thr Pro
65                  70                  75                  80

Lys Val Cys Cys Pro Lys Ser Ser His Val Ile Ser Ser Thr Gln Ala
                85                  90                  95

Pro Pro Glu Thr Thr Thr Thr Glu Arg Pro Pro Lys Gln Ile Pro Pro
            100                 105                 110

Asn Leu Pro Glu Val Cys Gly Ile His Asn Thr Thr Thr Thr Arg Ile
        115                 120                 125

Ile Gly Gly Arg Glu Ala Pro Ile Gly Ala Trp Pro Trp Met Thr Ala
130                 135                 140

Val Tyr Ile Lys Gln Gly Gly Ile Arg Ser Val Gln Cys Gly Gly Ala
145                 150                 155                 160

Leu Val Thr Asn Arg His Val Ile Thr Ala Ser His Cys Val Val Asn
                165                 170                 175

Ser Ala Gly Thr Asp Val Met Pro Ala Asp Val Phe Ser Val Arg Leu
            180                 185                 190

Gly Glu His Asn Leu Tyr Ser Thr Asp Asp Ser Asn Pro Ile Asp
        195                 200                 205

Phe Ala Val Thr Ser Val Lys His His Glu His Phe Val Leu Ala Thr
210                 215                 220

Tyr Leu Asn Asp Ile Ala Ile Leu Thr Leu Asn Asp Thr Val Thr Phe
225                 230                 235                 240

Thr Asp Arg Ile Arg Pro Ile Cys Leu Pro Tyr Arg Lys Leu Arg Tyr
                245                 250                 255

Asp Asp Leu Ala Met Arg Lys Pro Phe Ile Thr Gly Trp Gly Thr Thr
            260                 265                 270

Ala Phe Asn Gly Pro Ser Ser Ala Val Leu Arg Glu Val Gln Leu Pro
        275                 280                 285

Ile Trp Glu His Glu Ala Cys Arg Gln Ala Tyr Glu Lys Asp Leu Asn
290                 295                 300

Ile Thr Asn Val Tyr Met Cys Ala Gly Phe Ala Asp Gly Gly Lys Asp
305                 310                 315                 320

Ala Cys Gln Gly Asp Ser Gly Gly Pro Met Met Leu Pro Val Lys Thr
                325                 330                 335

Gly Glu Phe Tyr Leu Ile Gly Ile Val Ser Phe Gly Lys Lys Cys Ala
```

```
                    340                 345                 350
Leu Pro Gly Phe Pro Gly Val Tyr Thr Lys Val Thr Glu Phe Leu Asp
            355                 360                 365

Trp Ile Ala Glu His Met Val
    370                 375

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Glu Gly Arg
1
```

RECOMBINANT AMEBOCYTE LYSATE AND USES THEREOF

FIELD OF THE INVENTION

The present invention relates generally to methods and compositions for detecting and/or quantifying endotoxin in a sample. More particularly, the invention relates to hybrid amebocyte lysates (including native and recombinantly produced components) and their use for detecting and/or quantifying endotoxin in a sample.

SEQUENCE LISTING

The instant application contains a Sequence Listing which has been submitted electronically in ASCII format and is hereby incorporated by reference in its entirety. Said ASCII copy, created on Feb. 24, 2022, is named CHR-047US_SL.txt and is 75,911 bytes in size.

BACKGROUND

Microbial contamination by, for example, Gram negative bacteria, may cause severe illness and, in some cases, even death in humans. Manufacturers in certain industries, for example, the pharmaceutical, medical device, and food industries, must meet exacting standards to verify that their products do not contain levels of microbial contaminants that would otherwise compromise the health of the recipient. These industries require frequent, accurate, and sensitive testing for the presence of such microbial contaminants to meet certain standards, for example, standards imposed by the United States Food and Drug Administration (USFDA) or Environmental Protection Agency. By way of example, the USFDA requires certain manufacturers of pharmaceuticals and invasive medical devices to establish that their products are free of detectable levels of Gram negative bacterial endotoxin.

Furthermore, when people become infected with Gram negative bacteria, the bacteria may produce and secrete fever-inducing bacterial endotoxins. Bacterial endotoxins can be dangerous and even deadly to humans. Symptoms of infection may range from fever, in mild cases, to death. In order to promptly initiate proper medical treatment, it usually is important to identify, as early as possible, the presence of an endotoxin and, if possible, the concentration of the endotoxin in the patient.

To date, a variety of assays have been developed to detect the presence and/or amount of endotoxin in a test sample. One family of assays use hemocyte lysates prepared from the hemolymph of crustaceans, for example, horseshoe crabs. These assays typically exploit, in one way or another, a clotting cascade that occurs when the hemocyte lysate is exposed to endotoxin. A currently preferred hemocyte lysate is amebocyte lysate (AL) produced from the hemolymph of a horseshoe crab, for example, *Limulus polyphemus*, *Tachypleus tridentatus*, *Tachypleus gigas*, and *Carcinoscorpius rotundicauda*.

These assays use blood that is harvested from horseshoe crabs, which has resulted in concerns over the ecological sustainability of this practice. However, to date, fully synthetic or recombinant amebocyte lysate reagents are not comparable in performance to native amebocyte lysate (Dubczak et al. (2021) EUR. J. PHRM. SCI. 159:105716). Accordingly, there exists a need for new reagents that reduce the burden on the horseshoe crab population while adequately detecting endotoxin at the same level of sensitivity and accuracy as naturally derived amebocyte lysates.

SUMMARY OF THE INVENTION

The invention is based, in part, upon the discovery that the addition of a recombinant factor B and/or a recombinant proclotting enzyme to a native amebocyte lysate, e.g., for example, a diluted native amebocyte lysate, to produce a hybrid amebocyte lysate can reduce the amount of the native amebocyte lysate required to detect endotoxin in a sample, while maintaining, or in certain instances even exceeding the sensitivity and/or activity of the native amebocyte lysate for endotoxin. Furthermore, it has been discovered that hybrid amebocyte lysates described herein are superior to fully recombinant reagents, and comparable or superior to native amebocyte lysates, at detecting naturally occurring endotoxins.

Accordingly, in one aspect, the invention provides a hybrid amebocyte lysate composition. The composition comprises a native horseshoe crab amebocyte lysate. The composition also comprises a recombinant horseshoe crab factor B and/or a recombinant horseshoe crab proclotting enzyme.

In another aspect, the invention provides a hybrid amebocyte lysate composition. The composition comprises a native horseshoe crab factor C, a native horseshoe crab factor B, and a native horseshoe crab pro-clotting enzyme. The composition also comprises a recombinant horseshoe crab factor B and/or a recombinant horseshoe crab proclotting enzyme.

In another aspect, the invention provides a hybrid amebocyte lysate composition. The composition comprises a horseshoe crab factor C, horseshoe crab factor B, and a horseshoe crab proclotting enzyme, wherein (a) the ratio of horseshoe crab factor B to horseshoe crab factor C is greater than the ratio of horseshoe crab factor B to horseshoe crab factor C in a native horseshoe crab amebocyte lysate, and/or (b) the ratio of horseshoe crab proclotting enzyme to horseshoe crab factor C is greater than the ratio of horseshoe crab proclotting enzyme to horseshoe crab factor C in a native horseshoe crab amebocyte lysate.

In certain embodiments of any of the foregoing hybrid amebocyte lysate compositions, the composition does not comprise a recombinant horseshoe crab factor C.

In certain embodiments of any of the foregoing hybrid amebocyte lysate compositions, the composition comprises from about 0.05 to about 1 U/mL, for example, from about 0.1 to about 0.5 U/mL, of recombinant horseshoe crab factor B.

In certain embodiments of any of the foregoing hybrid amebocyte lysate compositions, the composition comprises from 0.05 to about 2,000 U/mL, for example, from about 50 to about 200 U/mL, of recombinant proclotting enzyme.

In certain embodiments of any of the foregoing hybrid amebocyte lysate compositions, the composition has substantially the same or greater sensitivity in detecting endotoxin than native horseshoe crab amebocyte lysate. In certain embodiments, the composition retains substantially the same activity when stored at 4° C. for 3, 4, 5, 6, 7, or 8 hours.

In certain embodiments of any of the foregoing hybrid amebocyte lysate compositions, the horseshoe crab amebocyte lysate is a *Limulus polyphemus* amebocyte lysate. In certain embodiments, the horseshoe crab factor B is a *Limulus polyphemus* factor B. In certain embodiments, the horseshoe crab proclotting enzyme is a *Limulus polyphemus* proclotting enzyme. In certain embodiments, the horseshoe crab factor C is a *Limulus polyphemus* factor C.

In certain embodiments of any of the foregoing hybrid amebocyte lysate compositions, the horseshoe crab amebocyte lysate is a *Tachypleus* amebocyte lysate. In certain embodiments, the horseshoe crab factor B is a *Tachypleus* factor B. In certain embodiments, the horseshoe crab proclotting enzyme is a *Tachypleus* proclotting enzyme. In certain embodiments, the horseshoe crab factor C is a *Tachypleus* factor C.

In certain embodiments of any of the foregoing hybrid amebocyte lysate compositions, the recombinant horseshoe crab factor B and/or the recombinant horseshoe crab proclotting enzyme are expressed in a mammalian cell, for example, a Chinese hamster ovary (CHO) or human embryonic kidney (HEK) cell. In certain embodiments, the recombinant factor B and/or the recombinant proclotting enzyme has different glycosylation than the factor B and/or the proclotting enzyme present in the native horseshoe crab amebocyte lysate.

In another aspect, the invention provides a method for preparing an endotoxin detection reagent. The method comprises adding a recombinant horseshoe crab factor B and/or a recombinant horseshoe crab proclotting enzyme to a native horseshoe crab amebocyte lysate.

In another aspect, the invention provides a method for increasing the endotoxin sensitivity of a native horseshoe crab amebocyte lysate. The method comprises adding to the native horseshoe crab amebocyte lysate a recombinant horseshoe crab factor B and/or a recombinant horseshoe crab proclotting enzyme, thereby to increase the endotoxin sensitivity of the native horseshoe crab amebocyte lysate.

In another aspect, the invention provides a method for reducing the amount of a native horseshoe crab amebocyte lysate required to detect endotoxin. The method comprises: (i) diluting the native horseshoe crab amebocyte lysate; and (ii) adding to the diluted native horseshoe crab amebocyte lysate a recombinant horseshoe crab factor B and/or a recombinant horseshoe crab proclotting enzyme to produce a hybrid amebocyte lysate.

In certain embodiments of any of the foregoing methods, the method does not comprise adding a recombinant horseshoe crab factor C to the native horseshoe crab amebocyte lysate or diluted native horseshoe crab amebocyte lysate.

In certain embodiments of any of the foregoing methods, the method comprises adding from about 0.05 to about 1 U/mL, e.g., from about 0.1 to about 0.5 U/mL, of recombinant horseshoe crab factor B to the native horseshoe crab amebocyte lysate or diluted native horseshoe crab amebocyte lysate.

In certain embodiments of any of the foregoing methods, the method comprises adding from 0.05 to about 2,000 U/mL, e.g., from about 50 to about 200 U/mL, of recombinant proclotting enzyme to the native horseshoe crab amebocyte lysate or diluted native horseshoe crab amebocyte lysate.

In certain embodiments of any of the foregoing methods, the method results in a composition that has substantially the same or greater sensitivity in detecting endotoxin than native horseshoe crab amebocyte lysate.

In certain embodiments of any of the foregoing methods, the horseshoe crab amebocyte lysate is a *Limulus polyphemus* amebocyte lysate. In certain embodiments, the horseshoe crab factor B is a *Limulus polyphemus* factor B. In certain embodiments, the horseshoe crab proclotting enzyme is a *Limulus polyphemus* proclotting enzyme. In certain embodiments, the horseshoe crab factor C is a *Limulus polyphemus* factor C.

In certain embodiments of any of the foregoing methods, the recombinant horseshoe crab factor B and/or the recombinant horseshoe crab proclotting enzyme are expressed in a mammalian cell, for example, a Chinese hamster ovary (CHO) or human embryonic kidney (HEK) cell. In certain embodiments, the recombinant factor B and/or the recombinant proclotting enzyme has different glycosylation than the factor B and/or the proclotting enzyme present in the native horseshoe crab amebocyte lysate.

These and other aspects and features of the invention are described in the following detailed description and claims.

DESCRIPTION OF THE DRAWINGS

The invention can be more completely understood with reference to the following drawings.

DETAILED DESCRIPTION

Figure 1:
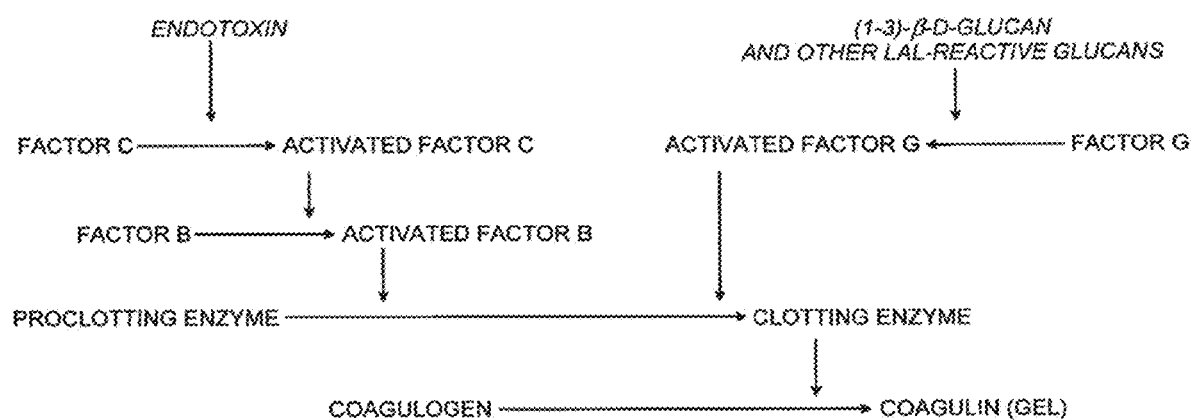
FIG. 1 is a schematic representation of the coagulation system present in amebocytes.

The invention is based, in part, upon the discovery that addition of a recombinant factor B and/or a recombinant proclotting enzyme to a native amebocyte lysate to produce a hybrid amebocyte lysate can reduce the amount of the native amebocyte lysate required to detect endotoxin in a sample, while maintaining, or in certain instances even increasing the sensitivity and/or activity of the amebocyte lysate. Furthermore, it has been discovered that hybrid amebocyte lysates described herein are superior to fully recombinant reagents, and comparable or superior to native amebocyte lysates, at detecting naturally occurring endotoxins.

Various features and aspects of the invention are discussed in more detail below.

I. Hybrid Amebocyte Lysate

The invention relates, in part, to hybrid amebocyte lysate compositions including one or more native components (e.g., a native horseshoe crab amebocyte lysate, a native horseshoe crab factor C, a native horseshoe crab factor B, and/or a native horseshoe crab pro-clotting enzyme) and one or more recombinant components (e.g., a recombinant horseshoe crab factor B, a recombinant horseshoe crab proclotting enzyme, and/or a recombinant horseshoe crab factor C).

In one aspect, the invention provides a hybrid amebocyte lysate composition comprising: (i) a native horseshoe crab amebocyte lysate, and (ii) a recombinant horseshoe crab factor B and/or a recombinant horseshoe crab proclotting enzyme.

In one aspect, the invention provides a hybrid amebocyte lysate composition comprising: (i) a native horseshoe crab factor C, (ii) a native horseshoe crab factor B, (iii) a native horseshoe crab pro-clotting enzyme, and (iv) a recombinant horseshoe crab factor B and/or a recombinant horseshoe crab proclotting enzyme.

In one aspect, the invention provides an amebocyte lysate composition comprising: (i) a horseshoe crab factor C, (ii) horseshoe crab factor B, and (iii) a horseshoe crab proclotting enzyme, wherein (a) the ratio of horseshoe crab factor B to horseshoe crab factor C is greater than the ratio of horseshoe crab factor B to horseshoe crab factor C in a native horseshoe crab amebocyte lysate, and/or (b) the ratio of horseshoe crab proclotting enzyme to horseshoe crab factor C is greater than the ratio of horseshoe crab proclotting enzyme to horseshoe crab factor C in a native horseshoe crab amebocyte lysate. It is understood that the ratio of horseshoe crab factor B to horseshoe crab factor C or the ratio of horseshoe crab proclotting enzyme to horseshoe crab factor C may refer to a ratio of enzymatic activity. Enzymatic activity may be measured by an method known in the art (e.g., as described in Example 1 hereinbelow). Alternatively, the ratio of horseshoe crab factor B to horseshoe crab factor C or the ratio of horseshoe crab proclotting enzyme to horseshoe crab factor C may refer to a ratio of protein quantity. Protein quantity may be measured by any method known in the art, including for example, Western blot, ELISA, or ultraviolet (UV) absorption at 280 nm.

In certain embodiments, a hybrid amebocyte lysate composition does not contain recombinant horseshoe crab factor C.

In certain embodiments, a hybrid amebocyte lysate composition has substantially the same or greater sensitivity for a microbial contaminant (e.g., endotoxin) as a corresponding native horseshoe crab amebocyte lysate. For example, the hybrid amebocyte lysate composition may have at least 50%, at least 60%, at least 70%, at least 80%, at least 90%, at least 95%, at least 96%, at least 97%, at least 98%, at least 99%, at least 100%, at least 110%, at least 120%, at least 130%, at least 140%, at least 150%, at least 175%, at least 200%, at least 225%, at least 250%, at least 300%, at least 350%, or at least 400% of the sensitivity of the corresponding native horseshoe crab amebocyte lysate. Amebocyte lysate sensitivity may be assayed by any method known in the art, including, for example, a kinetic chromogenic assay method (KCA), as described in Example 2 hereinbelow.

In certain embodiments, a hybrid amebocyte lysate composition containing less crude lysate than a reference native amebocyte lysate (e.g., containing 10%, 20%, 30%, 40%, 50%, 60%, 70%, 80%, or 90% of the crude lysate of a reference native amebocyte lysate) has the substantially the same or greater sensitivity for a microbial contaminant (e.g., endotoxin) as the reference native horseshoe crab amebocyte lysate. For example, the hybrid amebocyte lysate composition may have at least 50%, at least 60%, at least 70%, at least 80%, at least 90%, at least 95%, at least 96%, at least 97%, at least 98%, at least 99%, at least 100%, at least 110%, at least 120%, at least 130%, at least 140%, at least 150%, at least 175%, at least 200%, at least 225%, at least 250%, at least 300%, at least 350%, or at least 400% of the sensitivity of the reference native horseshoe crab amebocyte lysate. In certain embodiments, the hybrid amebocyte lysate composition is substantially the same as the reference native amebocyte lysate but for (i) the amount of crude lysate present, and (ii) the presence or absence of any recombinant proteins. Amebocyte lysate sensitivity may be assayed by any method known in the art, including, for example, a kinetic chromogenic assay method (KCA), as described in Example 2 hereinbelow.

In certain embodiments, a hybrid amebocyte lysate composition retains substantially the same activity when stored at 4° C. for at least 3, 4, 5, 6, 7, 8, 9, 10, 11, or 12 hours, or 3, 4, 5, 6, 7, or 8 hours.

A. Native Horseshoe Crab Amebocyte Lysate

As shown in FIG. 1, the coagulation system of hemolymph, like the mammalian blood coagulation system, comprises at least two coagulation cascades that include an endotoxin-mediated pathway (the Factor C pathway) and a (1→3)-B-D glucan-mediated pathway (the Factor G pathway).

When bacterial endotoxin is contacted with LAL, the endotoxin initiates a series of enzymatic reactions, referred to in the art as the Factor C pathway, that can involve three serine protease zymogens called Factor C, Factor B, and pro-clotting enzyme (see, FIG. 1). Briefly, upon exposure to endotoxin, the endotoxin-sensitive factor, Factor C, is activated. Activated Factor C thereafter hydrolyses and activates Factor B, whereupon activated Factor B activates proclotting enzyme to produce clotting enzyme. The clotting enzyme thereafter hydrolyzes specific sites, for example, $Arg^{18}$-$Thr^{19}$ and $Arg^{46}$-$Gly^{47}$ of coagulogen, an invertebrate, fibrinogen-like clottable protein, to produce a coagulin gel. See, for example, U.S. Pat. No. 5,605,806.

(1→3)-B-D glucans and other amebocyte lysate reactive glucans, produced by microorganisms such as yeasts and molds, can also activate the clotting cascade of amebocyte lysates, through a different enzymatic pathway, referred to in the art as the Factor G pathway (see, FIG. 1). Factor G is a serine protease zymogen that becomes activated by (1→3)-β-D glucan or other LAL reactive glucans. Upon exposure to (1→3)-β-D glucan, for example, Factor G is activated to produce activated Factor G. Activated Factor G thereafter converts the proclotting enzyme into clotting enzyme, whereupon the clotting enzyme converts coagulogen into coagulin.

As used herein, the term "native horseshoe crab amebocyte lysate" is understood to mean any lysate or fraction thereof (e.g., the components of a factor C mediated cascade) produced by the lysis, extrusion, or extraction of the cellular contents from amebocytes extracted from a horseshoe crab. Under certain circumstances, the native amebocyte lysate comprises the naturally occurring components of an enzymatic cascade (e.g., as shown in FIG. 1) produced, for example, by the lysis, extrusion, or extraction of the cellular contents from amebocytes extracted from a horseshoe crab. A native horse shoe crab amebocyte lysate, which does not contain a recombinant zymogen or functional fragment thereof (e.g., recombinant factor B, recombinant factor C or recombinant proclotting enzyme) can be used to produce a hybrid lysate described herein, by supplementation of the native amebocyte lysate with, for example, a recombinant zymogen or functional fragment thereof (e.g., recombinant factor B, recombinant factor C or recombinant proclotting enzyme). Depending upon the components present in, or admixed with, the lysate it may produce a clot in the presence of an endotoxin, for example, a Gram negative bacterial endotoxin and/or a glucan, for example, a (1→3)-β-D glucan, produced by a yeast or a mold. Preferred amebocyte lysates can be derived from horseshoe crabs belonging to the *Limulus* genus, for example, *Limulus polyphemus*, the *Tachypleus* genus, for example, *Tachypleus tridentatus* and *Tachypleus gigas*, and the *Carcinoscorpius* genus, for example, *Carcinoscorpius rotundicauda*.

In certain embodiments, a native horseshoe crab amebocyte lysate includes each of a native factor C, a native factor B, and a native proclotting enzyme.

B. Methods of Making Native Horseshoe Crab Amebocyte Lysate

Crude lysates may be produced using the procedure described in Levin et al. (1968) THROMB. DIATH. HAEMORRH. 19: 186, with modification, or in Prior 1990 "Clinical Applications of the *Limulus* Amebocyte Lysate Test" CRC PRESS 28-36 and 159-166, and in U.S. Pat. No. 4,322,217. Other lysates may include those, for example, described in U.S. Pat. Nos. 6,270,982 and 6,391,570. In certain embodiments, a crude lysate is produced as described in Example 1 hereinbelow.

It is possible to produce an endotoxin-specific lysate by removing Factor G activity from the lysate, such as the Factor G depleted lysates produced by the methods described in U.S. Pat. Nos. 6,391,570 and 6,270,982. Also, it is contemplated that lysates may be depleted of Factor G activity by the addition of certain inhibitors or modulators of Factor G activity, for example, certain detergents, saccharides, polysaccharides, and other reagents described in U.S. Pat. Nos. 5,155,032; 5,179,006; 5,318,893; 5,474,984; 5,641,643; and 6,270,982. An endotoxin-specific lysate is a lysate capable of reacting with a bacterial endotoxin but in which the reactivity to (1→3)-B-D glucan has been depleted by at least 80%, more preferably by at least 90%, and more preferably by at least 95% relative to the crude lysate from which the endotoxin-specific lysate was prepared.

Methods for enhancing the sensitivity of hemocyte lysate for endotoxin, for example, may include, without limitation, aging the crude hemocyte lysate, adjusting pH, adjusting the concentration of divalent cations, adjusting the concentration of coagulogen, chloroform extraction, and the addition of serum albumin, biocompatible buffers and/or biological detergents.

As will be apparent to one of ordinary skill, divalent metal salts, which are known to promote activation of the pro-clotting enzyme of hemocyte lysate, as well as buffers to avoid extremes of pH that could inactivate the clotting enzyme preferably are included in the lysate. Any of the buffers and salts that are understood in the art to be compatible with the amebocyte lysate system may be used. Typical formulation additives may include, without limitation, about 100-300 mM NaCl, about 10-100 mM divalent cations (e.g., $Mg^{2+}$), biocompatible buffers, e.g., Tris (tris (hydroxy)aminomethane), to give a final pH of about 6.0 to about 8.0, and, if the lysate is to be freeze dried, then sugars, e.g., mannitol or dextran. It is contemplated that the choice of appropriate formulation additives may also be determined by routine experimentation.

C. Factor B

As used herein, the term "factor B" refers to a zymogen, or a functional fragment thereof, that is capable of being activated upon cleavage by a factor C, and is capable of cleaving (e.g., enzymatically cleaving) a proclotting enzyme to form an active clotting enzyme. The term factor B includes variants having one or more amino acid substitutions, deletions, or insertions relative to a wild-type factor B sequence, and/or fusion proteins or conjugates including a factor B. As used herein, the term "functional fragment" of a factor B refers to fragment of a full-length factor B that retains, for example, at least 10%, at least 20%, at least 30%, at least 40%, at least 50%, at least 60%, at least 70%, at least 80%, at least 90%, at least 95%, at least 96%, at least 97%, at least 98%, at least 99%, or 100% of the enzymatic activity of the corresponding full-length, naturally occurring factor B. Factor B enzymatic activity may be assayed by any method known in the art, including, for example, by measuring cleavage of the chromogenic substrate H-D-Leu-Thr-Arg-pNA, for example, as described in Example 1 hereinbelow. In certain embodiments, the functional fragment comprises at least 100, 150, 200, 250, 300, 350, 360, 370, 380, or 390 consecutive amino acids present in a full-length, naturally occurring factor B.

It is contemplated that any horseshoe crab factor B, for example, a *Limulus polyphemus*, *Tachypleus tridentatus*,

*Tachypleus gigas*, or *Carcinoscorpius rotundicauda* factor B, may be used in the practice of the invention.

A DNA sequence encoding an exemplary *Limulus polyphemus* factor B is depicted in SEQ ID NO: 4. Exemplary *Limulus polyphemus* factor B amino acid sequences are depicted in SEQ ID NOs: 5 and 6. SEQ ID NO: 5 is the mature form whereas SEQ ID NO: 6 includes the signal sequence as residues 1-25. A DNA sequence encoding an exemplary *Tachypleus tridentatus* factor B is depicted in SEQ ID NO: 13. Exemplary *Tachypleus tridentatus* factor B amino acid sequences are depicted in SEQ ID NOs: 14 and 15. SEQ ID NO: 14 is the mature form whereas SEQ ID NO: 15 includes the signal sequence as residues 1-22. In certain embodiments, a factor B comprises the amino acid sequence of SEQ ID NO: 5, SEQ ID NO: 6, SEQ ID NO: 14, or SEQ ID NO: 15 or an amino acid sequence having at least 70%, at least 80%, at least 90%, at least 95%, at least 96%, at least 97%, at least 98%, at least 99%, at least 99.5%, or at least 99.8% identity to the amino acid sequence of SEQ ID NO: 5, SEQ ID NO: 6, SEQ ID NO: 14, or SEQ ID NO: 15.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al. (1990) PROC. NATL. ACAD. SCI. USA 87:2264-2268; Altschul (1993) J. MOL. EVOL. 36, 290-300; Altschul et al. (1997) NUCLEIC ACIDS RES. 25:3389-3402, incorporated by reference) are tailored for sequence similarity searching. For a discussion of basic issues in searching sequence databases, see Altschul et al. (1994) NATURE GENETICS 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al. (1992) PROC. NATL. ACAD. SCI. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: −G, Cost to open gap [Integer]: default=5 for nucleotides/11 for proteins; −E, Cost to extend gap [Integer]: default=2 for nucleotides/1 for proteins; −q, Penalty for nucleotide mismatch [Integer]: default=−3; −r, reward for nucleotide match [Integer]: default=1; −e, expect value [Real]: default=10; —W, wordsize [Integer]: default=11 for nucleotides/28 for megablast/3 for proteins; −y, Dropoff (X) for blast extensions in bits: default=20 for blastn/7 for others; −X, X dropoff value for gapped alignment (in bits): default=15 for all programs, not applicable to blastn; and −Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In certain embodiments, the factor B comprises a conservative substitution relative to a wild-type factor B sequence or a factor B sequence disclosed herein. As used herein, the term "conservative substitution" refers to a substitution with a structurally similar amino acid. For example, conservative substitutions may include those within the following groups: Ser and Cys; Leu, Ile, and Val; Glu and Asp; Gln and Asn; Lys, Arg and His; Phe, Tyr, and Trp. Conservative substitutions may also be defined by the BLAST (Basic Local Alignment Search Tool) algorithm, the BLOSUM substitution matrix (e.g., BLOSUM 62 matrix), or the PAM substitution:p matrix (e.g., the PAM 250 matrix).

In certain embodiments, the factor B is a recombinant factor B. As used herein, when referring to a protein or polypeptide, the term "recombinant" refers to a protein or polypeptide which is produced by recombinant nucleic acid, e.g., recombinant DNA, techniques, wherein generally, DNA or other nucleic acid encoding the protein or polypeptide is inserted into a suitable expression vector which is in turn introduced in to a host cell to produce the heterologous protein within the host cell.

In certain embodiments, the factor B is a native factor B. As used herein, when referring to a protein or polypeptide (e.g., native factor B), the term "native" refers to a protein or polypeptide derived from a natural source as opposed to a protein or polypeptide produced by using recombinant means, e.g., recombinant DNA technologies. A native protein or polypeptide (e.g., factor B) may be isolated. As used herein, term "isolated" refers to molecules or biological or cellular materials that are in an environment that is different from their naturally occurring environment. The term "isolated" encompasses a nucleic acid, such as DNA or RNA, or protein or polypeptide, or cell or cellular organelle, or tissue or organ, separated from other DNAs RNAs, or proteins or polypeptides, or cells or cellular organelles, or tissues or organs, respectively, that are present in a natural source.

A contemplated composition may comprise, for example, from about 0.01 to about 5 U/mL, from about 0.01 to about 3 U/mL, from about 0.01 to about 1 U/mL, from about 0.01 to about 0.9 U/mL, from about 0.01 to about 0.8 U/mL, from about 0.01 to about 0.7 U/mL, from about 0.01 to about 0.6 U/mL, from about 0.01 to about 0.5 U/mL, from about 0.01 to about 0.4 U/mL, from about 0.01 to about 0.3 U/mL, from about 0.01 to about 0.2 U/mL, from about 0.01 to about 0.1 U/mL, from about 0.01 to about 0.075 U/mL, from about 0.01 to about 0.05 U/mL, from about 0.05 to about 5 U/mL, from about 0.05 to about 3 U/mL, from about 0.05 to about 1 U/mL, from about 0.05 to about 0.9 U/mL, from about 0.05 to about 0.8 U/mL, from about 0.05 to about 0.7 U/mL, from about 0.05 to about 0.6 U/mL, from about 0.05 to about 0.5 U/mL, from about 0.05 to about 0.4 U/mL, from about 0.05 to about 0.3 U/mL, from about 0.05 to about 0.2 U/mL, from about 0.05 to about 0.1 U/mL, from about 0.05 to about 0.075 U/mL, from about 0.075 to about 5 U/mL, from about 0.075 to about 3 U/mL, from about 0.075 to about 1 U/mL, from about 0.075 to about 0.9 U/mL, from about 0.075 to about 0.8 U/mL, from about 0.075 to about 0.7 U/mL, from about 0.075 to about 0.6 U/mL, from about 0.075 to about 0.5 U/mL, from about 0.075 to about 0.4 U/mL, from about 0.075 to about 0.3 U/mL, from about 0.075 to about 0.2 U/mL, from about 0.075 to about 0.1 U/mL, from about 0.1 to about 5 U/mL, from about 0.1 to about 3 U/mL, from about 0.1 to about 1 U/mL, from about 0.1 to about 0.9

U/mL, from about 0.1 to about 0.8 U/mL, from about 0.1 to about 0.7 U/mL, from about 0.1 to about 0.6 U/mL, from about 0.1 to about 0.5 U/mL, from about 0.1 to about 0.4 U/mL, from about 0.1 to about 0.3 U/mL, from about 0.1 to about 0.2 U/mL, from about 0.2 to about 5 U/mL, from about 0.2 to about 3 U/mL, from about 0.2 to about 1 U/mL, from about 0.2 to about 0.9 U/mL, from about 0.2 to about 0.8 U/mL, from about 0.2 to about 0.7 U/mL, from about 0.2 to about 0.6 U/mL, from about 0.2 to about 0.5 U/mL, from about 0.2 to about 0.4 U/mL, from about 0.2 to about 0.3 U/mL, from about 0.3 to about 5 U/mL, from about 0.3 to about 3 U/mL, from about 0.3 to about 1 U/mL, from about 0.3 to about 0.9 U/mL, from about 0.3 to about 0.8 U/mL, from about 0.3 to about 0.7 U/mL, from about 0.3 to about 0.6 U/mL, from about 0.3 to about 0.5 U/mL, from about 0.3 to about 0.4 U/mL, from about 0.4 to about 5 U/mL, from about 0.4 to about 3 U/mL, from about 0.4 to about 1 U/mL, from about 0.4 to about 0.9 U/mL, from about 0.4 to about 0.8 U/mL, from about 0.4 to about 0.7 U/mL, from about 0.4 to about 0.6 U/mL, from about 0.4 to about 0.5 U/mL, from about 0.5 to about 5 U/mL, from about 0.5 to about 3 U/mL, from about 0.5 to about 1 U/mL, from about 0.5 to about 0.9 U/mL, from about 0.5 to about 0.8 U/mL, from about 0.5 to about 0.7 U/mL, from about 0.5 to about 0.6 U/mL, from about 0.6 to about 5 U/mL, from about 0.6 to about 3 U/mL, from about 0.6 to about 1 U/mL, from about 0.6 to about 0.9 U/mL, from about 0.6 to about 0.8 U/mL, from about 0.6 to about 0.7 U/mL, from about 0.7 to about 5 U/mL, from about 0.7 to about 3 U/mL, from about 0.7 to about 1 U/mL, from about 0.7 to about 0.9 U/mL, from about 0.7 to about 0.8 U/mL, from about 0.8 to about 5 U/mL, from about 0.8 to about 3 U/mL, from about 0.8 to about 1 U/mL, from about 0.8 to about 0.9 U/mL, from about 0.9 to about 5 U/mL, from about 0.9 to about 3 U/mL, from about 0.9 to about 1 U/mL, from about 1 to about 5 U/mL, from about 1 to about 3 U/mL, or from about 3 to about 5 U/mL of factor B (e.g., recombinant factor B). Factor B enzymatic activity may be assayed by any method known in the art, including, for example, by measuring cleavage of the chromogenic substrate H-D-Leu-Thr-Arg-pNA, for example, as described in Example 1 herein. As used herein one unit (U) of factor B activity is defined as the amount of enzyme that catalyzes the conversion of 1 micromole of a substrate (e.g., H-D-Leu-Thr-Arg-pNA) per minute.

D. Proclotting Enzyme

As used herein, the term "proclotting enzyme" refers to a zymogen, or a functional fragment thereof, that is capable of being activated upon cleavage by an activated factor B, and is capable of cleaving (e.g., enzymatically cleaving) coagulogen to form coagulin. The term proclotting enzyme includes variants having one or more amino acid substitutions, deletions, or insertions relative to a wild-type proclotting enzyme sequence, and/or fusion proteins or conjugates including a proclotting enzyme. As used herein, the term "functional fragment" of a proclotting enzyme refers to fragment of a full-length proclotting enzyme that retains, for example, at least 10%, at least 20%, at least 30%, at least 40%, at least 50%, at least 60%, at least 70%, at least 80%, at least 90%, at least 95%, at least 96%, at least 97%, at least 98%, at least 99%, or 100% of the enzymatic activity of the corresponding full-length, naturally occurring proclotting enzyme. Proclotting enzyme enzymatic activity may be assayed by any method known in the art, including, for example, by measuring cleavage of the chromogenic substrate Ac-Ile-Glu-Gly-Arg-pNA (SEQ ID NO: 19), for example, as described in Example 1 herein. In certain embodiments, the functional fragment comprises at least 100, 150, 200, 250, 300, 320, 330, 340, 350, 360, or 370 consecutive amino acids present in a full-length, naturally occurring proclotting enzyme.

It is contemplated that any horseshoe crab factor proclotting enzyme, for example, a *Limulus polyphemus, Tachypleus tridentatus, Tachypleus gigas*, or *Carcinoscorpius rotundicauda* proclotting enzyme, may be used in the practice of the invention.

A DNA sequence encoding an exemplary *Limulus polyphemus* proclotting enzyme is depicted in SEQ ID NO: 7. Exemplary *Limulus polyphemus* proclotting enzyme amino acid sequences are depicted in SEQ ID NOs: 8 and 9. SEQ ID NO: 8 is the mature form whereas SEQ ID NO:9 includes the signal sequence as residues 1-28. A DNA sequence encoding an exemplary *Tachypleus tridentatus* proclotting enzyme is depicted in SEQ ID NO: 16. Exemplary *Tachypleus tridentatus* proclotting enzyme amino acid sequences are depicted in SEQ ID NOs: 17 and 18. SEQ ID NO: 17 is the mature form whereas SEQ ID NO:18 includes the signal sequence as residues 1-21. In certain embodiments, a proclotting enzyme comprises the amino acid sequence of SEQ ID NO: 8, SEQ ID NO: 9, SEQ ID NO: 17, or SEQ ID NO: 18, or an amino acid sequence having at least 70%, at least 80%, at least 90%, at least 95%, at least 96%, at least 97%, at least 98%, at least 99%, at least 99.5%, or at least 99.8% identity to the amino acid sequence of SEQ ID NO: 8, SEQ ID NO: 9, SEQ ID NO: 17, or SEQ ID NO: 18. In certain embodiments, the proclotting enzyme comprises a conservative substitution relative to a wild-type proclotting enzyme sequence or a proclotting enzyme sequence disclosed herein.

In certain embodiments, the proclotting enzyme is a recombinant proclotting enzyme. In certain embodiments, the proclotting enzyme is a native proclotting enzyme, e.g., an isolated native proclotting enzyme.

A contemplated composition may comprise, for example, from about 0.01 to about 3,000 U/mL, from about 0.01 to about 2,500 U/mL, from about 0.01 to about 2,000 U/mL, from about 0.01 to about 1,500 U/mL, from about 0.01 to about 1,000 U/mL, from about 0.01 to about 500 U/mL, from about 0.01 to about 400 U/mL, from about 0.01 to about 300 U/mL, from about 0.01 to about 200 U/mL, from about 0.01 to about 100 U/mL, from about 0.01 to about 50 U/mL, from about 0.01 to about 20 U/mL, from about 0.01 to about 10 U/mL, from about 0.01 to about 5 U/mL, from about 0.01 to about 2 U/mL, from about 0.01 to about 1 U/mL, from about 0.01 to about 0.5 U/mL, from about 0.01 to about 0.1 U/mL, from about 0.1 to about 3,000 U/mL, from about 0.1 to about 2,500 U/mL, from about 0.1 to about 2,000 U/mL, from about 0.1 to about 1,500 U/mL, from about 0.1 to about 1,000 U/mL, from about 0.1 to about 500 U/mL, from about 0.1 to about 400 U/mL, from about 0.1 to about 300 U/mL, from about 0.1 to about 200 U/mL, from about 0.1 to about 100 U/mL, from about 0.1 to about 50 U/mL, from about 0.1 to about 20 U/mL, from about 0.1 to about 10 U/mL, from about 0.1 to about 5 U/mL, from about 0.1 to about 2 U/mL, from about 0.1 to about 1 U/mL, from about 0.1 to about 0.5 U/mL, from about 0.5 to about 3,000 U/mL, from about 0.5 to about 2,500 U/mL, from about 0.5 to about 2,000 U/mL, from about 0.5 to about 1,500 U/mL, from about 0.5 to about 1,000 U/mL, from about 0.5 to about 500 U/mL, from about 0.5 to about 400 U/mL, from about 0.5 to about 300 U/mL, from about 0.5 to about 200 U/mL, from about 0.5 to about 100 U/mL, from about 0.5 to about 50 U/mL, from about 0.5 to about 20 U/mL, from about 0.5 to about 10 U/mL, from about 0.5 to about 5 U/mL, from about 0.5 to about 2 U/mL, from about 0.5 to about 1 U/mL, from about 1 to about 3,000 U/mL, from about 1 to about 2,500 U/mL, from about 1 to about 2,000 U/mL, from about 1 to about 1,500 U/mL, from about 1 to about 1,000 U/mL, from about 1 to about 500 U/mL, from about 1 to about 400 U/mL, from about 1 to about 300 U/mL, from about 1 to about 200 U/mL, from about 1 to about 100 U/mL, from about 1 to about 50 U/mL, from about 1 to about 20 U/mL, from about 1 to about 10 U/mL, from about 1 to about 5 U/mL, from about 1 to about 2 U/mL, from about 2 to about 3,000 U/mL, from about 2 to about 2,500 U/mL, from about 2 to about 2,000 U/mL, from about 2 to about 1,500 U/mL, from about 2 to about 1,000 U/mL, from about 2 to about 500 U/mL, from about 2 to about 400 U/mL, from about 2 to about 300 U/mL, from about 2 to about 200 U/mL, from about 2 to about 100 U/mL, from about 2 to about 50 U/mL, from about 2 to about 20 U/mL, from about 2 to about 10 U/mL, from about 2 to about 5 U/mL, from about 5 to about 3,000 U/mL, from about 5 to about 2,500 U/mL, from about 5 to about 2,000 U/mL, from about 5 to about 1,500 U/mL, from about 5 to about 1,000 U/mL, from about 5 to about 500 U/mL, from about 5 to about 400 U/mL, from about 5 to about 300 U/mL, from about 5 to about 200 U/mL, from about 5 to about 100 U/mL, from about 5 to about 50 U/mL, from about 5 to about 20 U/mL, from about 5 to about 10 U/mL, from about 10 to about 3,000 U/mL, from about 10 to about 2,500 U/mL, from about 10 to about 2,000 U/mL, from about 10 to about 1,500 U/mL, from about 10 to about 1,000 U/mL, from about 10 to about 500 U/mL, from about 10 to about 400 U/mL, from about 10 to about 300 U/mL, from about 10 to about 200 U/mL, from about 10 to about 100 U/mL, from about 10 to about 50 U/mL, from about 10 to about 20 U/mL, from about 20 to about 3,000 U/mL, from about 20 to about 2,500 U/mL, from about 20 to about 2,000 U/mL, from about 20 to about 1,500 U/mL, from about 20 to about 1,000 U/mL, from about 20 to about 500 U/mL, from about 20 to about 400 U/mL, from about 20 to about 300 U/mL, from about 20 to about 200 U/mL, from about 20 to about 100 U/mL, from about 20 to about 50 U/mL, from about 50 to about 3,000 U/mL, from about 50 to about 2,500 U/mL, from about 50 to about 2,000 U/mL, from about 50 to about 1,500 U/mL, from about 50 to about 1,000 U/mL, from about 50 to about 500 U/mL, from about 50 to about 400 U/mL, from about 50 to about 300 U/mL, from about 50 to about 200 U/mL, from about 50 to about 100 U/mL, from about 100 to about 3,000 U/mL, from about 100 to about 2,500 U/mL, from about 100 to about 2,000 U/mL, from about 100 to about 1,500 U/mL, from about 100 to about 1,000 U/mL, from about 100 to about 500 U/mL, from about 100 to about 400 U/mL, from about 100 to about 300 U/mL, from about 100 to about 200 U/mL, from about 200 to about 3,000 U/mL, from about 200 to about 2,500 U/mL, from about 200 to about 2,000 U/mL, from about 200 to about 1,500 U/mL, from about 200 to about 1,000 U/mL, from about 200 to about 500 U/mL, from about 200 to about 400 U/mL, from about 200 to about 300 U/mL, from about 300 to about 3,000 U/mL, from about 300 to about 2,500 U/mL, from about 300 to about 2,000 U/mL, from about 300 to about 1,500 U/mL, from about 300 to about 1,000 U/mL, from about 300 to about 500 U/mL, from about 300 to about 400 U/mL, from about 400 to about 3,000 U/mL, from about 400 to about 2,500 U/mL, from about 400 to about 2,000 U/mL, from about 400 to about 1,500 U/mL, from about 400 to about 1,000 U/mL, from about 400 to about 500 U/mL, from about 500 to about 3,000 U/mL, from about 500 to about 2,500 U/mL, from about 500 to about 2,000 U/mL, from about 500 to about 1,500 U/mL, from about 500 to about 1,000 U/mL, from about 1,000 to about 3,000 U/mL, from about 1,000 to about 2,500 U/mL, from about 1,000 to about 2,000 U/mL, from about 1,000 to about 1,500 U/mL, from about 1,500 to about 3,000 U/mL, from about 1,500 to about 2,500 U/mL, from about 1,500 to about 2,000 U/mL, from about 2,000 to about 3,000 U/mL, from about 2,000 to about 2,500 U/mL, or from about 2,500 to about 3,000 U/mL of proclotting enzyme (e.g., recombinant proclotting enzyme). Proclotting enzyme enzymatic activity may be assayed by any method known in the art, including, for example, by measuring cleavage of the chromogenic substrate Ac-Ile-Glu-Gly-Arg-pNA (SEQ ID NO: 19), for example, as described in Example 1 hereinbelow. As used herein one unit (U) of proclotting enzyme activity is defined as the amount of enzyme that catalyzes the conversion of 1 micromole of a substrate (e.g., Ac-Ile-Glu-Gly-Arg-pNA (SEQ ID NO: 19)) per minute.

E. Factor C

As used herein, the term "factor C" refers to a zymogen, or a functional fragment thereof, that is capable of being activated by endotoxin, and is capable of cleaving (e.g., enzymatically cleaving) factor B to form an activated factor B. The term factor C includes variants having one or more amino acid substitutions, deletions, or insertions relative to a wild-type factor C sequence, and/or fusion proteins or conjugates including a factor C. As used herein, the term "functional fragment" of a factor C refers to fragment of a full-length factor C that retains, for example, at least 10%, at least 20%, at least 30%, at least 40%, at least 50%, at least 60%, at least 70%, at least 80%, at least 90%, at least 95%, at least 96%, at least 97%, at least 98%, at least 99%, or 100% of the enzymatic activity of the corresponding full-length, naturally occurring factor C. Factor C enzymatic activity may be assayed by any method known in the art, including, for example, by measuring cleavage of the chromogenic substrate Z-Val-Pro-Arg-pNA, for example, as described in Example 1 herein. In certain embodiments, the functional fragment comprises at least 100, 200, 300, 400, 500, 600, 700, 800, 900, or 1,000 consecutive amino acids present in a full-length, naturally occurring factor C.

It is contemplated that any horseshoe crab factor C, for example, a *Limulus polyphemus*, *Tachypleus tridentatus*, *Tachypleus gigas*, or *Carcinoscorpius rotundicauda* factor C, may be used in the practice of the invention.

A DNA sequence encoding an exemplary *Limulus polyphemus* factor C is depicted in SEQ ID NO: 1. Exemplary *Limulus polyphemus* factor C amino acid sequences are depicted in SEQ ID NOs: 2 and 3. SEQ ID NO: 2 is the mature form whereas SEQ ID NO:3 includes the signal sequence as residues 1-25. A DNA sequence encoding an exemplary *Tachypleus tridentatus* factor C is depicted in SEQ ID NO: 10. Exemplary *Tachypleus tridentatus* factor C amino acid sequences are depicted in SEQ ID NOs: 11 and 12. SEQ ID NO: 11 is the mature form whereas SEQ ID NO: 12 includes the signal sequence as residues 1-21. In certain embodiments, a factor C comprises the amino acid sequence of SEQ ID NO: 2, SEQ ID NO: 3, SEQ ID NO: 11, or SEQ ID NO: 12, or an amino acid sequence having at least 70%, at least 80%, at least 90%, at least 95%, at least 96%, at least 97%, at least 98%, at least 99% identity, at least 99.5%, or at least 99.8% to the amino acid sequence of SEQ ID NO: 2, SEQ ID NO: 3, SEQ ID NO: 11, or SEQ ID NO: 12. In certain embodiments, the factor C comprises a conservative substitution relative to a wild-type factor C sequence or a factor C sequence disclosed herein.

In certain embodiments, the factor C is a recombinant factor C. In certain embodiments, the factor C is a native factor C, e.g., an isolated native factor C.

In certain embodiments, a recombinant horseshoe crab factor C for use as an endotoxin detection reagent, either alone, or in combination with other horseshoe crab proteins (e.g., factor B, proclotting enzyme and/or factor C, whether sourced naturally or produced recombinantly) is expressed in a mammalian cell, for example, a Chinese hamster ovary (CHO) or human embryonic kidney (HEK) cell. In certain embodiments, the recombinant factor C is glycosylated differently (e.g., has one or more different glycosyl groups or a glycosylation pattern) when compared to factor C present in the native horseshoe crab amebocyte lysate, or when compared to factor C produced recombinantly in distinct expression host cells. As a non-limiting example, factor C may be produced recombinantly in a gene-edited cell line, such as GnTI− HEK cells (e.g., HEK cells that do not have N-acetylglucosaminyltransferase I (GnTI) activity) that produce factor C proteins lacking ($\alpha$-2,3)-linked terminal sialic acid. Use of such readily available gene-edited cell lines may be desirable for high-yield expression of homogenously glycosylated recombinant proteins.

F. Methods of Making Recombinant Proteins

Methods for producing recombinant proteins known in the art. For example, DNA molecules encoding a protein of interest (e.g., factor B, proclotting enzyme and/or factor C, as disclosed herein) can be synthesized chemically or by recombinant DNA methodologies. The resulting DNA molecules encoding the protein of interest can be ligated to other appropriate nucleotide sequences, including, for example, expression control sequences, to produce conventional gene expression constructs (i.e., expression vectors) encoding the desired protein. Production of defined gene constructs is within routine skill in the art.

Nucleic acids encoding desired proteins (e.g., factor B, proclotting enzyme and/or factor C, as disclosed herein) can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma. Transformed host cells can be grown under conditions that permit the host cells to express the genes that encode the protein of interest.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO or HEK cells, it is first inserted into an expression vector containing a suitable eukaryotic promoter, a secretion signal, a poly A sequence, and a stop codon. Optionally, the vector or gene construct may contain enhancers and introns. The gene construct can be introduced into eukaryotic host cells using conventional techniques.

A polypeptide or protein of interest (e.g., factor B, proclotting enzyme and/or factor C, as disclosed herein) can be produced by growing (culturing) a host cell transfected with an expression vector encoding such a polypeptide or protein, under conditions that permit expression of the polypeptide or protein. Following expression, the polypeptide can be harvested and purified or isolated using techniques known in the art, e.g., affinity tags such as glutathione-S-transferase (GST) or histidine tags.

Provided herein are isolated nucleic acids comprising the sequence of SEQ ID NO: 1, SEQ ID NO: 4, SEQ ID NO: 7, SEQ ID NO: 10, SEQ ID NO: 13, or SEQ ID NO: 16. These sequences can be spliced into a suitable expression vector and operatively linked to a promoter for use in a desired expression host using standard recombinant DNA methodologies. Also provided are expression host cells (e.g., mammalian host cells) comprising such an expression vector, which can then be used to express the protein encoded by one or more of the foregoing nucleic acid sequences. Exemplary methods for making recombinant factor B, proclotting enzyme and factor C are described in Example 1 herein.

In one embodiment, provided herein is a method of producing a horseshoe crab recombinant factor C protein, the method comprising: (a) expressing a nucleic acid sequence encoding the recombinant horseshoe crab factor C in a host cell (e.g., a HEK293 cell or a CHO cell) engineered to remove a glycosyltransferase enzyme (e.g., N-acetylglucosaminyltransferase); and (b) purifying the recombinant factor C expressed in the host cell. Also provided is a recombinant horseshoe crab factor C protein (e.g., a factor C protein that does not contain ($\alpha$-2,3)-linked terminal sialic acid) produced by such a method. The resulting recombinant horseshoe crab factor C can be used to prepare an endotoxin detection reagent (e.g., a hybrid lysate), by admixing such a recombinant factor C with a composition comprising recombinant horseshoe crab factor B and recombinant horseshoe crab proclotting enzyme.

It is understood that a recombinantly expressed polypeptide or protein may have a different molecular weight and/or be differently glycosylated relative to a corresponding native polypeptide or protein. Similarly, a protein or polypeptide recombinantly expressed in a first host cell type may have a different molecular weight and/or be differently glycosylated relative to a corresponding protein or polypeptide expressed in a second, different host cell type. Glycosylation of recombinant proteins produced in mammalian host cells is described, for example, in Lis et al. (1993) EUR. J. BIOCHEM. 218:1-27, Parodi (2000) ANNU. REV. BIOCHEM. 69:69-93, Viswanathan et al. (2005) BIOCHEM. 44:7526-7534, Tomiya et al. (2004) GLYCOCONJUGATE JOURNAL 21: 343-360, Tomiya et al. (2003) ACC. CHEM. RES. 36:613-620, Gerngros (2004) NAT. BIOTECHNOL. 22:1409-1414, and Demain et al. (2009) BIOTECHNOLOGY ADVANCES 27:297-306.

G. Methods of Making Hybrid Lysate

Hybrid amebocyte lysates may be produced by combining native and recombinant components disclosed herein.

The invention provides a method for preparing a microbial contaminant (e.g., endotoxin) detection reagent, for increasing the sensitivity of a native horseshoe crab amebocyte lysate for a microbial contaminant (e.g., endotoxin), and/or reducing the amount of a native horseshoe crab amebocyte lysate required to detect a microbial contaminant (e.g., endotoxin). The method comprises adding a recombinant horseshoe crab factor B and/or a recombinant horseshoe crab proclotting enzyme to a native horseshoe crab amebocyte lysate. In certain embodiments, the method comprises diluting the native horseshoe crab amebocyte lysate. For example, a contemplated method comprises diluting a native horseshoe crab amebocyte lysate to produce a diluted horseshoe crab amebocyte lysate; and adding to the diluted native horseshoe crab amebocyte lysate a recombinant horseshoe crab factor B and/or a recombinant horseshoe crab proclotting enzyme. In certain embodiments, the native horseshoe crab amebocyte lysate is diluted by 10%, 20%, 30%, 40%, 50%, 60%, 70%, 80%, 90%, 100%, 150%, 200%, 250%, 300%, 350%, 400%, 450%, 500%, 600%, 700%, 800%, 900%, or 1,000%.

Hybrid amebocyte lysate compositions preferably are sterile. Sterilization can be accomplished by any suitable method, e.g., filtration through sterile filtration membranes. Where the composition is lyophilized, filter sterilization can be conducted prior to or following lyophilization and reconstitution.

Hybrid amebocyte lysate compositions can also be dried onto a solid surface (such as a vial, a cartridge or a 12-well or 96-well plate), such as by lyophilization. Prior to drying, one or more additives are optionally admixed with the hybrid amebocyte lysate. For example, a resolubilizing and/or an anti-flaking agent can be included. The resolubilizing agent is an agent that, either alone or in combination with another resolubilizing agent, facilitates the resolubilization of one or more components of the hybrid amebocyte lysate once the hybrid amebocyte lysate is exposed to a fluid sample. The resolubilizing agent preferably also stabilizes the lysate in its dried form. The resolubilizing agent provided in the mixture facilitates the stability of the reagents and their dissolution during the assay. Resolubilizing agents include, for example, one or more sugars, salts, or combinations thereof. Preferred sugar resolubilizing agents include, for example, mannitol, mannose, sorbitol, trehalose, maltose, dextrose, sucrose, and other monosaccharides or disaccharides. The anti-flaking agent included in the mixture further stabilizes the reagents and reduces flaking of the dried lysate. The anti-flaking agent preferably also stabilizes the lysate in its dried form. Preferred anti-flaking agents include, for example, one or more polymers, for example, polyethylene glycol, polyvinyl pyrolidone, polyvinyl alcohol, mannitol, dextran, and proteins, for example, serum albumin. An anti-frothing agent such as polyvinyl alcohol or polypropylene glycol can also be included. Salts and/or buffers, such as sodium chloride, magnesium sulfate, and HEPES buffer can also be included. Other kinds of buffers, such as TRIS-HCl buffer, TES, MOPS, PIPES, BES, MOPSO, DIPSO, MOBS, TAPSO, HEPPSO, POPSO, TEA, EPPS, Tricine, and phosphate can be used, as can other buffers with buffering capacity between pH 7 and pH 8, as this is a preferred range of pH for the reaction. The target pH of the composition, after admixture with a sample, is preferably between 7.3 and 8.0.

The mixture can be dried onto a surface of the conduit in an environment having a temperature of about 4° C. to about 40° C., more preferably, from about 10° C. to about 35° C., more preferably, from about 15° C. to about 30° C. and a relative humidity of about 0% to about 30%, more preferably, from about 2% to about 20%, more preferably, from about 4% to about 10%. Preferably, the temperature is about 25° C. and the relative humidity is about 5%. Drying preferably occurs for about 10 minutes to about 8 hours, more preferably for about 1 hour in a temperature regulated drying chamber.

In another embodiment, the mixture is dried onto the surface of the conduit by lyophilization or freeze-drying, for example, at temperatures below 0° C., for example, from about −75° C. to about −10° C., more preferably from about −30° C. to about −20° C.

II. Methods of Detection and Sample Preparation Considerations

Hybrid amebocyte lysates disclosed herein can be used in various assays to detect a microbial contaminant (e.g., endotoxin). The invention provides a method of detecting the presence and/or amount of a microbial contaminant (e.g., endotoxin) in a sample. The method comprises contacting a hybrid amebocyte lysate (e.g., a hybrid amebocyte lysate disclosed herein) with a sample (e.g., a sample suspected of containing endotoxin), allowing the hybrid amebocyte lysate to react with the sample to produce a detectable product (e.g., a gel, increase in turbidity, or a colored or light-emitting product), and detecting the detectable product (e.g., visually or by the use of an optical detector).

Hybrid amebocyte lysates disclosed herein can be used to detect a microbial contaminant (e.g., endotoxin) using, for example, endpoint or kinetic assays. Exemplary endpoint assays include an endpoint chromogenic assay or an endpoint turbidimetric assay. Exemplary kinetic assays include a kinetic turbidimetric assay, a one-step kinetic assay or a multi-step kinetic assay. Each of the assays is discussed in more detail below. Furthermore, it is understood that the assays may be modified to be performed in a particular assay format, for example, in a cartridge or in the well of a plate, for example, a 96 well plate.

A. Kinetic Assays

Exemplary kinetic assays include multi-step kinetic assays, single-step kinetic assays, and kinetic turbidimetric assays.

(i) Multi-Step Kinetic Assay

A multi-step kinetic assay (for example, as described in U.S. Pat. No. 7,329,538) is initiated by combining the sample to be tested with a volume of hybrid amebocyte lysate to produce a sample-hybrid amebocyte lysate mixture. The mixture then is incubated for a predetermined period of time. The mixture then is contacted with a substrate, for example, a chromogenic or fluorogenic substrate, to produce a sample-hybrid amebocyte lysate-substrate mixture. Thereafter, the time in which a preselected change in an optical property (for example, a specific change in an absorbance value or a specific change in a transmission value) is measured.

The assay can be calibrated by measuring the time in which a preselected change in an optical property occurs when a certain amount of a microbial contaminant (e.g., endotoxin) is introduced into the assay. By comparing the result generated by a test sample against the results generated by one or more known amounts of the microbial contaminant (e.g., endotoxin), it is possible to detect the presence or amount of the microbial contaminant (e.g., endotoxin) in a test sample.

It is understood that a multi-step kinetic assay can be run in a cartridge format. The cartridge preferably is used with an optical detector, for example, a hand-held optical detector as shown and described in U.S. Pat. No. Des. 390,661.

By way of example and as illustrated in FIGS. 8A-8D, cartridge 1 has a substantially planar housing fabricated, for example, from a moldable biocompatible material. The housing may be fabricated from any material, however, transparent and/or translucent glass or polymers are preferred. Preferred polymers include, for example, polystyrene, polycarbonate, acrylic, polyester, optical grade polymers, or any plastic such that the optical cell is substantially transparent. The housing contains at least one fluid inlet port 4, at least one optical cell 6, and at least one conduit 8 having a fluid contacting surface for providing fluid flow communication between the fluid inlet port 4 and optical cell 6. The only requirements for the optical cell 6 are that it defines a void capable of containing a sample to be tested and that a portion of the optical cell 6 is transparent to light. Cartridge 1 may also have at least one pump port 12 in fluid flow communication with fluid inlet port 4 and optical cell 6 for attaching the cartridge 1 to a pump. The pump may then impart a negative pressure via pump port 12 to pull the sample from fluid inlet port 4 to optical cell 6. A hybrid amebocyte lysate is disposed on a first region 14 of the fluid contacting surface of conduit 8, so that when a sample is applied to fluid inlet port 4, the sample traverses region 14 and solubilizes or reconstitutes the hybrid amebocyte lysate into the sample as it moves toward optical cell 6.

A second region 16 of the fluid contacting surface of conduit 8 is spaced apart from and downstream of first region 14. In this configuration, hybrid amebocyte lysate is disposed at first region 14 and a chromogenic or fluorogenic substrate is disposed at second region 16, so that after the sample is contacted with the hybrid amebocyte lysate in region 14, the sample-lysate mixture traverses conduit 8 and contacts the substrate in region 16. The sample-lysate-substrate mixture then traverses conduit 8 to optical cell 6.

The cartridges can be designed and used according to the type and/or number of tests required. For example, a single sample may be tested, for example, in duplicate or triplicate, for example, for research laboratory use or for medical device and biopharmaceutical testing. Alternatively, two or more different samples may be tested individually. The cartridge preferably is a single-use, disposable cartridge that is discarded after one use. The cartridges typically use approximately 20-100 fold less hemocyte lysate per sample than is used in the conventional endpoint chromogenic or kinetic chromogenic assays performed in multi-well plates, and thus provides a less costly and environmentally-friendlier test.

Figure 8A:
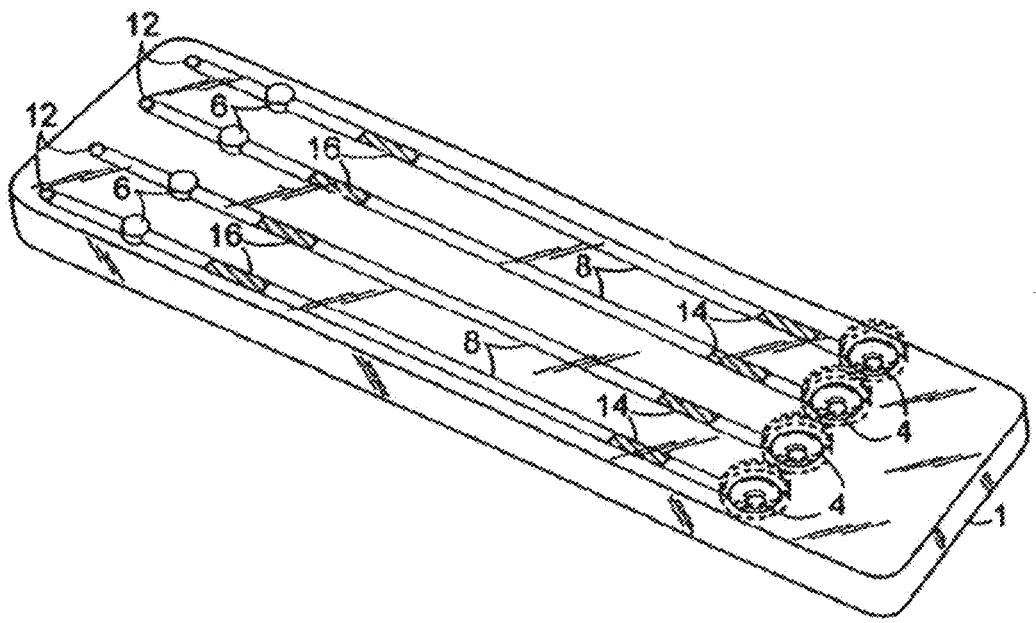
FIGS. 8A-8D are schematic illustrations in perspective view (FIG. 8A), top view (FIG. 8B), side view (FIG. 8C), and end view (FIG. 8D), of an exemplary cartridge useful in performing assays with the hybrid lysate described herein.
Figure 8B:
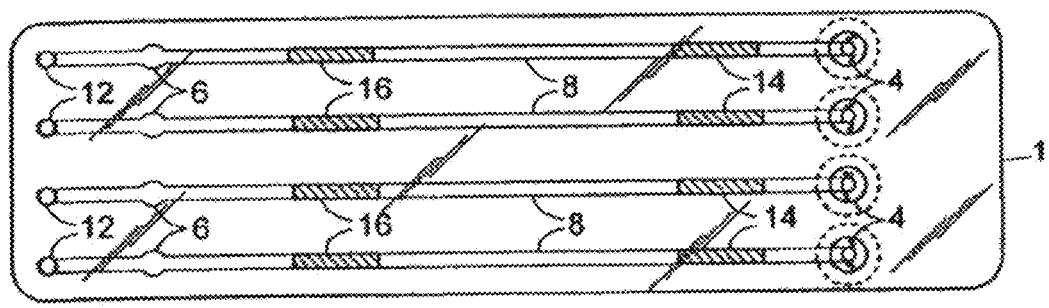
Figure 8C:
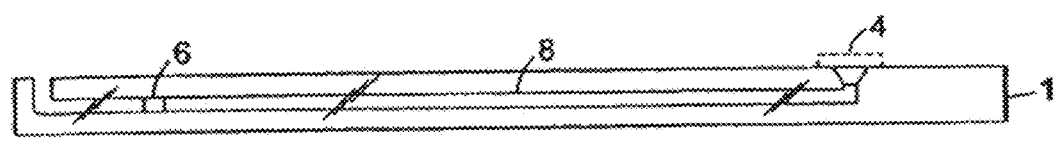
Figure 8D:
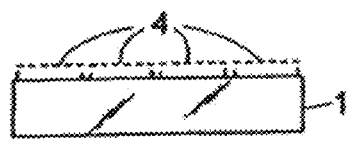

With reference to FIG. 8A, in order to perform a multi-step kinetic assay in an exemplary cartridge 1, a sample is first moved, for example, by pump action, to a first region 14 containing the hybrid amebocyte lysate, where it is mixed and incubated for a predetermined period of time. The sample-hybrid amebocyte lysate mixture then is moved, for example, by pump action, to the second region 16 containing the substrate, for example, a chromogenic or fluorogenic substrate, where it is solubilized. The sample-substrate mixture then is moved to optical cell 6, for a measurement of an optical property. The time intervals required for mixing and incubating steps are preprogrammed for optimal specificity and sensitivity to the microbial contaminant (e.g., endotoxin) concentration range of interest.

Although the multi-step assay may be performed in a cartridge of the type discussed above, it may also be employed in a variety of other formats, for example, within the well of a microtiter plate. In this type of assay, a sample of interest is combined with a hybrid amebocyte lysate and incubated for a predetermined period of time. Then, after the predetermined period of time, a chromogenic or fluorogenic substrate is added to the well. After mixing, the time in which a preselected change in an optical property occurs is measured. The result can then be compared against one or more standard values to measure the presence or amount of a microbial contaminant (e.g., endotoxin) in the sample.

In the well-type format, the samples and reagents are added to each of the wells, preferably using an automated system, such as a robot, and the plate processed by a microplate reader, which can be programmed to sequentially read the absorbance of each well in a repetitive fashion.

(ii) Single-Step Kinetic Assay

A single-step kinetic assay, for example, a single step-chromogenic assay, is described in U.S. Pat. No. 5,310,657. Briefly, a kinetic chromogenic assay includes the steps of (i) simultaneously solubilizing a hybrid amebocyte lysate with a sample to be analyzed and a substrate, for example, a chromogenic substrate, (ii) incubating the resulting mixture at a temperature of about 0° to about 40° C., preferably about 25° to about 40° C., over a predetermined time range and (iii) measuring a time required for a calorimetric change to reach a pre-selected value or change of the calorimetric readout, using a conventional spectrophotometer.

This type of assay, like the multi-step kinetic assay, can be performed in a cartridge or a well-type format. A cartridge similar to that described above for the multi-step kinetic assay can be modified for use in single-step kinetic assay. With reference to FIG. 8A, chromogenic or fluorogenic substrate is applied, for example, to the surface of conduit 8 at first region 14 together with the hybrid amebocyte lysate. To perform a kinetic assay in cartridge 1 and in reference to FIG. 8A, a sample is moved, for example, by pump action, to a first region 14 of the conduit 8 containing both the hybrid amebocyte lysate and substrate, where they are solubilized, for example, by cycling between forward and reverse pump action. The sample-hybrid amebocyte lysate-substrate mixture then is moved to optical cell 6 for measurement of an optical property, for example, the absorbance or transmittance properties of the sample by an optical detector. The detector may determine how long it takes for each optical property to exhibit, for example, a 5% drop in optical transmittance. Results from multiple assays, for example, two assays, can be averaged.

The assay can be calibrated by measuring the time in which a preselected change in an optical property occurs when a certain amount of a microbial contaminant (e.g., endotoxin) is introduced into the assay. By comparing the result generated by a test sample against one or more results with known amounts of the microbial contaminant (e.g., endotoxin), it is possible to measure the presence or amount of the microbial contaminant (e.g., endotoxin) in the test sample.

This type of assay format may be employed in a variety of other formats, for example, within the well of a microtiter plate. In this type of assay, a sample of interest is mixed with a hybrid amebocyte lysate and a chromogenic or fluorogenic substrate. After mixing, the time in which a preselected change in an optical property occurs is measured. The result can then be compared against standard values to measure the presence or amount of a microbial contaminant (e.g., endotoxin) in the sample of interest.

(iii) Kinetic Turbidimetric Assay

A kinetic turbidimetric assay can include the steps of (i) solubilizing a hybrid amebocyte lysate with a sample to be analyzed, (ii) incubating the resulting mixture at a temperature of about 0° to about 40° C., preferably about 25° to about 40° C., over a predetermined time range, and (iii) measuring a time required for either a turbidity change caused by coagulation to reach a pre-selected value or a ratio in change of the turbidity, using a conventional coagulometer, nephrometer, or spectrophotometer.

This type of assay, like the previous assays, can be performed in a cartridge or a well-type format. A cartridge similar to that described above for the multi-step or single-step kinetic assays can be modified for use in kinetic turbidimetric assays. With reference to FIG. 8A, no chromogenic or fluorogenic substrate needs to be applied to either first region 14 or second region 16.

Referring to FIG. 8A, in order to perform a kinetic turbidimetric assay in a cartridge 1, a sample is, for example, moved to a first region 14 of the conduit 8 containing the hybrid amebocyte lysate, where it is solubilized, for example, by cycling between forward and reverse pump action. The sample-lysate mixture then is moved to optical cell 6 for measurement of an optical property, for example, turbidity, by measuring, for example, the absorbance or transmittance properties of the sample-lysate mixture using an optical detector. The detector may determine how long it takes for each optical property to exhibit, for example, a 5% drop in optical transmittance. Results from multiple assays, for example, two assays can be averaged.

The assay can be calibrated by measuring the time in which a preselected change in an optical property, for example, turbidity, occurs when a certain amount of a microbial contaminant (e.g., endotoxin) is introduced into the assay. By comparing the result generated by a test sample against one or more results with known amounts of the microbial contaminant (e.g., endotoxin), it is possible to measure the presence or amount of the microbial contaminant (e.g., endotoxin) in the test sample.

This type of assay format may be employed in a variety of other formats, for example, within the well of a microtiter plate. In this type of assay, a sample of interest is mixed with a hybrid amebocyte lysate. After mixing, the time in which a preselected change in an optical property, for example, turbidity, occurs is measured. The result can then be compared against standard values to measure the presence or amount of a microbial contaminant (e.g., endotoxin) in the sample of interest.

B. Endpoint Assays

Exemplary endpoint assays include endpoint chromogenic or fluorogenic and endpoint turbidimetric assays.

(i) Endpoint Chromogenic or Fluorogenic Assay

Endpoint chromogenic or fluorogenic assays can include the steps of (i) solubilizing a hybrid amebocyte lysate with a sample to be analyzed, (ii) incubating the resulting mixture at a temperature of about 0° to about 40° C., preferably about 25° to about 40° C., for a predetermined time, (iii) contacting substrate, for example, a chromogenic or fluorogenic substrate, with the incubated sample-hybrid amebocyte lysate mixture, (iv) optionally adding a reaction inhibitor, for example, acetic acid, and (v) measuring, for example by calorimetric change, a substance produced from the substrate by enzymatic activity.

This type of assay can be performed in a cartridge or in a well-type format. When an endpoint chromogenic or fluorogenic assay is performed in a cartridge 1 (see, FIG. 8A), a sample is moved, for example, to a first region 14 of the conduit 8 containing the hybrid amebocyte lysate, where it is solubilized, for example, by cycling between forward and reverse pump action. Following a predetermined incubation period, the sample-hybrid amebocyte lysate mixture then is moved, for example, by pump action to a second region 16 of the conduit 8 containing the chromogenic or fluorogenic substrate, where it is solubilized, for example, by cycling between forward and reverse pump action. The sample-hybrid amebocyte lysate-substrate mixture optionally then is moved to a third region containing a reaction inhibitor. Afterwards, the sample-hybrid amebocyte lysate-substrate mixture is moved to optical cell 6 for measurement of an optical property, for example, the absorbance or transmittance properties of the sample by an optical detector. It is contemplated, however, that when performing an endpoint chromogenic or fluorogenic assay in a cartridge it is not necessary to stop the reaction using a reaction inhibitor. Under this type of assay, the final optical readings (endpoint readings) are recorded at a predetermined time.

The assay can be calibrated by measuring an optical property, for example, absorbance or transmittance, when a certain amount of a microbial contaminant (e.g., endotoxin) is introduced into the assay. By comparing the result generated by a test sample against one or more results with known amounts of the microbial contaminant (e.g., endotoxin), it is possible to measure the presence or amount of the microbial contaminant (e.g., endotoxin) in the test sample.

As discussed, this type of assay format may be employed in a variety of other formats, for example, within the well of a microtiter plate. In this type of assay, a sample of interest is mixed with a hybrid amebocyte lysate and incubated for a preselected period of time. Then, a chromogenic or fluorogenic substrate is added to the mixture and the sample incubated for another period of time. Then a reaction inhibitor, for example, acetic acid, is added to the sample, and an optical property of the sample, for example, absorbance or transmittance, is measured. The result can then be compared against standard values to measure the presence or amount of a microbial contaminant (e.g., endotoxin) in the sample of interest.

(ii) Endpoint Turbidimetric Assay

End point turbidimetric assays can include the steps of (i) solubilizing a hybrid amebocyte lysate with a sample to be analyzed, (ii) incubating the resulting mixture at a temperature of about 0° to about 40° C., preferably about 25° to about 40° C., for a predetermined time, (iii) optionally adding a reaction inhibitor, for example, acetic acid, and (iv) measuring the increase in turbidity as a result of coagulation, if any, using a conventional coagulometer, nepherometer, or spectrophotometer.

Endpoint turbidimetric assays can be performed in a cartridge-type format. With reference to FIG. 8A, a sample is applied to cartridge 1 and is moved, for example, to a first region 14 of the conduit 8 containing the hemocyte lysate, where it is solubilized, for example, by cycling between forward and reverse pump action. The sample-lysate mixture then is moved to optical cell 6 for measurement of an optical property, for example, turbidity, using an optical detector. Results from multiple assays, for example, two assays can be averaged.

The assay can be calibrated, for example, by measuring the turbidity at a preselected time when a certain amount of a microbial contaminant (e.g., endotoxin) is introduced into the assay. By comparing the result generated by a test sample against one or more results with known amounts of the microbial contaminant (e.g., endotoxin), it is possible to measure the presence or amount of the microbial contaminant (e.g., endotoxin) in the test sample.

This type of assay format may also be run in other formats, for example, within the well of a microtiter plate. In this type of assay, a sample of interest is mixed with a hybrid amebocyte lysate and incubated for a preselected period of time. The reaction can then be stopped by the addition of an inhibitor. An optical property, for example, turbidity, of the sample then is measured at a preselected time point. The result can then be compared against standard values to measure the presence or amount of the microbial contaminant (e.g., endotoxin) in the sample of interest.

C. Specimen Collection and Preparation Considerations

In general, materials used to harvest, store, or otherwise contact a sample to be tested, as well as test reagents, should be free of microbial contamination, for example, should be pyrogen-free. Materials may be rendered pyrogen-free by, for example, heating at 250° C. for 30 minutes. Appropriate precautions should be taken to protect depyrogenated materials from subsequent environmental contamination.

The hybrid amebocyte lysate may be used to measure the presence or amount of a microbial contaminant (e.g., endotoxin) in a sample of interest, for example, in a fluid, for example, a fluid to be administered locally or systemically, for example, parenterally to a mammal, or a body fluid to be tested for infection, including, for example, blood, lymph, urine, serum, plasma, ascites fluid, lung aspirants, and the like. In addition, the assays may be used to detect a microbial contaminant (e.g., endotoxin) present on a surface. For example, the surface of interest is swabbed and the swab then is introduced into or dissolved in liquid. The liquid can then be assayed as described herein.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/ or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

It should be understood that the order of steps or order for performing certain actions is immaterial so long as the present invention remain operable. Moreover, two or more steps or actions may be conducted simultaneously.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified.

Unless defined otherwise, all technical and scientific terms used herein have the same meaning as commonly understood by one of ordinary skill in the art to which this invention belongs. The abbreviations used herein have their conventional meaning within the chemical and biological arts.

EXAMPLES

The following Examples are merely illustrative and are not intended to limit the scope or content of the invention in any way.

Example 1

This Example describes the preparation of recombinant *Limulus polyphemus* factor C, factor B, and pro-clotting enzyme.

DNA sequences encoding *Limulus polyphemus* factor C, factor B and pro-clotting enzyme (with codon usage optimized for expression in mammalian cells) were cloned into expression plasmid BD609 (ATUM). The DNA sequence encoding *Limulus polyphemus* factor C is depicted in SEQ ID NO: 1 (and the corresponding amino acid sequence is depicted in SEQ ID NO: 3). The DNA sequence encoding *Limulus polyphemus* factor B is depicted in SEQ ID NO: 4 (and the corresponding amino acid sequence is depicted in SEQ ID NO: 6). The DNA sequence encoding *Limulus polyphemus* pro-clotting enzyme is depicted in SEQ ID NO: 7 (and the corresponding amino acid sequence is depicted in SEQ ID NO: 9). Expression plasmids were transfected into HEK-293 cells using the FreeStyle 293 Expression System (Thermo Fisher) to generate a stable clonal cell lines.

For expression and purification, HEK-293 cells were thawed and added to FreeStyle 293 Expression Media in a flask. Cells were grown at 37° C., 5-7% $CO_2$ at 120 rpm and passaged every 24-72 hours. When cells reached the desired volume and density, they were used to seed a total of 20 L of culture in a WAVE Bioreactor. After 72 hours, the supernatant was harvested by centrifugation at 4,000×g for 15 minutes followed by sterile filtration. The supernatant was concentrated to <2 L and buffer exchanged by Tangential Flow Filtration (TFF, GE Life Sciences). The TFF system was equilibrated with 20 mM Tris-HCl buffer pH 8.0 containing 20 mM NaCl.

To mitigate endotoxin exposure, all materials used were single use. Water for injection was used for all buffers, and all buffers were made on the day of use.

The amount of each recombinant protein was measured in terms of activity (U/mL) assayed under the following conditions. Recombinant factor C (rFC) was activated by addition of endotoxin (1 µg/mL lipopolysaccharide from *E. coli* 055:B5 (List Labs)) and incubation at 37° C. for 30 minutes. Then, the cleavage of the synthetic substrate Z-Val-Pro-Arg-pNA was measured by monitoring absorbance at 405 nm at 37° C. Recombinant factor B (rFB) was activated by addition of activated rFC and incubation at 37° C. for 1 hour. Then, the cleavage of the synthetic substrate H-D-Leu-Thr-Arg-pNA was measured by monitoring absorbance at 405 nm at 37° C. Recombinant pro-clotting enzyme (rPCE) was activated by addition of activated rFB and incubation at 37° C. for 1 hour. Then, the cleavage of the synthetic substrate Ac-Ile-Glu-Gly-Arg-pNA (SEQ ID NO: 19) was measured by monitoring absorbance at 405 nm at 37° C. One unit of activity was defined as the amount of enzyme that catalyzed the conversion of 1 micromole of substrate per minute.

Example 2

This example describes the addition of recombinant *Limulus polyphemus* factor C, factor B, and/or pro-clotting enzyme to crude *Limulus* amebocyte lysate (LAL), and the resulting endotoxin detection activity.

Crude LAL was prepared generally as described in Levin et al. (1968) THROMB. DIATH. HAEMORRH. 19:186. Briefly, hemolymph was harvesting from horseshoe crab. The resulting hemolymph was centrifuged to produce an amebocyte pellet. The amebocytes were then re-harvested, re-rinsed, and re-centrifuged. After second rinsing and harvesting steps, the resulting amebocytes were lysed by osmotic shock, and the resulting crude amebocyte lysate was stored at 2-8° C. until further use.

Recombinant *Limulus polyphemus* factor C (rFC), factor B (rFB), and pro-clotting enzyme (rPCE) were prepared as described in Example 1. A typical LAL endotoxin detection reagent includes 20% crude LAL, appropriate/compatible divalent cations, detergents, excipients for lyophilization, and substrate (Ac-Ile-Glu-Gly-Arg-pNA (SEQ ID NO: 19)). LAL endotoxin detection reagents were generated including reduced amounts of crude LAL (e.g., 10% or 5%), as well as additional recombinant proteins, as shown in TABLE 1.

TABLE 1

| Reagent No. | Final concentration | | | |
|---|---|---|---|---|
| | Crude LAL (%) | rFC (U/mL) | rFB (U/mL) | rPCE (U/mL) |
| 0 | 10 | None | None | None |
| 1 | 10 | 21.4 | None | None |
| 2 | 10 | None | 0.2 | None |
| 3 | 10 | None | 0.11 | 114 |
| 4 | 5 | None | 0.11 | 114 |
| 5 | 5 | 10.7 | 0.11 | 114 |
| 6 | 5 | None | 0.12 | 190 |

Endotoxin was detected using a kinetic chromogenic assay method (KCA). Briefly, 0.1 mL of LAL reagent was mixed with 0.1 mL of a sample containing RSE (US Reference Standard Endotoxin). Reaction of endotoxin with the LAL reagent leads to cleavage of the Ac-Ile-Glu-Gly-Arg-pNA (SEQ ID NO: 19) substrate in the LAL reagent and a resulting chromogenic signal that can be measured by absorbance at 405 nm. The activity of the LAL reagent was measured by onset time (the amount of time to reach to reach a particular absorbance (OD 0.05) at 405 nm. Onset time was measured with 0.02-20 EU/mL RSE, and logarithmic plotting of the onset times at each concentration was used to generate a standard curve.

Figure 2:
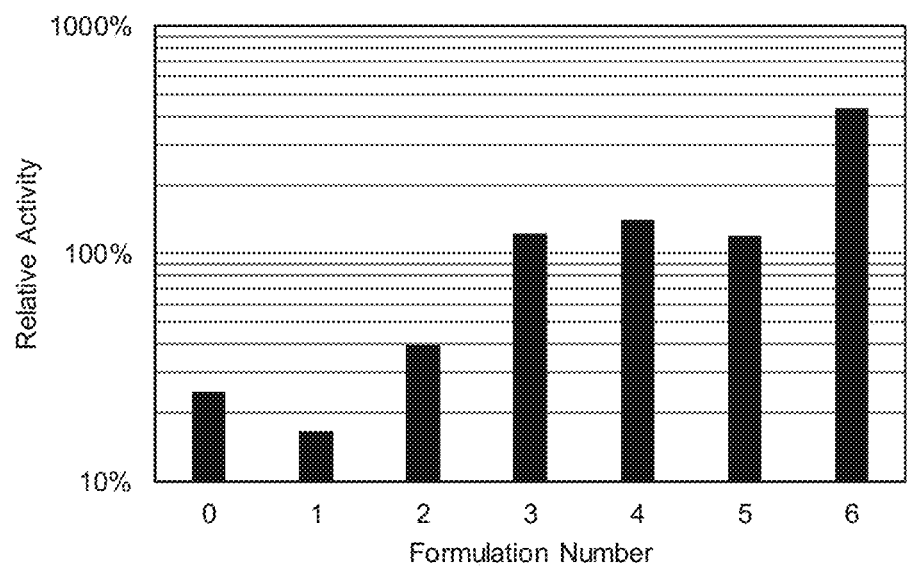
FIG. 2 is bar graph depicting relative activity of the indicated LAL reagents in a kinetic chromogenic assay (KCA).

The onset time at 0.2 EU/mL of RSE was compared for different reagents. Results are shown in FIG. 2. Activity in FIG. 2 is relative to an LAL reagent containing undiluted (20%) crude LAL, i.e., 100% activity in FIG. 2 corresponds to the activity (onset time for 0.2 EU/mL of RSE, calculated as described above) of an LAL reagent containing undiluted (20%) crude LAL.

Reagent No. 0 (including diluted (10%) crude LAL, with no additional recombinant proteins) showed 25% activity relative to a reagent including undiluted (20%) crude LAL. Addition of rFc alone (Reagent No. 1) did not increase relative activity. Addition of rFB alone (Reagent No. 2) did increase relative activity. However, the greatest increase in relative activity was observed following the addition of both rFB and rPCE. For certain reagents (Reagent Nos. 4-6) the relative activity was greater than 100%. In other words, even though these reagents contained diluted crude LAL, they showed greater endotoxin detection activity than a corresponding reagent with undiluted crude LAL.

Together, these results show that the addition of rFB and/or rPCE to a native amebocyte lysate (e.g., native LAL) can reduce the amount of native amebocyte lysate required to detect endotoxin (e.g., in a KCA assay) while maintaining, or in certain instances even increasing, sensitivity of the amebocyte lysate.

Example 3

This example describes the addition of varying amounts of recombinant *Limulus polyphemus* factor B to crude *Limulus* amebocyte lysate (LAL), and the resulting impact on endotoxin detection activity.

Recombinant *Limulus polyphemus* factor B (rFB) and pro-clotting enzyme (rPCE) were prepared as described in Example 1, crude LAL was prepared as described in Example 2, and LAL reagent activity was assayed generally as described in Example 2.

LAL reagents were generated containing diluted crude LAL, rPCE, and varying amounts of rFB, as shown in TABLE 2. The rFB amounts used were 0, 0.2, and 0.4 U/mL.

Figure 3:
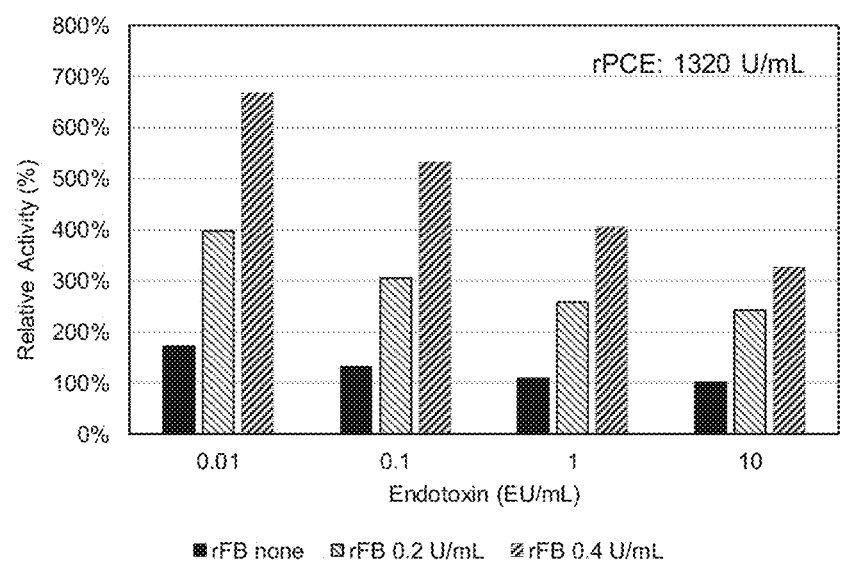
FIG. 3 is bar graph depicting relative activity of the indicated LAL reagents in a kinetic chromogenic assay (KCA).

Results are shown in FIG. 3 and TABLE 3. FIG. 3 depicts activity for the indicated reagents relative to the activity of Reagent No. 1 (an LAL reagent containing undiluted (20%) crude LAL and no recombinant proteins) at the same endotoxin concentration, i.e., 100% activity in FIG. 3 for a given endotoxin concentration corresponds to the activity of Reagent No. 1 at the same endotoxin concentration. TABLE 3 depicts onset times at the indicated endotoxin concentration for each reagent.

As shown in FIG. 3 and TABLE 3, addition of rPCE alone increased activity, as Reagent No. 2 (with diluted crude LAL and rPCE) had comparable activity to Reagent No. 1 (with undiluted crude LAL and no rPCE). However, the greatest increase in activity was observed following the addition of both rFB and rPCE, as seen in Reagent Nos. 3 and 4, which had substantially increased activity relative to Reagent No. 1. The increase in activity was generally in proportion to the amount of rFB that was added.

TABLE 2

| | Reagent No. | | | |
|---|---|---|---|---|
| | 1 | 2 | 3 | 4 |
| LAL | 100% (20%) | 50% (10%) | 50% (10%) | 50% (10%) |
| rPCE (U/mL) | None | 1320 | 1320 | 1320 |
| rFB (U/mL) | None | None | 0.2 | 0.4 |

TABLE 3

| Endotoxin | Onset Time (Sec) | | | |
|---|---|---|---|---|
| (EU/mL) | 1 | 2 | 3 | 4 |
| NC | 5999 | 5678 | 5220 | 5820 |
| 0.01 | 4650 | 4035 | 3233 | 2820 |
| 0.1 | 2543 | 2370 | 1905 | 1650 |
| 1 | 1403 | 1373 | 1103 | 985 |
| 10 | 785 | 784 | 630 | 584 |

Together, these results show that the addition of rFB and/or rPCE to a native amebocyte lysate (e.g., native LAL) can reduce the amount of native amebocyte lysate required to detect endotoxin (e.g., in a KCA assay) while maintaining, or in certain instances even increasing, sensitivity of the amebocyte lysate.

Example 4

This example describes the preparation of lyophilized LAL reagents containing diluted crude LAL and recombinant *Limulus polyphemus* factor B (rFB) and pro-clotting enzyme (rPCE).

rFB and rPCE were prepared as described in Example 1, and crude LAL was prepared as described in Example 2. LAL reagents were generated containing diluted crude LAL, rPCE, and rFB as shown in TABLE 4, and were lyophilized.

Figure 4:
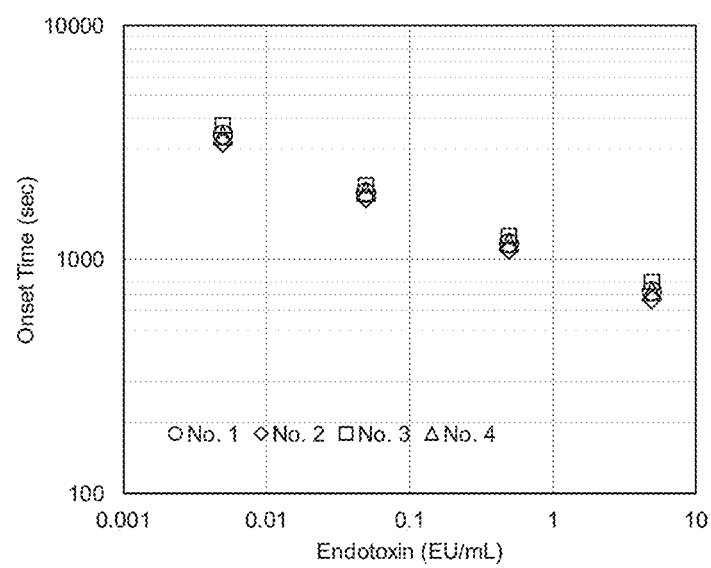
FIG. 4 is a line graph depicting onset time for the indicated LAL reagents as a function of endotoxin concentration in a kinetic chromogenic assay (KCA).

LAL reagent activity was assayed generally as described in Example 2. Results are shown in FIG. 4 and TABLE 5. FIG. 4 shows the onset time at each indicated endotoxin concentration for the reagents, and TABLE 5 shows information on regression curves that result from fitting the data shown in FIG. 4. All formulations showed a dose-dependent response to endotoxin.

TABLE 4

| | Final concentration | | |
|---|---|---|---|
| Reagent No. | Crude LAL (%) | rFB (U/mL) | rPCE (U/mL) |
| 1 | 10 | 0.2 | 50 |
| 2 | 10 | 0.2 | 100 |
| 3 | 10 | 0.1 | 50 |
| 4 | 10 | 0.1 | 100 |

TABLE 5

| | Item | | | |
|---|---|---|---|---|
| | No. 1 | No. 2 | No. 3 | No. 4 |
| Slope | −0.222 | −0.223 | −0.222 | −0.221 |
| Y-intercept | 2249 | 2101 | 2440 | 2257 |
| r | −0.999 | −1.00 | −0.998 | −0.999 |

These results indicate that hybrid amebocyte lysates (including, e.g., diluted crude LAL, rFB, and/or rPCE) maintain activity following lyophilization.

Example 5

This example describes the preparation of LAL reagents containing diluted crude LAL, recombinant *Limulus polyphemus* factor B (rFB), and recombinant *Limulus polyphemus* pro-clotting enzyme (rPCE) and their use in kinetic turbidimetric (KTA) or gel-clot assays.

rFB and rPCE were prepared as described in Example 1, and crude LAL was prepared as described in Example 2. LAL reagents were generated containing 0.5 U/mL rFB, 100 U/mL rPCE, and 19% crude LAL (which is about half amount of crude lysate in a typical KTA LAL reagent). KTA and gel-clot assays were performed according to the Bacterial Endotoxins Test as described in the United States Pharmacopeia (USP).

Figures 5A, 5B:
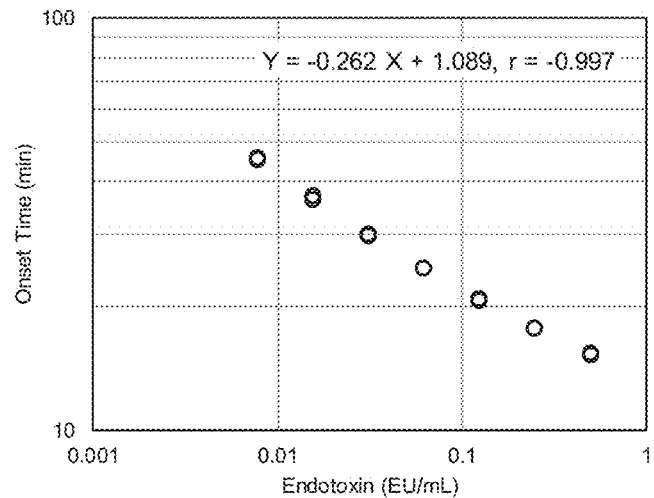
FIG. 5A is a line graph depicting onset time for a hybrid LAL reagent as a function of endotoxin concentration in a kinetic turbidometric assay (KTA).
FIG. 5B is a chart depicting gel clot formation using a hybrid LAL reagent at the indicated endotoxin concentrations.

Results for the KTA assay are shown in FIG. 5A and for the gel-clot assay are shown in FIG. 5B. The reagent exhibited a dose dependent response to RSE in the KTA assay, and an endpoint of 0.015 EU/mL in the gel-clot assay.

Together, these results show that the addition of recombinant proteins (e.g., rFB and/or rPCE) to a native amebocyte lysate (e.g., native LAL) can reduce the amount of native amebocyte lysate required to detect endotoxin (e.g., in a KTA or gel-clot assay) while maintaining sensitivity of the amebocyte lysate.

Example 6

This example describes the preparation of LAL reagents containing further diluted crude LAL, recombinant *Limulus polyphemus* factor B (rFB), and recombinant *Limulus polyphemus* pro-clotting enzyme (rPCE) and their use in kinetic turbidimetric (KTA) or gel-clot assays.

rFB and rPCE were prepared as described in Example 1, and crude LAL was prepared as described in Example 2. LAL reagents were generated containing 0.5 U/mL rFB, 100 U/mL rPCE, and 12% crude LAL (which is about 30% the amount of crude lysate in a typical KTA LAL reagent). LAL reagent activity was assayed generally as described in Example 5.

Figures 6A, 6B:
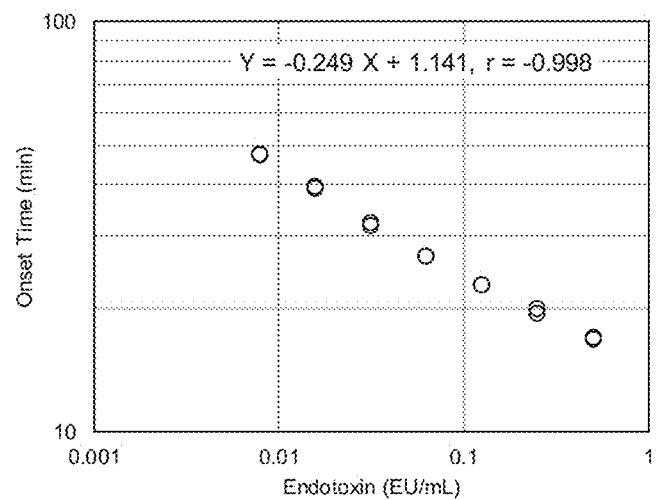
FIG. 6A is a line graph depicting onset time for a hybrid LAL reagent as a function of endotoxin concentration in a kinetic turbidometric assay (KTA).
FIG. 6B is a chart depicting gel clot formation using a hybrid LAL reagent at the indicated endotoxin concentrations.

Results for the KTA assay are shown in FIG. 6A and for the gel-clot assay are shown in FIG. 6B. The LAL reagent exhibited a dose dependent response to RSE in the KTA assay, but did not achieve an endpoint in this gel-clot assay.

Together, these results show that the addition of recombinant proteins (e.g., rFB and/or rPCE) to a native amebocyte lysate (e.g., native LAL) can reduce the amount of native amebocyte lysate required to detect endotoxin (e.g., in a KTA) while maintaining sensitivity of the amebocyte lysate.

Example 7

Natural environmental endotoxins (NEE), including endotoxins in water samples, are different from purified endotoxin, such as RSE prepared from *E. coli*, and often show low reactivity to recombinant reagents including recombinant Factor C reagents and recombinant LAL (Dubczak et al. (2021) EUR. J. PHRM. SCI. 159:105716). This example describes the preparation of LAL reagents containing diluted crude LAL, recombinant *Limulus polyphemus* factor B (rFB), and recombinant *Limulus polyphemus* proclotting enzyme (rPCE) and their use in the detection of NEEs.

The following reagents were tested in this Example: (i) a fully recombinant LAL, including 20 U/mL rFC, 0.3 U/mL rFB, and 350 U/mL rPCE ("rLAL"), (ii) a hybrid LAL including diluted (10%) crude LAL, 0.1 U/mL rFB, and 100 U/mL rPCE ("hybrid"), (iii) a first commercially available recombinant factor C (PyroGene, Lonza, "rFC #1"), (iv) a second commercially available recombinant factor C (EndoZyme, BioMerieux, "rFC #2"), (v) a first commercially available native LAL reagent (Endochrome-K, Charles River), and (vi) a second commercially available native LAL reagent (Kinetic QCL, Lonza). For rLAL and hybrid, rFc, rFB and rPCE were prepared as described in Example 1, crude LAL was prepared as described in Example 2, and activity was assayed generally as described in Example 2. All commercially available reagents were used according to manufacturer's instructions.

The commercially available native LAL reagents (Endochrome-K and Kinetic QCL) were used as a positive control. NEE in 114 water samples was detected using both Endochrome-K and Kinetic QCL, and the average of these two values was set to 100%. rLAL, hybrid, rFC #1, and rFC #2 were also used detect NEE in the same 114 water samples, and the results were compared to those obtained using Endochrome-K and Kinetic QCL. According to the criteria in the Bacterial Endotoxins Test (BET) in pharmacopoeias, each reagent was considered to agree with the Endochrome-K and Kinetic QCL average if it differed by no more than a factor of 2 (i.e., ranged from 50% to 200%). The results are shown in TABLE 6.

TABLE 6

| Criteria | rFC #1 Sub-total | Ratio | rFC #2 Sub-total | Ratio | rLAL Sub-total | Ratio | Hybrid Sub-total | Ratio |
| --- | --- | --- | --- | --- | --- | --- | --- | --- |
| <50% | 93 | 81.6% | 111 | 97.4% | 44 | 38.6% | 1 | 0.9% |
| 50%-200% | 21 | 18.4% | 3 | 2.6% | 70 | 61.4% | 110 | 96.5% |
| >200% | 0 | 0.0% | 0 | 0.0% | 0 | 0.0% | 3 | 2.6% |
| Total | 114 | 100% | 114 | 100% | 114 | 100% | 114 | 100% |

As shown in TABLE 6, the hybrid lysate showed 96.5% agreement with the native LAL reagents (Endochrome-K and Kinetic QCL) while rLAL, rFC #1, and rFC #2 showed high rates of failure. Notably, rFC #1 and rFC #2 reagents failed on the lower side more than 80%, suggesting a high rate of potential false negatives when using these reagents.

Together, these results indicate that hybrid amebocyte lysate reagents (including, e.g., diluted crude LAL, rFB, and/or rPCE) are able to detect NEE at levels comparable to native LAL reagents, and are superior at detecting NEE relative to fully recombinant reagents.

Example 8

This example describes the addition of recombinant *Tachypleus tridentatus* factor B, and/or pro-clotting enzyme to crude *Tachypleus* amebocyte lysate (TAL), and the resulting endotoxin detection activity.

Recombinant *Tachypleus tridentatus* factor B (rFB) and proclotting enzyme (rPCE) were prepared using the same cloning, expression, and purification methods described in Example 1. The DNA sequence encoding *Tachypleus tridentatus* factor B is depicted in SEQ ID NO: 13 (and the corresponding amino acid sequence is depicted in SEQ ID NO: 15). The DNA sequence encoding *Tachypleus tridentatus* pro-clotting enzyme is depicted in SEQ ID NO: 16 (and the corresponding amino acid sequence is depicted in SEQ ID NO: 18).

Commercially available TAL reagent (Zhanjiang A & C Biological Ltd., China) was reconstituted with LAL reagent water and diluted two-fold in a buffer containing 80 mM HEPES buffer (pH 7.6), 1.6% NaCl, 20 mM $MgSO_4$, and 1 mM Ac-Ile-Glu-Gly-Arg-pNA (SEQ ID NO: 19). This reagent is referred to as "100% TAL". A hybrid reagent, referred to as "50% TAL-Hybrid", was prepared by diluting 100% TAL two-fold and adding 0.1 U/mL rFB and 100 U/mL rPCE. A control reagent, referred to as "50% TAL" was also prepared by diluting 100% TAL two-fold without the addition of any recombinant proteins.

Figure 7:
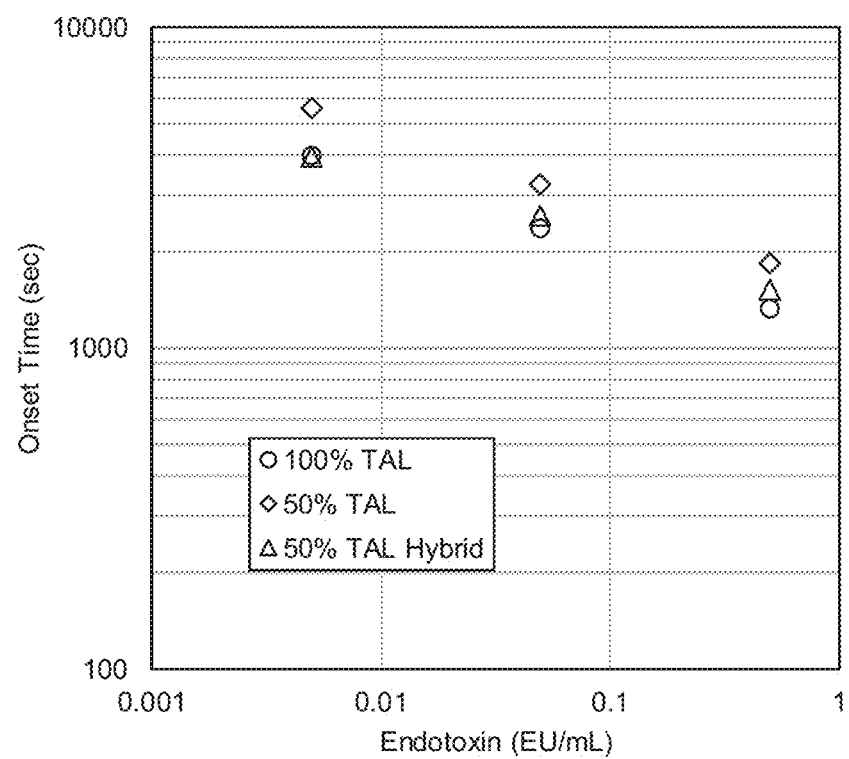
FIG. 7 is a line graph depicting onset time for the indicated TAL reagents as a function of endotoxin concentration in a kinetic chromogenic assay (KCA).

100% TAL, 50% TAL, and 50% TAL-Hybrid were tested in a KCA assay (generally as described in Example 2). Results are shown in FIG. 7. As depicted, the sensitivity of 50% TAL was lower than 100% TAL (with 50% TAL having 25% of the sensitivity of 100% TAL). However, 50% TAL-Hybrid showed similar sensitivity as 100% TAL (with 50% TAL-Hybrid having 79% of the sensitivity of 100% TAL).

100% TAL, 50% TAL, rLAL (as described in Example 7) and 50% TAL-Hybrid were also used to detect NEE in one of the water samples from Example 7. Results are shown in TABLE 7. Endotoxin values measured using 100% TAL were set to 100%. As depicted, 50% TAL-Hybrid had comparable activity to 100% TAL, and greater activity than 50% TAL or rLAL.

TABLE 7

| Reagent | Relative Activity |
| --- | --- |
| 100% TAL | 100% |
| 50% TAL | 57% |
| rLAL | 9% |
| 50% TAL Hybrid | 88% |

Together, these results show that the addition of rFB and/or rPCE to a native amebocyte lysate (e.g., native TAL) can reduce the amount of native amebocyte lysate required to detect endotoxin (e.g., in a KCA assay) while maintaining, or in certain instances even increasing, sensitivity of the amebocyte lysate.

Example 9

This example describes the addition of recombinant *Limulus polyphemus* factor B, and/or pro-clotting enzyme to crude *Tachypleus* amebocyte lysate (TAL), and the resulting endotoxin detection activity.

Recombinant *Limulus polyphemus* factor B (rFB) and proclotting enzyme (rPCE) were prepared as described in Example 1. Commercially available TAL reagent (Zhanjiang A & C Biological Ltd., China) was reconstituted with LAL reagent water and diluted two-fold in a buffer containing 80 mM HEPES buffer (pH 7.6), 1.6% NaCl, 20 mM $MgSO_4$, and 1 mM Ac-Ile-Glu-Gly-Arg-pNA (SEQ ID NO: 19). This reagent is referred to as "100% TAL". A hybrid reagent, referred to as "50% TAL-rLP Hybrid", was prepared by diluting 100% TAL two-fold and adding 0.1 U/mL *Limulus polyphemus* rFB and 100 U/mL *Limulus polyphemus* rPCE. A control reagent, referred to as "50% TAL" was also prepared by diluting 100% TAL two-fold without the addition of any recombinant proteins.

Figure 9:
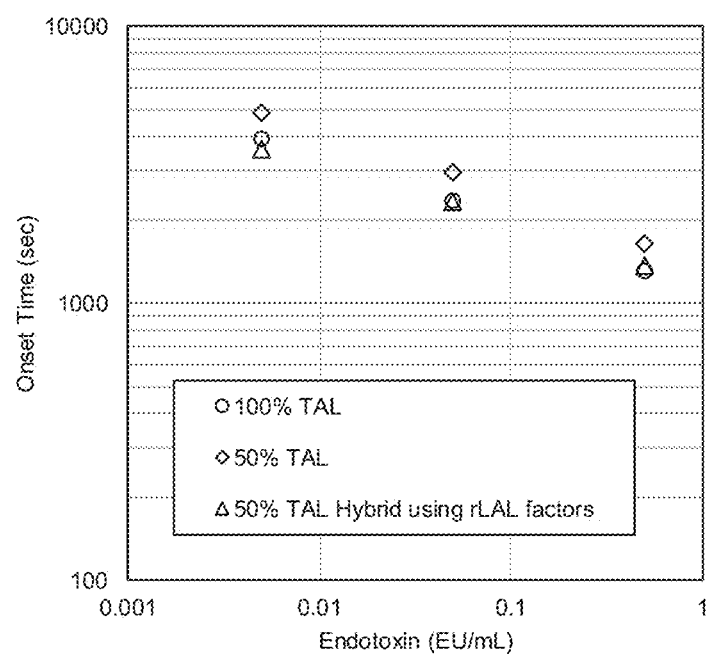
FIG. 9 is a line graph depicting onset time for the indicated reagents as a function of endotoxin concentration in a kinetic chromogenic assay (KCA).

100% TAL, 50% TAL, and 50% TAL-rLP Hybrid were tested in a KCA assay (generally as described in Example 2). Results are shown in FIG. 9. As depicted, the sensitivity of 50% TAL was lower than 100% TAL (with 50% TAL having 38% of the sensitivity of 100% TAL). However, 50% TAL-rLP Hybrid showed greater sensitivity than 100% TAL (with 50% TAL-rLP Hybrid having 113% of the sensitivity of 100% TAL).

100% TAL, 50% TAL, rLAL (as described in Example 7) and 50% TAL-rLP were also used to detect NEE in one of the water samples from Example 7. Results are shown in TABLE 8. Endotoxin values measured using 100% TAL were set to 100%. As depicted, 50% TAL-rLP had improved activity relative to 50% TAL or rLAL.

TABLE 8

| Reagent | Relative Activity |
| --- | --- |
| 100% TAL | 100% |
| 50% TAL | 68% |
| rLAL | 9% |
| 50% TAL-rLP Hybrid | 77% |

Together, these results show that the addition of rFB and/or rPCE (e.g., *Limulus* rFB and/or rPCE) to a native amebocyte lysate (e.g., native TAL) can reduce the amount of native amebocyte lysate required to detect endotoxin (e.g., in a KCA assay) while maintaining, or in certain instances even increasing, sensitivity of the amebocyte lysate.

Example 10

This example describes the addition of recombinant *Tachypleus tridentatus* factor B, and/or pro-clotting enzyme to crude *Limulus* amebocyte lysate (LAL), and the resulting endotoxin detection activity.

Recombinant *Tachypleus tridentatus* factor B (rFB) and proclotting enzyme (rPCE) were prepared as described in Example 8. Crude LAL was prepared as described in Example 2. This reagent is referred to as "100% LAL". A hybrid reagent, referred to as "50% LAL-rT Hybrid", was prepared by diluting 100% LAL two-fold and adding 0.1 U/mL *Tachypleus tridentatus* rFB and 100 U/mL *Tachypleus tridentatus* rPCE. A control reagent, referred to as "50% LAL" was also prepared by diluting 100% LAL two-fold without the addition of any recombinant proteins.

Figure 10:
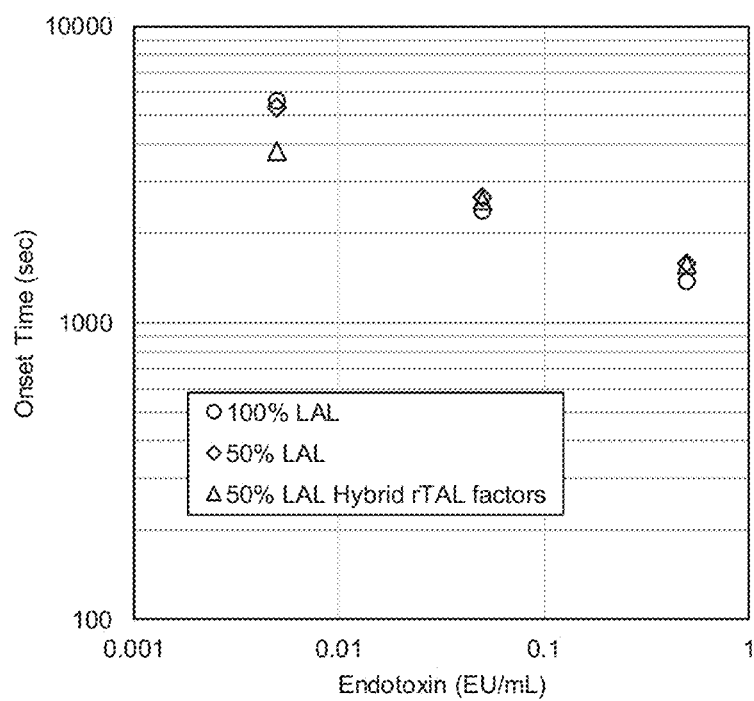
FIG. 10 is a line graph depicting onset time for the indicated reagents as a function of endotoxin concentration in a kinetic chromogenic assay (KCA).

100% LAL, 50% LAL, and 50% LAL-rT Hybrid were tested in a KCA assay (generally as described in Example 2). Results are shown in FIG. 10. As depicted, the sensitivity of 50% LAL was lower than 100% LAL (with 50% LAL having 77% of the sensitivity of 100% LAL). However, 50% LAL-rT Hybrid showed greater sensitivity than 100% LAL (with 50% LAL-rT Hybrid having 129% of the sensitivity of 100% LAL).

100% LAL, 50% LAL, rLAL (as described in Example 7) and 50% LAL-rT Hybrid were also used to detect NEE in one of the water samples from Example 7. Results are shown in TABLE 9. Endotoxin values measured using 100% LAL were set to 100%. As depicted, 50% LAL-rT Hybrid had comparable activity to 100% LAL, and greater activity than 50% LAL or rLAL.

TABLE 9

| Reagent | Relative Activity |
| --- | --- |
| 100% LAL | 100% |
| 50% LAL | 66% |
| rLAL | 9% |
| 50% LAL-rTAL Hybrid | 91% |

Together, these results show that the addition of rFB and/or rPCE (e.g., *Tachypleus tridentatus* rFB and/or rPCE) to a native amebocyte lysate (e.g., native LAL) can reduce the amount of native amebocyte lysate required to detect endotoxin (e.g., in a KCA assay) while maintaining, or in certain instances even increasing, sensitivity of the amebocyte lysate.

Example 11

This example provides a comparison of two forms of *Limulus* Factor C expressed in cell lines such that one cell line produced Factor C containing terminal sialic acid glycosylation, and the other produced Factor C without terminal sialic acid glycosylation, and demonstrates their respective biological activities in the presence of different salts.

The *Limulus* Factor C gene was expressed in two different host cell lines derived from HEK 293 cells. The first cell line was made using the Thermo Fisher Freestyle 293 system and produces expressed proteins fully glycosylated with the usual terminal sialic acid. The second cell line was derived from HEK 293 Gn TI⁻ cells, which lacks the enzymes necessary for addition of the terminal sialic acid.

*Limulus* Factor C (rFC) derived from HEK293 cells and HEK293 GnTI– cells was prepared as follows. The *Limulus* Factor C gene was cloned into both HEK293 cells and HEK293 GnTI– cells. Cultures of each were grown in Thermo Fisher Freestyle 293 medium according to manufacturer's instructions. Expressed Factor C from both lines were collected from the medium and concentrated by tangential flow filtration (TFF) for use in all experiments.

For gel electrophoresis, standard SDS polyacrylamide gel electrophoresis was performed, then stained for protein with SYPRO Orange. Fetuin, a glycoprotein, was included as a positive control for sialic acid.

For Western Blotting, the resulting gel was transferred to a nitrocellulose (NC) membrane by electroblotting and stained for sialic acid content by reaction with the sialic acid binding lectin from *Maackia amurensis*. The following protocol was used as set forth in TABLE 10.

TABLE 10

| Materials | | |
|---|---|---|
| NC membrane from electroblotting | | |
| Biotinylated *Maackia amurensis* Lectin II | Vector Lab | 1 mg/ml |
| Avidin-Horse Radish Peroxidase (HRP) | BioRad | 1:1000 |
| HRP Conjugate Substrate Kit | BioRad | |
| 1% Casein/1x TBS Blocker | BioRad | |
| TBS | BioRad | |
| TTBS | BioRad | |

| Procedure | | |
|---|---|---|
| Blocking: | Rinse NC membrane with TBS | 5 min × 2 |
| | Add 1% Casein/1x TBS | shake 1 hr/room temp. |
| 1$^{st}$ Reaction: | Prepare Biotin-Lectin solution (400 uL TBS) | shake 1 hr/ room temp. |
| | Rinse NC membrane with TTBS | |
| 2$^{nd}$ Reaction: | Add 20 uL Avidin-HRP in 20 mL TBS (1:1000) | shake 1 hr/ room temp. |
| | Rinse NC membrane with TTBS | 10 min. × 3 |
| | Rinse NC membrane with TBS | 10 min. × 2 |
| Color Development: | Mix from HRP Conjugate Substrate Kit HRP development buffer 1x 20 mL Reagent A, 0.12 mL Reagent B, 4.0 mL After color develops, rinse w/clean water, photograph | |

Figure 11:
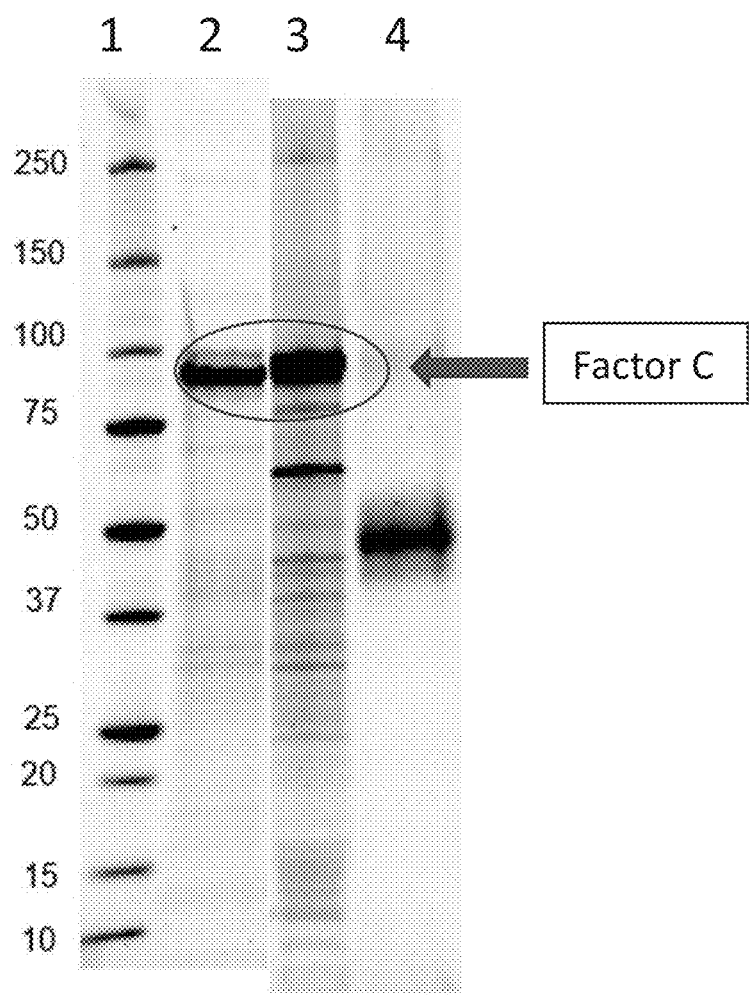
FIG. 11 is an image of a polyacrylamide electrophoresis gel where proteins are stained with SYPRO Orange. The bands of Factor C are circled. Lane 1 contains molecular weight markers. Lane 2 contains M21219-32 HEK293 GnTI- *Limulus* Factor C without sialic acid (2.7 µg loaded). Lane 3 contains M212199-28 HEK293 *Limulus* Factor C with sialic acid (3.0 µg loaded). Lane 4 contains Fetuin, a positive control sialic acid (10 µg loaded).
Figure 12:
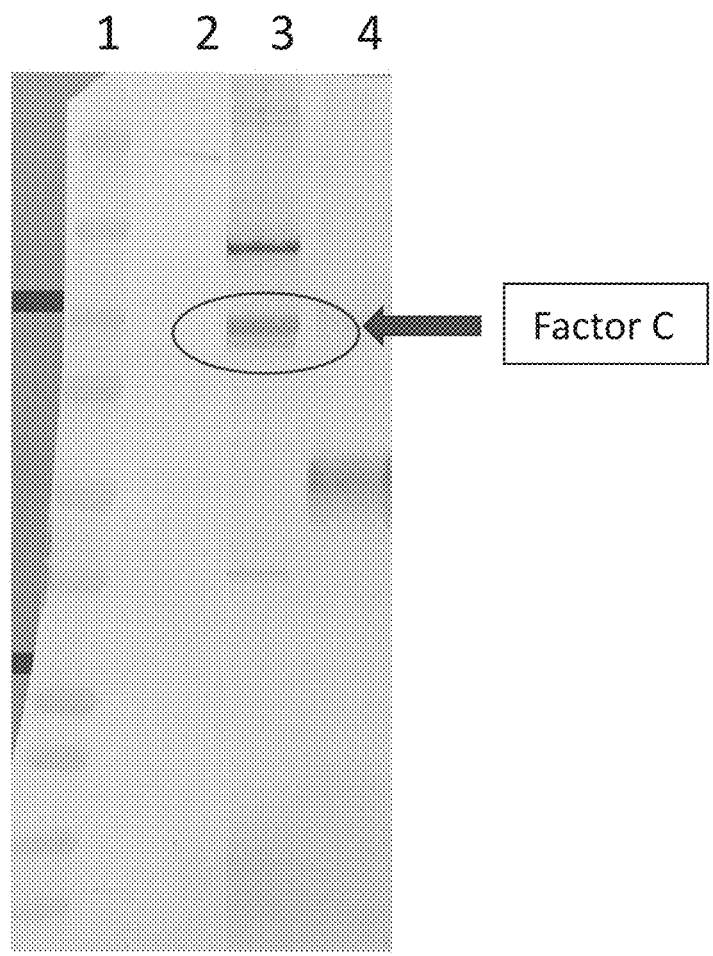
FIG. 12 is an image of a western blot stained with a sialic acid specific stain. Bands of Factor C are circled. Lane 1 contains molecular weight markers. Lane 2 contains M21219-32 HEK293 GnTI- *Limulus* Factor C without sialic acid (2.7 µg loaded). Lane 3 contains M212199-28 HEK293 *Limulus* Factor C with sialic acid (3.0 µg loaded). Lane 4 contains Fetuin, a positive control sialic acid (10 µg loaded).

Results of the gel electrophoresis are shown in FIG. 11, and the results of the western blot are shown in FIG. 12. The bands of Factor C are circled in each image. A comparison of FIG. 11 with FIG. 12 demonstrates the terminal sialic acid content of Factor C from HEK293 versus HEK293 GnTI⁻ cell lines. While the SYPRO Orange staining in FIG. 11 shows that Factor C is present in Lanes 2 and 3 along with the control Fetuin protein in Lane 4, FIG. 12 shows that the Factor C produced by the HEK 293 clone (Lane 3) was the only significant sialic acid staining other than the Fetuin positive control (Lane 4). No sialic acid binding was observed in the GnTI⁻ strains where Factor C migrates (Lane 2.)

In another experiment, a recombinant *Limulus* amebocyte lysate (LAL) was prepared using recombinant Factor C (rFC) derived from HEK293 cells (HEK293) or HEK293 GnTI- cells (GnTI⁻). Recombinant Factor B (rFB) and recombinant Proclotting Enzyme (rPCE) were added to standard formulation excipients for LAL, containing 0.1 M Tris-HCl buffer, pH 8.0. Then, rFC from HEK293 or GnTI⁻ was added to the solution to achieve functional recombinant LAL, one containing rFC from the HEK293 strain and one containing rFC from the GnTI- strain lacking terminal sialic acid glycosylation.

Figures 13, 14:
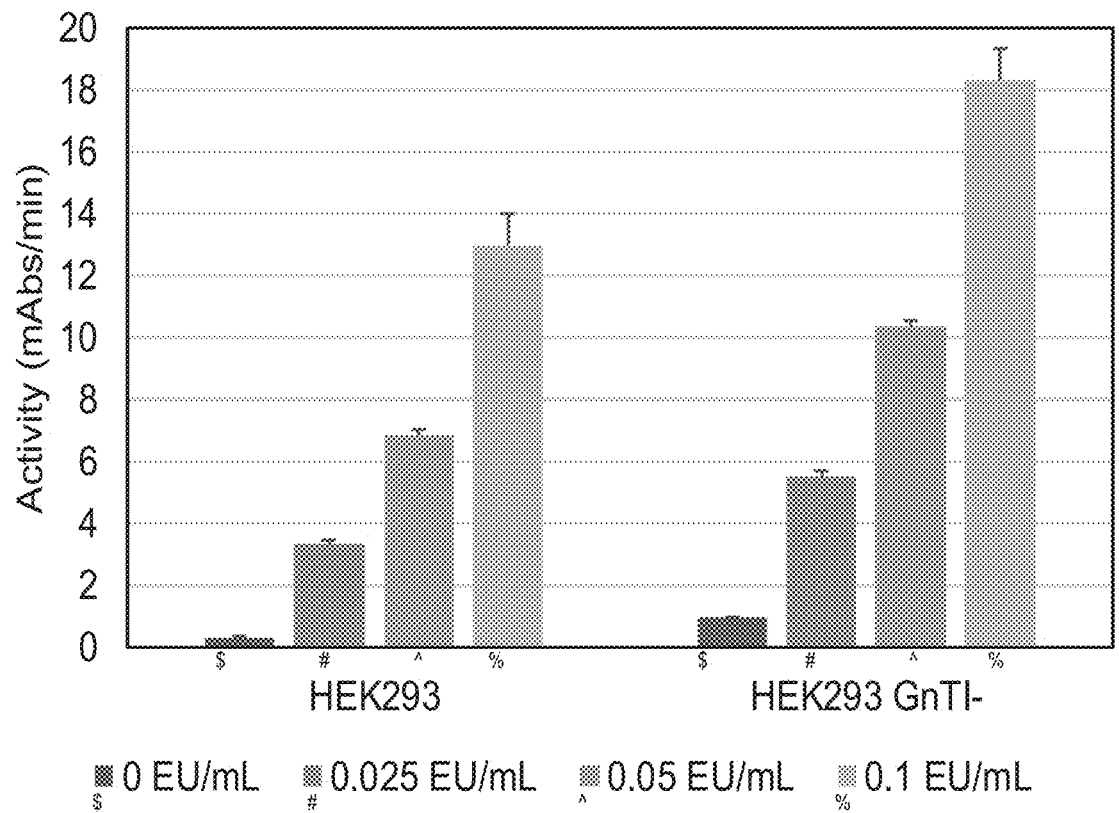
FIG. 13 is a standard curve for recombinant LAL using US Reference Standard Endotoxin (RSE) at 0, 0.025, 0.05, and 0.1 EU/mL and recombinant Factor C (rFC) produced in both HEK293 and HEK2GnTI− cell lines (n=2).
FIG. 14 shows in Tabular format the absorbance change rates of RSE dilutions (n=3) of the standard curve provided in FIG. 13.

Standard curves were established using US Reference Standard Endotoxin (RSE) at 0, 0.025, 0.05, and 0.1 EU/mL. RSE dilutions (0.1 mL) were mixed with the same volume of rLAL on a microplate. The absorbance change rates (mAbs/min) of the reaction mixtures were measured after 30 minutes reaction and the results are shown in FIGS. 13 and 14. Good dose-responses were observed with both HEK293 and GnTI- rFCs (FIG. 13). FIG. 14 shows the absorbance change rates for each endotoxin concentration. Reproducibility was also good (CV<5.3%).

Additionally, residual activity (endotoxin recovery) of endotoxin in salt solutions was measured. Endotoxin (RSE) was added to salt solutions at 0.05 EU/mL. The salt solutions used were 1.25% NaCl, 2.5% NaCl, 16 mM $MgSO_4$, 2.5 mM $CaCl_2$, 21 mM sodium citrate, and 52 mM sodium hydrogen carbonate. The residual activity was calculated by the averaged absorbance change (mAbs/min) with a salt solution containing 0.05 EU/mL by that with 0.05 EU/mL RSE.

Figure 15:
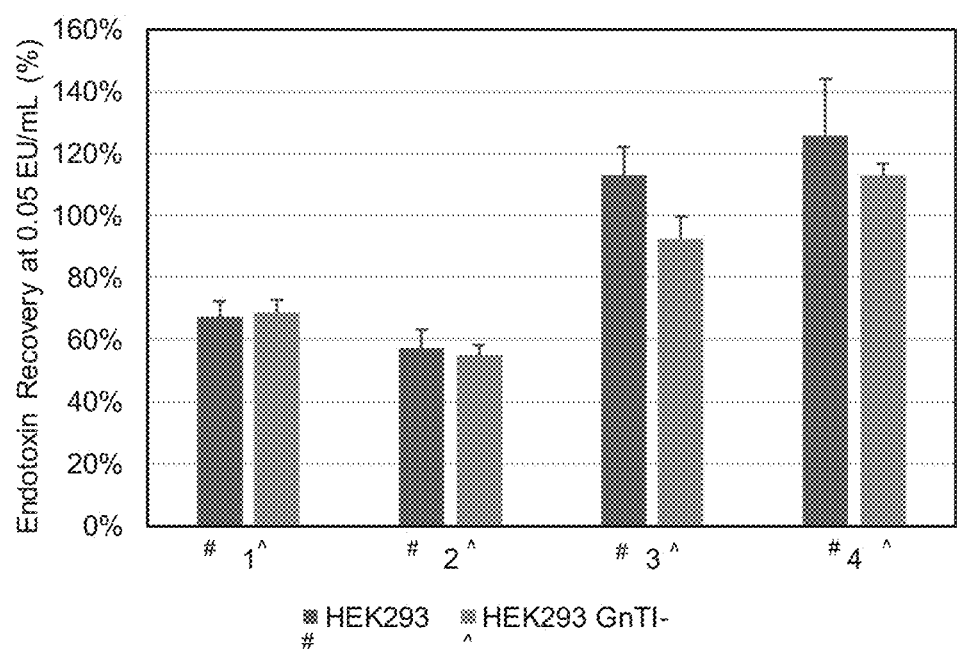
FIG. 15 is a bar graph showing residual activity (endotoxin recovery) of endotoxin in salt solutions (n=4) when spiked with endotoxin at a concentration of 0.05 EU/mL. rLALs containing rFCs expressed in HEK293 and GnTI− cells were used. Sample 1 contained 1.25% (214 mM) NaCl. Sample 2 contained 2.5% (428 mM) NaCl. Sample 3 contained 16 mM $MgSO_4$. Sample 4 contained 2.5 mM $CaCl_2$.

FIG. 15 shows the salt effects on the residual activity (Endotoxin Recovery) of spiked endotoxin as measured in NaCl, $MgSO_4$, and $CaCl_2$ solutions. The salt solutions were: 1—1.25% (214 mM) NaCl; 2—2.5% (428 mM) NaCl; 3—16 mM $MgSO_4$; and 4—2.5 mM $CaCl_2$. There was not a significant difference in endotoxin recovery except for 16 mM $MgSO_4$. The endotoxin recoveries in 16 mM $MgSO_4$ were 113% and 92%. Considering the variability and the official acceptance range (50%-200%), this difference is negligible in the endotoxin measurement.

Figure 16:
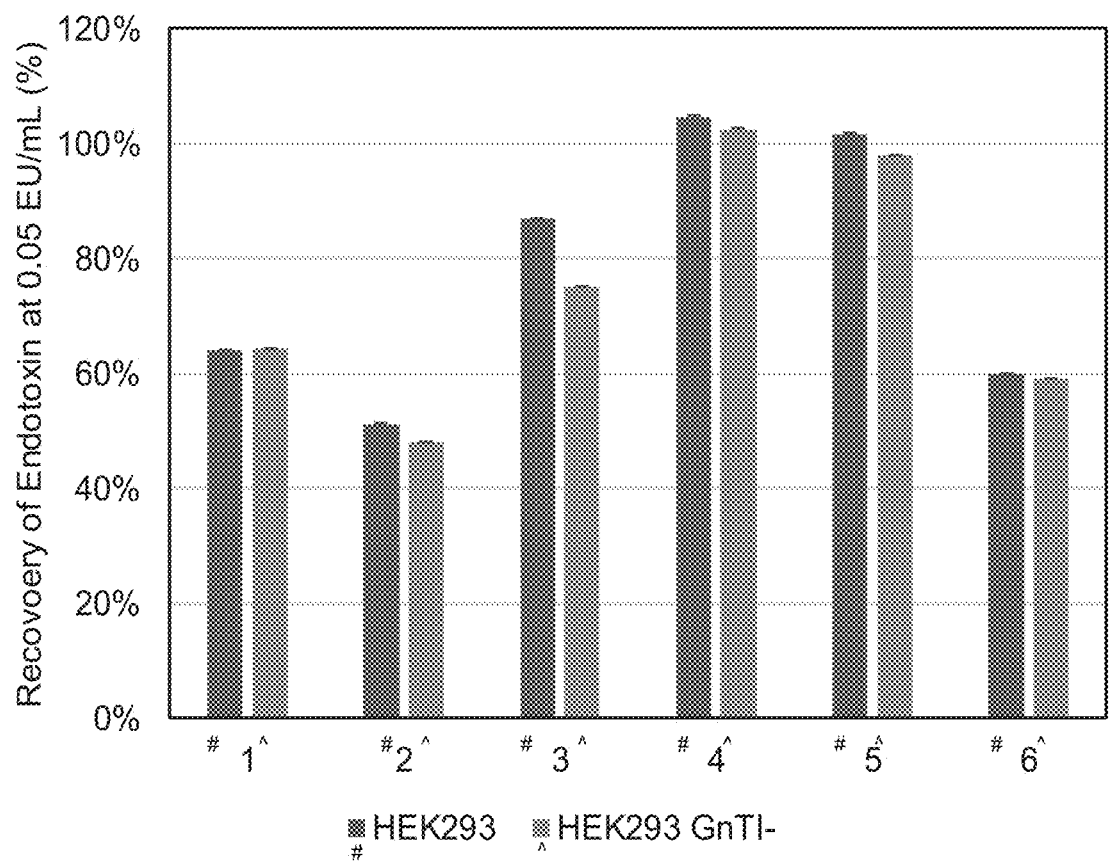
FIG. 16 is a bar graph showing the residual activity (endotoxin recovery) of endotoxin in salt solutions (n=2) when spiked with endotoxin at a concentration of 0.05 EU/mL. rLALs containing rFCs expressed in HEK293 and GnTI− cells were used. Sample 1 contained 1.25% (214 mM) NaCl; sample 2 contained 2.5% (428 mM) NaCl; sample 3 contained 16 mM $MgSO_4$; sample 4 contained 2.5 mM $CaCl_2$; sample 5 contained 21 mM sodium citrate; and sample 6 contained 52 mM sodium hydrogen carbonate.

FIG. 16 shows the salts' effects on the residual activity (Endotoxin Recovery) of spiked endotoxin as measured in NaCl, $MgSO_4$, $CaCl_2$, sodium citrate and sodium hydrogen carbonate solutions. The salt solutions were: 1—1.25% (214 mM) NaCl; 2—2.5% (428 mM) NaCl; 3—16 mM $MgSO_4$; 4—2.5 mM $CaCl_2$; 5—21 mM sodium citrate; and 6—52 mM sodium hydrogen carbonate. The results demonstrate that there was not a significant difference in endotoxin recovery between rLALs using rFCs expressed in HEK293 or GnTI- cell lines. The endotoxin recoveries in 16 mM $MgSO_4$ were 87% and 75%. Considering the variability and the official acceptance range (50%-200%), this difference is negligible in the endotoxin measurement.

Equivalent biological activity was observed in Factor C produced by either strain HEK293 or GnTi⁻, regardless of sialic acid content. There was no significant difference in salt effect between rLALs containing rFCs produced in HEK293 and GNTI- cell lines. The difference between these rFCs is the existence of terminal sialic acids. GnTI- cells lack N-acetylglucosaminyltransferase, and are unable to synthesize complex N-glycans.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

SEQUENCE LISTING

SEQ ID NO: 1

ATGGTGCTTGCCTCCTTTCTCGTGTCCGGTCTTGTGCTCGGCCTCCTCGCCCAAAAGATGCGAC

CCGTGCAGTCCAGAGGAGTGGACCTGGGCCTGTGCGACGATACCCGGTTCGAGTGCAAATGCGG

CGACCCGGGTTACGTGTTCAATGTGCCTGCGAAGCAGTGTACCTACTTTTACCGCTGGCGCCCT

TACTGCAAGCCATGCGACAAGCTTGAGGCTAAAGATGTGTGCCCCAAGTACAAGAGGTGCCAAG

AATGCCGCGCCGGCCTGGATTCATGCGTGAGCTGCCCCCCAAACAAATACGGCACTTGGTGCTC

CGGGGAGTGCCAGTGCAAGAACGGCGGAATCTGCGACCAGAGGACCGGGGCCTGCACTTGCCGG

GACCGCTACGAGGGGGTGCATTGCGAGATCCTGCAGGGTTGCCCGCTGCTGCAGTCCGACCCCC

AAGTGCAGGAGGTCAAGAACCCCCCAACGACCCGCAGACCATCGACTACTCCTGTTCACCTGG

GTTCAAGCTGAAGGGCGTGGCACGGATTACGTGCCTCCCCAACGGACAGTGGTCATCCTTCCCC

CCTAAGTGCATTCGGGAGTGCAGCATGGTGTCGAGCTTGGAACACGGAAAGGTCAACTCCCCGA

GCGCCGACCTGATTGAGGGGGCGACCCTTCGGTTCTCGTGCGACTCCCCCTATTACCTGATCGG

TCAGGAAACCCTGACGTGCCAGGGCAACGGCCAATGGTCGGGCAGATCCCGCAGTGTCAGAAG

CTCGTGTTTTGTCCCGATTTGGACCCAGTGTCCCATGCCGAACACCAGGTCAAGATCGGACTGG

AACAGAAATACGGACAGTTCCCCCAAGGCACTGAAGTCACTTACACTTGCACCGGAAACTACTT

CCTGATGGGCCTGGACACCCTCAAGTGCAATCCCGACGGATCCTGGTCGGGCACTCAGCCGTCC

TGCGTGAAAGTGGCAGACAGAGAAGTGAACTGTGATAGCAAAGCTGTGGACTTCCTGGACGACG

TGGGCGAACCGGTCCGCATCCACTGCCCGGCCGGGTGCAGCCTGACCGCGGGTACTGTCTGGGG

TACCGCCATCTATCATGAACTTTCGTCCGTCTGCCGGGCCGCCATTCACGCCGGAAAGGTCCCG

AATAGCGGCGGTGCAGTGCACGTCGTGAACAACGGACCCTACTCGGATTTCCTCGCCTCGGACT

TGAATGGCATTAAGTCCGACGAGCTGAAGTCCCTGGCCCAGTCCTTCCGGTTCGACTACGTGTC

ATCCAGCACGGCCGGACGGAAGTCGGGCTGCCCTGATGGCTGGTTCGAAATCGAAGAGAATTGT

GTCTACGTGACCTCAAAGCAGAGAGCCTGGGAACGGGCTCAGGGAGTCTGCACTAACATGGCTG

CCCGGTTGGCCGTGCTCGACAAGGATGTGATCCCGTCCTCGCTCACTGAAACCCTGCGGGGAAA

GGGACTGGCTACCACTTGGATCGGACTGCACAGGCTCGATGCGGACAACCACTTCATCTGGGAA

CTGATGGACCGCTCCTCCGTGGCCCTGAACGACAGCCTGACCTTCTGGGCCCCTGGAGAGCCAG

GAAACGAAACCAACTGCGTGTACCTGGACATCCAGGACCAACTGCAGCCTGTCTGGAAAACCAA

GTCGTGCTTTCAACCCTCCTCTTTCGTGTGCATGATGGACCTGAGCGATAAGAACAAGGCCAAG

TGCAAGGATCCCGGCCCGCTCGAGAACGGTCACGCGAAGCTGCACGGGCAGTCCATCGACGGCT

TCTATGCCGGTTCCTCCGTGCGCTACTCGTGTGAAGTGTTGCACTACCTGTCCGGTACCGAAAC

CGTGTCCTGTACCTCCAACGGGACTTGGTCGGCCCCGAAGCCACGCTGTATTAAGGTCATCACC

TGTCAGACTCCGCCTGTCCCGTCCTACGGGTCCGTGGATATCAAGCCCCCGAGCCGGACTAACT

CGATTAGCCGCGTGGGCTCACCCTTTCTGCGGCTCCCAAGGTTGCCGCTTCCGCTGGCCCGGGC

GGCCGGCCCGCCTCCGAAGCCTAGATCCGCGCCTCCGTCCACCGTGGATTTGTCCAGCAAAGTC

AAGCTCCCTGAGGGACATTACAGAGTGGGATCCCAGGCCATCTACACTTGCGAATCACGCTATT

ACGAGCTGCTCGGATCGCAAGGCAGACGCTGTGACAGCAACGGAAAGTGGTCGGGCAGACCGGC

CAGCTGTATTCCCGTGTGCGGGCGGAGCGACTCGCCTCGCTCCCCCTTCATCGTGAACGGAAAC

TCAACCGAAATCGGCCAGTGGCCGTGGCAGGCCGGAATCTCTCGGTGGCTGGCTGATCATAACA

TGTGGTTCCTGCAATGCGGGGGCGCCCTGCTGAACGAGAAGTGGATAATCACAGCCGCTCACTG

CGTGACATACTCGGCAACCGCCGAAATCATCGATCCCTCCCAATTCAAGTTCTACCTGGGAAAG

```
                        SEQUENCE LISTING

TACTACCGGGATGACTCTAAGGACGACGATTATGTGCAAGTCCGGGAAGCCATTGAGATCCACG

TGAACCCTAACTACGATCCGGGAAATCTGAACTTCGACATTGCGCTGATCCAGCTGAAAACCTC

CGTGGCGCTGACCACTCGCGTCCAGCCGATCTGCCTCCCCACTGACCTGACCACACGGGAGAAC

CTGAAGGAAGGGGCCCTGGCAGTCGTGACCGGATGGGGACTCAACGAGAACAACACCTACTCCG

AGATGATCCAGCAGGCCGTGCTCCCTGTGGTGGCGGCCAGCACCTGTGAACAGGGCTACCAGGA

CTCCGGCCTCCCACTGACTGTGACTGAGAACATGTTCTGTGCCGGGTACAAGCAGGGGCGCTAC

GACGCGTGTTCCGGCGACAGCGGCGGGCCACTGGTGTTCGCCGACGACTCGAGGACCGACCGGC

GCTGGGTGCTCGAGGGTATTGTGTCCTGGGGATCCCCCAACGGATGCGGGAAGTCCAACCAATA

CGGCGGATTCACCAAGGTCAACGTGTTCTTGTCCTGGATTCGCCAGTTCATCTGA
```
                                                   SEQ ID NO: 2
RGVDLGLCDDTRFECKCGDPGYVFNVPAKQCTYFYRWRPYCKPCDKLEAKDVCPKYKRCQECRA

GLDSCVSCPPNKYGTWCSGECQCKNGGICDQRTGACTCRDRYEGVHCEILQGCPLLQSDPQVQE

VKNPPNDPQTIDYSCSPGFKLKGVARITCLPNGQWSSFPPKCIRECSMVSSLEHGKVNSPSADL

IEGATLRFSCDSPYYLIGQETLTCQGNGQWSGQIPQCQKLVFCPDLDPVSHAEHQVKIGLEQKY

GQFPQGTEVTYTCTGNYFLMGLDTLKCNPDGSWSGTQPSCVKVADREVNCDSKAVDFLDDVGEP

VRIHCPAGCSLTAGTVWGTAIYHELSSVCRAATHAGKVPNSGGAVHVVNNGPYSDFLASDLNGI

KSDELKSLAQSFRFDYVSSTAGRKSGCPDGWFEIEENCVYVTSKQRAWERAQGVCTNMAARLA

VLDKDVIPSSLTETLRGKGLATTWIGLHRLDADNHFIWELMDRSSVALNDSLTFWAPGEPGNET

NCVYLDIQDQLQPVWKTKSCFQPSSFVCMMDLSDKNKAKCKDPGPLENGHAKLHGQSIDGFYAG

SSVRYSCEVLHYLSGTETVSCTSNGTWSAPKPRCIKVITCQTPPVPSYGSVDIKPPSRTNSISR

VGSPFLRLPRLPLPLARAAGPPPKPRSAPPSTVDLSSKVKLPEGHYRVGSQAIYTCESRYYELL

GSQGRRCDSNGKWSGRPASCIPVCGRSDSPRSPFIVNGNSTEIGQWPWQAGISRWLADHNMWFL

QCGGALLNEKWIITAAHCVTYSATAEIIDPSQFKFYLGKYYRDDSKDDDYVQVREAIEIHVNPN

YDPGNLNFDIALIQLKTSVALTTRVQPICLPTDLTTRENLKEGALAVVTGWGLNENNTYSEMIQ

QAVLPVVAASTCEQGYQDSGLPLTVTENMFCAGYKQGRYDACSGDSGGPLVFADDSRTDRRWVL

EGIVSWGSPNGCGKSNQYGGFTKVNVFLSWIRQFI (Residues 1-25 shown in bold represent the signal sequence)
                                                   SEQ ID NO: 3
MVLASFLVSGLVLGLLAQKMRPVQSRGVDLGLCDDTRFECKCGDPGYVFNVPAKQCTYFYRWRP

YCKPCDKLEAKDVCPKYKRCQECRAGLDSCVSCPPNKYGTWCSGECQCKNGGICDQRTGACTCR

DRYEGVHCEILQGCPLLQSDPQVQEVKNPPNDPQTIDYSCSPGFKLKGVARITCLPNGQWSSFP

PKCIRECSMVSSLEHGKVNSPSADLIEGATLRFSCDSPYYLIGQETLTCQGNGQWSGQIPQCQK

LVFCPDLDPVSHAEHQVKIGLEQKYGQFPQGTEVTYTCTGNYFLMGLDTLKCNPDGSWSGTQPS

CVKVADREVNCDSKAVDFLDDVGEPVRIHCPAGCSLTAGTVWGTAIYHELSSVCRAAIHAGKVP

NSGGAVHVVNNGPYSDFLASDLNGIKSDELKSLAQSFRFDYVSSTAGRKSGCPDGWFEIEENC

VYVTSKQRAWERAQGVCTNMAARLAVLDKDVIPSSLTETLRGKGLATTWIGLHRLDADNHFIWE

LMDRSSVALNDSLTFWAPGEPGNETNCVYLDIQDQLQPVWKTKSCFQPSSFVCMMDLSDKNKAK

CKDPGPLENGHAKLHGQSIDGFYAGSSVRYSCEVLHYLSGTETVSCTSNGTWSAPKPRCIKVIT

CQTPPVPSYGSVDIKPPSRTNSISRVGSPFLRLPRLPLPLARAAGPPPKPRSAPPSTVDLSSKV

KLPEGHYRVGSQAIYTCESRYYELLGSQGRRCDSNGKWSGRPASCIPVCGRSDSPRSPFIVNGN

STEIGQWPWQAGISRWLADHNMWFLQCGGALLNEKWIITAAHCVTYSATAEIIDPSQFKFYLGK

YYRDDSKDDDYVQVREAIEIHVNPNYDPGNLNFDIALIQLKTSVALTTRVQPICLPTDLTTREN

LKEGALAVVTGWGLNENNTYSEMIQQAVLPVVAASTCEQGYQDSGLPLTVTENMFCAGYKQGRY

DACSGDSGGPLVFADDSRTDRRWVLEGIVSWGSPNGCGKSNQYGGFTKVNVFLSWIRQFI

SEQ ID NO: 4

ATGGCCTGGATCTGTGTCATTACCCTTTTCGCTCTCGCCTCGTCTACTCTGTCCAACAAAGTGT

CGAGGGTCGGAATCATCTTCCCCAAGACTCAGAACGACAACAAGCAGTGCACGGCTAAGGGTGG

ACTCAAGGGCAGCTGCAAATCCCTCACTGACTGCCCCGCCGTGCTGGCGACCCTTAAGGACAGC

TTCCCTGTCGTGTGTAGCTGGAATGGCCGGTTCCAACCGATTGTGTGCTGTCCGGACGCCGCCG

CCCCTTCCGTGACAACTACCGTGACCACTATCGTGCCGACCAAGGAAACTAAGATCCCTAGACT

GCATATCCCGGGCTGCGGGAAACGGAAAGTCAACGTGGACATCACCACCATCGGACGGTCCGGT

AGCCCGATCCTGCCGCCCATTAGCACGTCACAGGACCTGAAGGGGGGCCGCGGAATCATTGCCG

GCGGAGTGGAAGCGAAGATTGGGGCGTGGCCCTGGATGGCCGCAGTGTTCGTGAAGAACTTTGG

CATTGGAAGATTCCACTGCGCGGGATCCATCATTTCGTCCAAGTACATTCTGTCCGCCGCCCAC

GCCTTCCTGATCGGCGGCCGCAAGCTGACCCCCACCCGCTTGGCCGTGCGCGTGGGCGGACACT

ACGTCAAGATGGGCCAAGAGTACCACGTGGAAGATGTCATCATCCACCCTGACTACGTGGAACG

GGAGAACTACAACGACATCGCTATCATCGTGCTGAAGGAGGAGCTGAACTTCACCGACCTCGTG

CGCCCAATCTGCCTGCCGGATCCAGAGGCCGTGACCGATTCACTCAAGGGTCGGAGAGTGACCG

TCGCCGGTTGGGGGGACCTCGACTTCGCGGGCCCCCGGTCCCAAGTGCTGCGGGAGGTGTCCAT

ACCAGTGGTGCCTATTGGCGATTGCAACAAGGCATATCAGAAGCTCAACACCTTGGCTCTGAAG

AACGGAATTACCAAGAAGTTCATCTGCGCCGGGCTGGAAGAAGGGGGAAAGGACGCGTGCCAGG

GCGATTCGGGTGGACCCCTGATGCTGGTCAACAACTCATCGTGGATCGTGACCGGAGTGGTGTC

CTTCGGACATAAGTGCGCCGAAGAAGGGTTTCCGGGAGTCTACACCAGGGTGGTGTCCTACCTG

GAGTGGATCGCAAAGGTCACCAATTCCTTGGATCAGACCGTCACTAACTAA

SEQ ID NO: 5

IIFPKTQNDNKQCTAKGGLKGSCKSLTDCPAVLATLKDSFPVVCSWNGRFQPIVCCPDAAAPSV

TTTVTTIVPTKETKIPRLHIPGCGKRKVNVDITTIGRSGSPILPPISTSQDLKGGRGIIAGGVE

AKIGAWPWMAAVFVKNFGIGRFHCAGSIISSKYILSAAHAFLIGGRKLTPTRLAVRVGGHYVKM

GQEYHVEDVIIHPDYVERENYNDIAIIVLKEELNFTDLVRPICLPDPEAVTDSLKGRRVTVAGW

GDLDFAGPRSQVLREVSIPVVPIGDCNKAYQKLNTLALKNGITKKFICAGLEEGGKDACQGDSG

GPLMLVNNSSWIVTGVVSFGHKCAEEGFPGVYTRVVSYLEWIAKVTNSLDQTVTN (Residues 1-25 shown in bold represent the signal sequence)

SEQ ID NO: 6

MAWICVITLFALASSTLSNKVSRVGIIFPKTQNDNKQCTAKGGLKGSCKSLTDCPAVLATLKDS

FPVVCSWNGRFQPIVCCPDAAAPSVTTTVTTIVPTKETKIPRLHIPGCGKRKVNVDITTIGRSG

SPILPPISTSQDLKGGRGIIAGGVEAKIGAWPWMAAVFVKNFGIGRFHCAGSIISSKYILSAAH

AFLIGGRKLIPTRLAVRVGGHYVKMGQEYHVEDVIIHPDYVERENYNDIAIIVLKEELNFTDLV

RPICLPDPEAVTDSLKGRRVTVAGWGDLDFAGPRSQVLREVSIPVVPIGDONKAYQKLNTLALK

NGITKKFICAGLEEGGKDACQGDSGGPLMLVNNSSWIVTGVVSFGHKCAEEGFPGVYTRVVSYL

EWIAKVTNSLDQTVTN

SEQUENCE LISTING

SEQ ID NO: 7
ATGGGAATCTTGCCCTCGCCCGGAATGCCTGCCCTGCTTAGCCTCGTGTCACTCCTGTCCGTCC

TGCTCATGGGCTGCGTGGCCTCCTCACTGGGACGCCAGCGGAGACAGTTCGTGTTCCCGGATGA

CGAAGAGTCCTGTAGCAACCGGTTTACCAACGACGGGATCTGCAAGGACGTGCTGAACTGCCGC

GATCTGCTGCAGAAGAATGACTACAACCTCTTGAAGGAATCCATCTGCGGCTTCGAAGGGATCA

CCCCTAAAGTCTGCTGTCCAAAGCAATCCATTGTGAACCCCATCACCGAAGCCCCGCCTAAGAC

CACCACTACTGAGAGGCCTCCGATCCGGATCCCCTCCAACCTCCCGAAGCAGTGCGGAAATCGG

AACATCACTACCACTAGGATCATCGGCGGACAGGAAGCCACTCCGGGAGCCTGGCCGTGGATGG

CAGCCGTGTACATTAAGCAGGGGGGGATTCGGTCCGTGCAGTGCGGTGGCGCCCTTGTGACCAA

CAGACACGTGATCACCGCCTCACACTGCGTCGTGAATTCCCTGGGTACCGATGTGATGAGGGCT

GATGTGTTCTCCGTGCGGCTGGGAGAACATAACCTGTACAGCACTAACGACTCGTCAGACCCAA

TCGACTTCGCCGTGACGAGCGTGAAGCACCATGAAAACTTCGTGCTGGCCACCTACCTCAACGA

CATCGCGATCCTGAAGCTGAACGACACTGTCACCTTCACACACAAGATTAAGCCGATTTGCCTC

CCTTACGAGTCCCTGCGCTATGAGGACCTCGCTATGCGCAACCCCTTCGTGGCCGGATGGGGCA

CTACCGCGTTCAACGGACCGAGCAGCGCTGTCCTGAGAGAAGTGCAACTCCCAATCTGGGGTCA

CGAGCCGTGCCGCCAAGCGTACGAGAAAGACCTGAACATCACCAACGTGTATATGTGCGCGGGC

TACGCCGACGGTGGAAAGGACGCATGCCAGGGCGATTCTGGCGGCCCCATGATGCTGCCTGACA

AGTCCGGGAACTTCTACCTGGTCGGAATCGTGTCGTTCGGAAAGAAATGCGCCCTGCCCGGCTT

TCCCGGAGTGTACACCAAGGTCACCGAATTTTTGGATTGGATTGCCGTGAACATGGTCTAA

SEQ ID NO: 8
SSLGRQRRQFVFPDDEESCSNRFTNDGICKDVLNCRDLLQKNDYNLLKESICGFEGITPKVCCP

KQSIVNPITEAPPKTTTTERPPIRIPSNLPKQCGNRNITTTRIIGGQEATPGAWPWMAAVYIKQ

GGIRSVQCGGALVTNRHVITASHCVVNSLGTDVMRADVFSVRLGEHNLYSTNDSSDPIDFAVTS

VKHHENFVLATYLNDIAILKLNDTVTFTHKIKPICLPYESLRYEDLAMRNPFVAGWGTTAFNGP

SSAVLREVQLPIWGHEPCRQAYEKDLNITNVYMCAGYADGGKDACQGDSGGPMMLPDKSGNFYL

VGIVSFGKKCALPGFPGVYTKVTEFLDWIAVNMV (Residues 1-28 shown in bold represent the signal sequence)
SEQ ID NO: 9
MGILPSPGMPALLSLVSLLSVLLMGCVASSLGRQRRQFVFPDDEESCSNRFTNDGICKDVLNCR

DLLQKNDYNLLKESICGFEGITPKVCCPKQSIVNPITEAPPKTTTTERPPIRIPSNLPKQCGNR

DVFSVRLGEHNLYSTNDSSDPIDFAVTSVKHHENFVLATYLNDIAILKLNDTVTFTHKIKPICL

PYESLRYEDLAMRNPFVAGWGTTAFNGPSSAVLREVQLPIWGHEPCRQAYEKDLNITNVYMCAG

YADGGKDACQGDSGGPMMLPDKSGNFYLVGIVSFGKKCALPGFPGVYTKVTEFLDWIAVNMV

SEQ ID NO: 10
ATGAAGTTCCTCGTCAACGTCGCCCTCGTGTTTATGGTGGTGTATATTAGCTACATCTATGCTC

GTGGCGTCGATCTGGGCCTGTGCGATGAGACCCGCTTCGAATGTAAGTGCGGCGACCCCGGCTA

TGTGTTCAACGTCCCCATGAAGCAGTGCACCTACTTCTACCGCTGGCGCCCCTACTGTAAGCCT

TGCGATGACCTGGAAGCTAAAGATATTTGCCCTAAGTATAAGCGCTGCCAAGAATGTAAGGCTG

GTCTGGATTCCTGCGTCACCTGTCCCCCTAACAAGTATGGCACCTGGTGTTCCGGTGAATGCCA

GTGCAAAAACGGCGGCATCTGCGATCAGCGTACTGGCGCTTGCACCTGCCGTGATCGCTACGAG

GGCGCCCACTGTGAAATTCTGAAAGGCTGTCCTCTGCTGCCTTCCGATAGCCAAGTGCAGGAGG

-continued

SEQUENCE LISTING

```
TGCGTAACCCCCCTGACAACCCTCAGACCATCGATTATAGCTGCTCCCCCGGCTTCAAGCTGAA

GGGCGTGGCCCGTATTAGCTGTCTGCCCAACGGTCAGTGGAGCTCCTTTCCCCCCAAGTGCATC

CGTGAATGTGCCAAGGTCTCCTCCCCCGAACACGGCAAGGTCAACGCTCCCTCCGGCAACATGA

TCGAAGGCGCCACCCTCCGTTTTTCCTGCGACTCCCCTTACTACCTCATCGGCCAGGAGACCCT

GACTTGTCAGGGCAATGGCCAGTGGAGCGGTCAAATCCCTCAGTGCAAGAAGCTGGTGTTCTGT

CCTGACCTCGATCCCGTGAACCACGCTGAGCACCAAGTGAAGATCGGCGTGGAACAAAAGTACG

GTCAGTTCCCTCAGGGCACTGAGGTCACTTACACTTGCTCCGGCAACTACTTCCTGATGGGCTT

CAACACCCTGAAATGTAACCCCGACGGTTCCTGGTCCGGTTCCCAGCCCTCCTGCGTGAAAGTC

GCTGACCGTGAAGtcgaCTGTGACAGCAAAGCCGTGGACTTCCTGGACGACGTGGGCGAGCCTG

TGCGTATTCACTGTCCCGCTGGCTGTAGCCTGACTGCCGGTACCGTGTGGGGTACTGCTATCTA

CCACGAGCTCTCCAGCGTGTGCCGCGCTGCTATCCACGCTGGCAAGCTGCCTAACAGCGGCGGT

GCTGTCCACGTGGTGAACAACGGTCCCTACTCCGACTTCCTCGGTAGCGACCTGAACGGTATCA

AAAGCGAGGAACTGAAGTCCCTGGCCCGTAGCTTTCGCTTCGACTACGTGTCCTCCTCCACCGC

TGGCCGTAGCGGCTGTCCTGATGGCTGGTTTGAGGTGGAAGAGAATTGTGTGTACGTGACCTCC

AAGCAGCGTGCTTGGGAGCGTGCTCAGGGTGTCTGTACCAATATGGCCGCCCGTCTGGCTGTCC

TCGATAAGGATCTCATCCCTTCCTCCCTCACCGAGACTCTGCGCGGTAAGGGCCTGACCACTAC

CTGGATCGGTCTCCACCGCCTGGACGCTGAGAAGCCTTTCGTCTGGGAGCTCATGGACCGCAGC

AACGTGGTGCTGAACGACAACCTGACCTTCTGGGCCAGCGGCGAGCCTGGCAATGAAACCAACT

GCGTGTACCTGGACATCCGTGATCAGCTCCAGCCCGTGTGGAAGACCAAGAGCTGCTTCCAGCC

CTCCAGCTTTGCTTGCATGATGGATCTCTCCGACCGCAACAAGGCTAAATGTGATGATCCCGGC

CCCCTGGAGAACGGCCATGCCACTCTGCATGGCCAGAGCATCGACGGTTTCTACGCTGGTTCCT

CCATCCGCTACTCCTGCGAAGTGCTCCACTACCTGTCCGGCACCGAGACCGTGACCTGTACTAC

CAACGGTACTTGGAGCGCTCCTAAACCCCGCTGTATCAAGGTGATTACCTGTCAGAACCCTCCT

GTCCCCAGCTACGGCTCCGTGGAAATCAAGCCCCCCAGCCGTACTAATAGCATCAGCCGTGTCG

GTTCCCCTTTCCTGCGTCTGCCTCGTCTGCCCCTGCCTCTCGCTCGCGCTGCTAAGCCTCCCCC

TAAGCCCCGTTCCAGCCAGCCTAGCACTGTGGATCTCGCTAGCAAAGTGAAACTCCCCGAGGGT

CACTATCGTGTGGGCTCCCGCGCCATTTACACCTGCGAGAGCCGCTACTACGAGCTCCTGGGCA

GCCAGGGTCGTCGTTGCGACAGCAACGGTAACTGGAGCGGTCGCCCTGCCAGCTGCATTCCCGT

GTGCGGTCGCAGCGACTCCCCTCGCAGCCCTTTCATCTGGAACGGCAACAGCACCGAGATCGGT

CAGTGGCCCTGGCAAGCTGGCATTAGCCGCTGGCTCGCTGATCACAACATGTGGTTCCTCCAAT

GTGGCGGCAGCCTGCTGAACGAGAAGTGGATCGTGACTGCCGCTCACTGCGTGACCTACAGCGC

CACCGCTGAGATCATCGACCCCTCCCAATTTAAGATCTACCTCGGCAAGTACTACCGCGACGAT

AGCCGCGACGACGATTATGTGCAAGTCCGCGAAGCTCTCGAAATTCACGTGAACCCTAACTACG

ATCCCGGTAACCTGAACTTCGACATTGCCCTGATCCAGCTGAAGACCCCTGTGACCCTCACCAC

TCGCGTCCAGCCTATCTGCCTCCCCACCGACATTACCACTCGCGAACATCTGAAAGAAGGTACC

CTGGCCGTCGTGACCGGCTGGGGCCTCAACGAAAACAACACTTACAGCGAGATGATCCAGCAGG

CTGTGCTGCCTGTCGTGGCTGCTAGCACCTGTGAGGAAGGCTACAAAGAGGCCGATCTCCCCCT

GACCGTCACCGAGAACATGTTTTGCGCTGGTTACAAAAAGGGCCGCTACGACGCCTGCAGCGGT
```

-continued

SEQUENCE LISTING

GATAGCGGTGGCCCTCTCGTGTTCGCCGATGATTCCCGTACCGAACGTCGCTGGGTGCTCGAGG

GCATTGTGTCCTGGGGTAGCCCTTCCGGCTGTGGCAAGGCTAACCAATACGGCGGCTTCACCAA

GGTGAACGTGTTCCTGTCCTGGATTCGTCAGTTCATCTAATGA

SEQ ID NO: 11
RGVDLGLCDETRFECKCGDPGYVFNVPMKQCTYFYRWRPYCKPCDDLEAKDICPKYKRCQECKA

GLDSCVTCPPNKYGTWCSGECQCKNGGICDQRTGACTCRDRYEGAHCEILKGCPLLPSDSQVQE

VRNPPDNPQTIDYSCSPGFKLKGVARISCLPNGQWSSFPPKCIRECAKVSSPEHGKVNAPSGNM

IEGATLRFSCDSPYYLIGQETLTCQGNGQWSGQIPQCKKLVFCPDLDPVNHAEHQVKIGVEQKY

GQFPQGTEVTYTCSGNYFLMGFNTLKCNPDGSWSGSQPSCVKVADREVDCDSKAVDFLDDVGEP

VRIHCPAGCSLTAGTVWGTAIYHELSSVCRAAIHAGKLPNSGGAVHVVNNGPYSDFLGSDLNGI

KSEELKSLARSFRFDYVSSSTAGRSGCPDGWFEVEENCVYVTSKQRAWERAQGVCTNMAARLAV

LDKDLIPSSLTETLRGKGLTTTWIGLHRLDAEKPFVWELMDRSNVVLNDNLTFWASGEPGNETN

CVYLDIRDQLQPVWKTKSCFQPSSFACMMDLSDRNKAKCDDPGPLENGHATLHGQSIDGFYAGS

SIRYSCEVLHYLSGTETVTCTTNGTWSAPKPRCIKVITCQNPPVPSYGSVEIKPPSRTNSISRV

GSPFLRLPRLPLPLARAAKPPPKPRSSQPSTVDLASKVKLPEGHYRVGSRAIYTCESRYYELLG

SQGRRCDSNGNWSGRPASCIPVCGRSDSPRSPFIWNGNSTEIGQWPWQAGISRWLADHNMWFLQ

CGGSLLNEKWIVTAAHCVTYSATAEIIDPSQFKIYLGKYYRDDSRDDDYVQVREALEIHVNPNY

DPGNLNFDIALIQLKTPVTLTTRVQPICLPTDITTREHLKEGTLAVVTGWGLNENNTYSEMIQQ

AVLPVVAASTCEEGYKEADLPLTVTENMFCAGYKKGRYDACSGDSGGPLVFADDSRTERRWVLE

GIVSWGSPSGCGKANQYGGFTKVNVFLSWIRQFI (Residues 1-21 in bold represent the signal sequence)

SEQ ID NO: 12
MKFLVNVALVFMVVYISYIYARGVDLGLCDETRFECKCGDPGYVFNVPMKQCTYFYRWRPYCKP

CDDLEAKDICPKYKRCQECKAGLDSCVTCPPNKYGTWCSGECQCKNGGICDQRTGACTCRDRYE

GAHCEILKGCPLLPSDSQVQEVRNPPDNPQTIDYSCSPGFKLKGVARISCLPNGQWSSFPPKCI

RECAKVSSPEHGKVNAPSGNMIEGATLRFSCDSPYYLIGQETLTCQGNGQWSGQIPQCKKLVFC

PDLDPVNHAEHQVKIGVEQKYGQFPQGTEVTYTCSGNYFLMGFNTLKCNPDGSWSGSQPSCVKV

ADREVDCDSKAVDFLDDVGEPVRIHCPAGCSLTAGTVWGTAIYHELSSVCRAAIHAGKLPNSGG

AVHVVNNGPYSDFLGSDLNGIKSEELKSLARSFRFDYVSSSTAGRSGCPDGWFEVEENCVYVTS

KQRAWERAQGVCTNMAARLAVLDKDLIPSSLTETLRGKGLTTTWIGLHRLDAEKPFVWELMDRS

NVVLNDNLTFWASGEPGNETNCVYLDIRDQLQPVWKTKSCFQPSSFACMMDLSDRNKAKCDDPG

PLENGHATLHGQSIDGFYAGSSIRYSCEVLHYLSGTETVTCTTNGTWSAPKPRCIKVITCQNPP

VPSYGSVEIKPPSRTNSISRVGSPFLRLPRLPLPLARAAKPPPKPRSSQPSTVDLASKVKLPEG

HYRVGSRAIYTCESRYYELLGSQGRRCDSNGNWSGRPASCIPVCGRSDSPRSPFIWNGNSTEIG

QWPWQAGISRWLADHNMWFLQCGGSLLNEKWIVTAAHCVTYSATAEIIDPSQFKIYLGKYYRDD

SRDDDYVQVREALEIHVNPNYDPGNLNFDIALIQLKTPVTLTTRVQPICLPTDITTREHLKEGT

LAVVTGWGLNENNTYSEMIQQAVLPVVAASTCEEGYKEADLPLTVTENMFCAGYKKGRYDACSG

DSGGPLVFADDSRTERRWVLEGIVSWGSPSGCGKANQYGGFTKVNVFLSWIRQFI

SEQ ID NO: 13
ATGGACATGCGCGTGCCTGCCCAACTGCTCGGCCTGCTGCTGCTGTGGTTCCCGGGTAGCCGCT

GTGTGGGGGTGCTGTTCCCCAAGACCCGGAACGACAACGAATGCACTGCCAGGGGTGGATTGAA

-continued

SEQUENCE LISTING

```
GGGGTCCTGCAAGAGCCTGATCGACTGCCCGTCGGTGCTTGCCACCCTGAAGGACTCCTTTCCT
GTCGTGTGCTCCTGGAACGGCAGATTCCAGCCAATTGTGTGCTGTCCGGATGCAATTGCCCCCC
CACCTGTGACCACCACCGCCGTGACCGTGATCTCTACCAAGGAACCCAAGCTGCCTCGGCTCCA
CATCAGCGGTTGTGGGAAGCGGAAGGTCAAGATTGACATTACCACTGTGGGACGCTCAGGATCA
CCGATTCTGCCCCCGATCTCCACCCCGCAAAACTCCACTGGTGGCAGGGGCATCATTGCCGGTG
GAGTGGAAGCGAAGATCGGAGCCTGGCCTTGGATGGCGGCGGTGTTTGTGAAAAACTTCGGAAT
CGGGCGGTTCCACTGCGCTGGTTCGATCATCTCCAACAAGTACATCCTGTCCGCCGCACATGCC
TTCCTGATCGGAGGCCGGAAGTTGACCCCCACGAGACTGGCCGTCAGAGTCGGAGGGCATTACA
TCAAGCGCGGACAGGAATACCCCGTGAAGGACGTGATAATCCACCCCCACTACGTGGAAAAGGA
GAACTACAATGACATCGCCATTATCGAGCTGAAGGAGGAGCTGAACTTTACCGATCTTGTGAAC
CCCATCTGCCTCCCTGACCCCGAGACAGTGACCGACCCACTCAAAGACCGCATCGTGACTGCAG
CTGGATGGGGCGATCTGGACTTCAGCGGACCGAGAAGCCAGGTCCTGCGGGAGGTGTCAATCCC
GGTGGTGCCAGTCGACAAATGCGATCAGGCCTACGAGAAGCTGAACACTCCCTCCCTCAAAAAC
GGGATCACTAACAACTTCCTGTGCGCGGGACTTGAAGAAGGCGGAAAGGACGCCTGTCAGGGCG
ATTCCGGCGGACCTCTGATGCTCGTGAACAATACTCGGTGGATTGTCGTCGGCGTGGTGTCCTT
CGGACATAAGTGCGCCGAGGAAGGCTACCCTGGCGTCTATTCCCGCGTGGCCTCCTACCTGGAC
TGGATTGCCAAGGTCACCAACTCGCTCGACCATGCCGTGACTAACTGA
```

SEQ ID NO: 14
```
VGVLFPKTRNDNECTARGGLKGSCKSLIDCPSVLATLKDSFPVVCSWNGRFQPIVCCPDAIAPP
PVTTTAVTVISTKEPKLPRLHISGCGKRKVKIDITTVGRSGSPILPPISTPQNSTGGRGIIAGG
VEAKIGAWPWMAAVFVKNFGIGRFHCAGSIISNKYILSAAHAFLIGGRKLTPTRLAVRVGGHYI
KRGQEYPVKDVIIHPHYVEKENYNDIAIIELKEELNFTDLVNPICLPDPETVTDPLKDRIVTAA
GWGDLDFSGPRSQVLREVSIPVVPVDKCDQAYEKLNTPSLKNGITNNFLCAGLEEGGKDACQGD
SGGPLMLVNNTRWIVVGVVSFGHKCAEEGYPGVYSRVASYLDWIAKVTNSLDHAVTN
```
(Residues 1-22 represent the signal sequence)

SEQ ID NO: 15
```
MDMRVPAQLLGLLLLWFPGSRCVGVLFPKTRNDNECTARGGLKGSCKSLIDCPSVLATLKDSFP
VVCSWNGRFQPIVCCPDAIAPPPVTTTAVTVISTKEPKLPRLHISGCGKRKVKIDITTVGRSGS
PILPPISTPQNSTGGRGIIAGGVEAKIGAWPWMAAVFVKNFGIGRFHCAGSIISNKYILSAAHA
FLIGGRKLTPTRLAVRVGGHYIKRGQEYPVKDVIIHPHYVEKENYNDIAIIELKEELNFTDLVN
PICLPDPETVTDPLKDRIVTAAGWGDLDFSGPRSQVLREVSIPVVPVDKCDQAYEKLNTPSLKN
GITNNFLCAGLEEGGKDACQGDSGGPLMLVNNTRWIVVGVVSFGHKCAEEGYPGVYSRVASYLD
WIAKVTNSLDHAVTN
```

SEQ ID NO: 16
```
ATGCTGGTCAACAATGTCTTTTCCCTGCTCTGCTTCCCTCTCCTGATGTCCGTCGTGCGCTGCT
CCACCCTCTCGAGACAGCGGCGCCAGTTTGTGTTCCCTGATGAAGAGGAACTGTGTTCCAACCG
GTTCACCGAAGAGGGAACTTGCAAGAACGTGCTGGACTGCCGCATCCTGCTTCAAAAGAACGAC
TACAACCTTCTCAAGGAGTCAATCTGCGGTTTCGAAGGGATTACCCCAAAAGTCTGCTGCCCGA
AGTCCTCGCACGTGATCTCAAGCACCCAGGCACCCCCTGAAACTACCACTACTGAGCGGCCCCC
GAAGCAAATTCCCCCGAACTTGCCGGAAGTCTGCGGCATCCACAACACCACCACCACTAGGATC
```

-continued

SEQUENCE LISTING

ATCGGGGGAGAGAAGCCCCTATCGGCGCCTGGCCCTGGATGACCGCTGTGTACATTAAGCAGG

GCGGTATCCGGAGCGTGCAGTGCGGTGGAGCTCTGGTCACCAATCGCCACGTGATCACAGCGTC

ACACTGCGTCGTGAACTCGGCGGGTACCGACGTGATGCCCGCCGACGTGTTCTCTGTGCGGTTG

GGGGAACATAACCTTTACTCGACCGATGATGACTCCAACCCAATCGATTTCGCCGTGACGTCCG

TGAAGCACCATGAGCACTTCGTGCTGGCCACCTACCTGAACGACATAGCAATTCTCACTCTGAA

CGACACCGTGACTTTTACTGATCGGATCAGGCCAATCTGTCTGCCGTACCGCAAGCTCAGATAC

GACGACCTGGCCATGCGCAAGCCGTTCATTACGGGTTGGGGAACTACCGCCTTCAACGGACCTT

CCTCCGCCGTGCTGCGGGAAGTGCAGCTGCCGATCTGGGAGCACGAAGCCTGTAGACAAGCCTA

CGAAAAGGACCTGAACATTACCAACGTGTATATGTGTGCCGATTCGCGGATGGCGGCAAAGAC

GCATGCCAGGGAGACTCCGGCGGCCCGATGATGCTGCCTGTGAAAACCGGAGAGTTCTACCTCA

TCGGCATCGTCAGCTTCGGGAAGAAATGCGCCCTGCCCGGATTCCCCGGAGTGTACACTAAGGT

CACCGAGTTCCTCGACTGGATTGCCGAACACATGGTGTAA

SEQ ID NO: 17
STLSRQRRQFVFPDEEELCSNRFTEEGTCKNVLDCRILLQKNDYNLLKESICGFEGITPKVCCP

KSSHVISSTQAPPETTTTERPPKQIPPNLPEVCGIHNTTTTRIIGGREAPIGAWPWMTAVYIKQ

GGIRSVQCGGALVTNRHVITASHCVVNSAGTDVMPADVFSVRLGEHNLYSTDDDSNPIDFAVTS

VKHHEHFVLATYLNDIAILTLNDTVTFTDRIRPICLPYRKLRYDDLAMRKPFITGWGTTAFNGP

SSAVLREVOLPIWEHEACRQAYEKDLNITNVYMCAGFADGGKDACQGDSGGPMMLPVKTGEFYL

IGIVSFGKKCALPGFPGVYTKVTEFLDWIAEHMV (Residues 1-21 represent the signal sequence)

SEQ ID NO: 18
MLVNNVFSLLCFPLLMSVVRCSTLSRQRRQFVFPDEEELCSNRFTEEGTCKNVLDCRILLQKND

YNLLKESICGFEGITPKVCCPKSSHVISSTQAPPETTTTERPPKQIPPNLPEVCGIHNTTTTRI

IGGREAPIGAWPWMTAVYIKQGGIRSVQCGGALVTNRHVITASHCVVNSAGTDVMPADVFSVRL

GEHNLYSTDDDSNPIDFAVTSVKHHEHFVLATYLNDIAILTLNDTVTFTDRIRPICLPYRKLRY

DDLAMRKPFITGWGTTAFNGPSSAVLREVQLPIWEHEACRQAYEKDLNITNVYMCAGFADGGKD

ACQGDSGGPMMLPVKTGEFYLIGIVSFGKKCALPGFPGVYTKVTEFLDWIAEHMV

What is claimed is:

1. A composition comprising a recombinant factor C, a recombinant factor B, and a recombinant pro-clotting enzyme,
  wherein the recombinant factor C lacks (α-2,3)-linked terminal sialic acid; and
  wherein the recombinant Factor C comprises the amino acid sequence of SEQ ID NO: 2, the recombinant Factor B comprises the amino acid sequence of SEQ ID NO: 5, and the recombinant pro-clotting enzyme comprises the amino acid sequence of SEQ ID NO: 8.

2. The composition of claim 1, wherein said composition remains stable in a salt solution.

3. The composition of claim 1, wherein the composition is contained within a vial or on a cartridge for use in bacterial endotoxin testing.

4. A kit for bacterial endotoxin testing comprising the composition of claim 1.

5. The composition of claim 1, wherein the composition has equivalent endotoxin detection activity in the presence of 214 mM sodium chloride to that of a composition comprising recombinant *Limulus* factor B, recombinant *Limulus* proclotting enzyme, and recombinant *Limulus* Factor C, where the recombinant *Limulus* factor C is produced in a HEK 293 cell line.

6. The composition of claim 1, wherein the composition has equivalent endotoxin detection activity in the presence of 428 mM sodium chloride to that of a composition comprising recombinant *Limulus* factor B, recombinant *Limulus* proclotting enzyme, and recombinant *Limulus* Factor C, where the recombinant *Limulus* factor C is produced in a HEK 293 cell line.

7. The composition of claim 1, wherein the composition has equivalent endotoxin detection activity in the presence of 16 mM magnesium sulfate to that of a composition comprising recombinant *Limulus* factor B, recombinant *Limulus* proclotting enzyme, and recombinant *Limulus* Factor C, where the recombinant *Limulus* factor C is produced in a HEK 293 cell line.

8. The composition of claim 1, wherein the composition has equivalent endotoxin detection activity in the presence of 2.5 mM calcium chloride to that of a composition comprising recombinant *Limulus* factor B, recombinant *Limulus* proclotting enzyme, and recombinant *Limulus* Factor C, where the recombinant *Limulus* factor C is produced in a HEK 293 cell line.

9. The composition of claim 1, wherein the composition has equivalent endotoxin detection activity in the presence of 21 mM sodium citrate to that of a composition comprising recombinant *Limulus* factor B, recombinant *Limulus* proclotting enzyme, and recombinant *Limulus* Factor C, where the recombinant *Limulus* factor C is produced in a HEK 293 cell line.

10. The composition of claim 1, wherein the composition has equivalent endotoxin detection activity in the presence of 52 mM sodium hydrogen carbonate to that of a composition comprising recombinant *Limulus* factor B, recombinant *Limulus* proclotting enzyme, and recombinant *Limulus* Factor C, where the recombinant *Limulus* factor C is produced in a HEK 293 cell line.

11. The composition of claim 1, wherein the composition does not experience salt inhibition in the presence of 214 sodium chloride, 428 mM sodium chloride, 16 mM magnesium sulfate, 2.5 mM calcium chloride, 21 mM sodium citrate or 52 mM sodium hydrogen carbonate.

* * * * *